United States Patent
Lee et al.

(10) Patent No.: US 9,486,440 B2
(45) Date of Patent: Nov. 8, 2016

(54) USES OF INDOLE-KETONES OR INDOLIDONES AS NEURO-PROTECTIVE DRUGS

(71) Applicants: UNIVERSITY OF MACAU, Macau (CN); THE HONG KONG POLYTECHNIC UNIVERSITY, Hong Kong (CN)

(72) Inventors: Ming Yuen Lee, Macau (CN); Yifan Han, Hong Kong (CN); Chung Lit Choi, Hong Kong (CN); Zaijun Zhang, Macau (CN); Wei Cui, Hong Kong (CN)

(73) Assignees: UNIVERSITY OF MACAU, Macau (CN); THE HONG KONG POLYTECHNIC UNIVERSITY, Hong Kong (CN)

(*) Notice: Subject to any disclaimer, the term of this patent is extended or adjusted under 35 U.S.C. 154(b) by 0 days.

(21) Appl. No.: 14/354,137

(22) PCT Filed: Oct. 25, 2012

(86) PCT No.: PCT/IB2012/055891
§ 371 (c)(1),
(2) Date: Apr. 25, 2014

(87) PCT Pub. No.: WO2013/061279
PCT Pub. Date: May 2, 2013

(65) Prior Publication Data
US 2014/0271480 A1  Sep. 18, 2014

(30) Foreign Application Priority Data
Oct. 25, 2011 (CN) .......................... 2011 1 0327436

(51) Int. Cl.
| | | |
|---|---|---|
| *A61K 31/404* | (2006.01) | |
| *A61K 35/28* | (2015.01) | |
| *A61K 35/545* | (2015.01) | |
| *A61K 49/00* | (2006.01) | |

(52) U.S. Cl.
CPC ............ *A61K 31/404* (2013.01); *A61K 35/28* (2013.01); *A61K 35/545* (2013.01); *A61K 49/00* (2013.01)

(58) Field of Classification Search
None
See application file for complete search history.

(56) References Cited

U.S. PATENT DOCUMENTS

| | | |
|---|---|---|
| 6,573,293 B2 | 6/2003 | Tang |
| 7,125,905 B2 | 10/2006 | Tang |
| 2007/0010569 A1 | 1/2007 | Tang |

(Continued)

FOREIGN PATENT DOCUMENTS

| | | |
|---|---|---|
| CN | 101023944 | 8/2007 |
| WO | 2010017541 | 2/2010 |
| WO | 2011057204 | 5/2011 |

OTHER PUBLICATIONS

Deckel 2001 "Nitric oxide and nitric oxide synthase in huntington's disease" J neurosci research 64:(99-107).*

(Continued)

*Primary Examiner* — Adam M Weidner
(74) *Attorney, Agent, or Firm* — Law Offices of Albert Wai-Kit Chan, PLLC

(57) ABSTRACT

The present invention provides a method of using indole-ketone or indolidone such as SU4312, SU5416, SU11248 (Sunitinib), or indirubin-3-oxime to treat a neurodegenerative disease or disorder such as Parkinson's disease which is associated with excessive neuronal Nitric Oxide Synthase (nNOS) activity.

8 Claims, 32 Drawing Sheets

(56) References Cited

U.S. PATENT DOCUMENTS

2010/0331327 A1    12/2010    Meijer
2011/0172206 A1*   7/2011    Zack et al. ............... 514/211.08
2012/0258995 A1    10/2012    Zhang

OTHER PUBLICATIONS

Farmer 2015 "Hematopoietic cytokines as therapetuic players in early stages Parkinson's disease" Front Aging Neurosci 7(126):1-5.*
Adams V.R., M. Leggas (2007). Sunitinib malate for the treatment of metastatic renal cell carcinoma and gastrointestinal stromal tumors, Clin Ther 29:1338-1353.
Addeo R., Caraglia M. (2011) The oral tyrosine kinase inhibitors lapatinib and sunitinib: new opportunities for the treatment of brain metastases from breast cancer?, Expert Rev Anticancer Ther 11 139-142.
Alderton WK, Cooper CE, Knowles RG (2001). Nitric oxide synthases: structure, function and inhibition. Biochem J 357 (Pt 3): 593-615.
Beckman JS, Beckman TW, Chen J, Marshall PA, Freeman BA (1990). Apparent hydroxyl radical production by peroxynitrite: implications for endothelial injury from nitric oxide and superoxide. Proc Natl Acad Sci U S A 87(4): 1620-1624.
Blay J.Y., (2010) Pharmacological management of gastrointestinal stromal tumours: an update on the role of sunitinib, Ann Oncol 21 208-215.
Choi DY, Liu M, Hunter RL, Cass WA, Pandya JD, et al. (2009) Striatal neuroinflammation promotes Parkinsonism in rats. PLoS One 4: e5482.
Cui W, Li W, Han R, Mak S, Zhang H, Hu S, et al. (2011). PI3-K/Akt and ERK pathways activated by VEGF play opposite roles in MPP+-induced neuronal apoptosis. Neurochem Int 59(6): 945-953.
I.M. Desar, D.M. Burger, Q.G. Van Hoesel, J.H. Beijnen, C.M. Van Herpen, W.T. Van der Graaf, (2009) Pharmacokinetics of sunitinib in an obese patient with a GIST, Ann Oncol 20 599-600.
Estevez AG, Spear N, Thompson JA, Cornwell TL, Radi R, Barbeito L, et al. (1998). Nitric oxide-dependent production of cGMP supports the survival of rat embryonic motor neurons cultured with brain-derived neurotrophic factor. J Neurosci 18(10): 3708-3714.
Fedorov R, Vasan R, Ghosh DK, Schlichting I (2004). Structures of nitric oxide synthase isoforms complexed with the inhibitor AR-R17477 suggest a rational basis for specificity and inhibitor design. Proc Natl Acad Sci U S A 101(16): 5892-5897.
Fong TA, Shawver LK, Sun L, Tang C, App H, et al. (1999) SU5416 is a potent and selective inhibitor of the vascular endothelial growth factor receptor (Flk-1/KDR) that inhibits tyrosine kinase catalysis, tumor vascularization, and growth of multiple tumor types. Cancer Res 59: 99-106.
Fu H., J. Dou, W. Li, J. Luo, K.C. Li, C.S. Lam, N.T. Lee, M. Li, Y. Han (2008). Mecamylamine prevents neuronal apoptosis induced by glutamate and low potassium via differential anticholinergic-independent mechanisms, Neuropharmacology 54 755-765.
Gal S, Zheng H, Fridkin M, Youdim MB (2010) Restoration of nigrostriatal dopamine neurons in post-MPTP treatment by the novel multifunctional brain-permeable iron chelator-monoamine oxidase inhibitor drug, M30. Neurotox Res 17: 15-27.
Gonzalez-Polo RA, Soler G, Alvarez A, Fabregat I, Fuentes JM (2003). Vitamin E blocks early events induced by 1-methyl-4-phenylpyridinium (MPP+) in cerebellar granule cells. J Neurochem 84(2): 305-315.
Gonzalez-Polo RA, Soler G, Fuentes JM (2004a). MPP+: mechanism for its toxicity in cerebellar granule cells. Mol Neurobiol 30(3): 253-264.
Gonzalez-Polo RA, Soler G, Rodriguezmartin A, Moran JM, Fuentes JM (2004b). Protection against MPP+ neurotoxicity in cerebellar granule cells by antioxidants. Cell Biol Int 28(5): 373-380.
Grayson M (2010) Parkinson's disease. Nature 466: S1.
Hantraye P, Brouillet E, Ferrante R, Palfi S, Dolan R, Matthews RT, et al. (1996). Inhibition of neuronal nitric oxide synthase prevents MPTP-induced parkinsonism in baboons. Nat Med 2(9): 1017-1021.
Herraiz T, Aran VJ, Guillen H (2009). Nitroindazole compounds inhibit the oxidative activation of 1-methyl-4-phenyl-1,2,3,6-tetrahydropyridine (MPTP) neurotoxin to neurotoxic pyridinium cations by human monoamine oxidase (MAO). Free Radic Res 43(10): 975-984.
Kieran MW, Supko JG, Wallace D, Fruscio R, Poussaint TY, et al. (2009) Phase I study of SU5416, a small molecule.inhibitor of the vascular endothelial growth factor receptor (VEGFR) in refractory pediatric central nervous system tumors. Pediatr Blood Cancer 52: 169-176.
Langston JW, Irwin I (1986). MPTP: current concepts and controversies. Clin Neuropharmacol 9(6): 485-507.
Lee BD, Shin JH, VanKampen J, Petrucelli L, West AB, Ko HS, et al. (2010). Inhibitors of leucine-rich repeat kinase-2 protect against models of Parkinson's disease. Nat Med 16(9): 998-1000.
Lees AJ, Hardy J, Revesz T (2009) Parkinson's disease. Lancet 373: 2055-2066.
McKinley ET, Baranowski TC, Blavo DO, Cato C, Doan TN, Rubinstein AL (2005). Neuroprotection of MPTP-induced toxicity in zebrafish dopaminergic neurons. Brain Res Mol Brain Res 141(2): 128-137.
McMillin DW, Delmore J, Weisberg E, Negri JM, Geer DC, Klippel S, et al. (2010). Tumor cell-specific bioluminescence platform to identify stroma-induced changes to anticancer drug activity. Nat Med 16(4): 483-489.
Medioni J., Cojocarasu O., Belcaceres J.L., Halimi P., Oudard S., (2007) Complete cerebral response with sunitinib for metastatic renal cell carcinoma, Ann Oncol 18 1282-1283.
Miki A, Miki K, Ueno S, Wersinger DM, Berlinicke C, Shaw GC, et al. (2010). Prolonged blockade of VEGF receptors does not damage retinal photoreceptors or ganglion cells. J Cell Physiol 224(1): 262-272.
Muramatsu Y, Kurosaki R, Watanabe H, Michimata M, Matsubara M, et al. (2003) Cerebral alterations in a MPTP-mouse model of Parkinson's disease—an immunocytochemical study. J Neural Transm 110: 1129-1144.
Nagl F, Schonhofer K, Seidler B, Mages J, Allescher HD, et al. (2009) Retinoic acid-induced nNOS expression depends on a novel PI3K/Akt/DAX1 pathway in human TGW-nu-I neuroblastoma cells. Am J Physiol Cell Physiol 297: C1146-1156.
Patyna S., G. Peng, (2006) Distribution of sunitinib and its active metabolite in brain and spinal cord tissue following oral or intravenous administration in rodents and monkeys, Eur J Cancer Suppl 12: 21.
Przedborski S, Jackson-Lewis V, Yokoyama R, Shibata T, Dawson VL, Dawson TM (1996). Role of neuronal nitric oxide in 1-methyl-4-phenyl-1,2,3,6-tetrahydropyridine (MPTP)-induced dopaminergic neurotoxicity. Proc Natl Acad Sci U S A 93(10): 4565-4571.
Rock E.P., V. Goodman, J.X. Jiang, K. Mahjoob, S.L. Verbois, D. Morse, R. Dagher, R. Justice, R. Pazdur, (2007) Food and Drug Administration drug approval summary: Sunitinib malate for the treatment of gastrointestinal stromal tumor and advanced renal cell carcinoma, Oncologist 12 107-113.
Rodamer M, Elsinghorst PW, Kinzig M, Gütschow M (2011) Development and validation of a liquid chromatography/tandem mass spectrometry procedure for the quantification of sunitinib (SU11248) and its active metabolite, N-desethyl sunitinib (SU12662), in human plasma: application to an explorative study. J Chromatogr B Analyt Technol Biomed Life Sci. 879(11-12):695-706.
Roman LJ, Masters BS (2006). Electron transfer by neuronal nitric-oxide synthase is regulated by concerted interaction of calmodulin and two intrinsic regulatory elements. J Biol Chem 281(32): 23111-23118.
Sabaliauskas NA, Foutz CA, Mest JR, Budgeon LR, Sidor AT, et al. (2006) High-throughput zebrafish histology. Methods 39: 246-254.

(56) References Cited

OTHER PUBLICATIONS

Schultheiss C, Blechert B, Gaertner FC, Drecoll E, Mueller J, Weber GF, et al. (2006). In vivo characterization of endothelial cell activation in a transgenic mouse model of Alzheimer's disease. Angiogenesis 9(2): 59-65.
Scott GS, Kean RB, Mikheeva T, Fabis MJ, Mabley JG, Szabo C, et al. (2004). The therapeutic effects of PJ34 [N-(6-oxo-5,6-dihydrophenanthridin-2-yl)-N,N-dimethylacetamide.HCI], a selective inhibitor of poly(ADP-ribose) polymerase, in experimental allergic encephalomyelitis are associated with immunomodulation. J Pharmacol Exp Ther 310(3): 1053-1061.
Shawver LK, Slamon D, Ullrich A (2002) Smart drugs: tyrosine kinase inhibitors in cancer therapy. Cancer Cell 1: 117-123.
Shin JH, Dawson VL, Dawson TM (2009) SnapShot: pathogenesis of Parkinson's disease. Cell 139: 440 e441-442.
Spitsin S, Portocarrero C, Phares TW, Kean RB, Brimer CM, Koprowski H, et al. (2008). Early blood-brain barrier permeability in cerebella of PLSJL mice immunized with myelin basic protein. J Neuroimmunol 196(1-2): 8-15.
Stopeck A, Sheldon M, Vahedian M, Cropp G, Gosalia R, et al. (2002) Results of a Phase I dose-escalating study of the antiangiogenic agent, SU5416, in patients with advanced malignancies. Clin Cancer Res 8: 2798-2805.
Sun L, Tran N, Tang F, App H, Hirth P, McMahon G, et al. (1998). Synthesis and biological evaluations of 3-substituted indolin-2-ones: a novel class of tyrosine kinase inhibitors that exhibit selectivity toward particular receptor tyrosine kinases. Journal of medicinal chemistry 41(14): 2588-2603.
Thomas B, Saravanan KS, Mohanakumar KP (2008) In vitro and in vivo evidences that antioxidant action contributes to the neuroprotective effects of the neuronal nitric oxide synthase and monoamine oxidase-B inhibitor, 7-nitroindazole. Neurochem Int 52: 990-1001.
Tipton KF, Singer TP (1993). Advances in our understanding of the mechanisms of the neurotoxicity of MPTP and related compounds. J Neurochem 61(4): 1191-1206.
Totrov M, Abagyan R (1997). Flexible protein-ligand docking by global energy optimization in internal coordinates. Proteins Suppl 1: 215-220.
Tran TC, Sneed B, Haider J, Blavo D, White A, Aiyejorun T, et al. (2007). Automated, quantitative screening assay for antiangiogenic compounds using transgenic zebrafish. Cancer Res 67(23): 11386-11392.
van der Veldt A.A., A.J. van den Eertwegh, K. Hoekman, F. Barkhof, E. Boven, Reversible cognitive disorders after sunitinib for advanced renal cell cancer in patients with preexisting arteriosclerotic leukoencephalopathy, Ann Oncol 18 (2007) 1747-1750.
Wen L, Wei W, Gu W, Huang P, Ren X, Zhang Z, et al. (2008). Visualization of monoaminergic neurons and neurotoxicity of MPTP in live transgenic zebrafish. Dev Biol 314(1): 84-92.
Westerfield M (1993). The Zebrafish book : a guide for the laboratory use of zebrafish (Brachydanio rerio). edn. University of Oregon Press: Eugene. Or.
Xue F, Li H, Delker SL, Fang J, Martasek P, Roman LJ, et al. (2010). Potent, highly selective, and orally bioavailable gem-difluorinated monocationic inhibitors of neuronal nitric oxide synthase. J Am Chem Soc 132(40): 14229-14238.
Ye C, Sweeny D, Sukbuntherng J, Zhang Q, Tan W, et al. (2006) Distribution, metabolism, and excretion of the anti-angiogenic compound SU5416. Toxicol In Vitro 20: 154-162.
Zhang L., K.M. Smith, A.L. Chong, D. Stempak, H. Yeger, P. Marrano, P.S. Thorner, M.S. Irwin, D.R. Kaplan, S. Baruchel, In vivo antitumor and antimetastatic activity of sunitinib in preclinical neuroblastoma mouse model, Neoplasia 11 (2009) 426-435.
Zhang ZJ, Cheang LC, Wang MW, Lee SM (2011). Quercetin exerts a neuroprotective effect through inhibition of the iNOS/NO system and pro-inflammation gene expression in PC12 cells and in zebrafish. Int J Mol Med 27(2): 195-203.
Zhou L, Zhu DY (2009). Neuronal nitric oxide synthase: structure, subcellular localization, regulation, and clinical implications. Nitric Oxide 20(4): 223-230.
Zhu Y, Jin K, Mao XO, Greenberg DA (2003) Vascular endothelial growth factor promotes proliferation of cortical neuron precursors by regulating E2F expression. FASEB J 17: 186-193.
Chines Office Action, Nov. 23, 2012, for Chinese App'l No. 201110327436.8, filed Oct. 25, 2011 (with English translation).
PCT International Search Report, Mar. 7, 2013, for Intl App'l No. PCT/IB2012/055891, filed Oct. 25, 2012.
PCT Written Opinion, Mar. 7, 2013, for Intl App'l No. PCT/IB2012/055891, filed Oct. 25, 2012.

\* cited by examiner

Figures 1 A-B
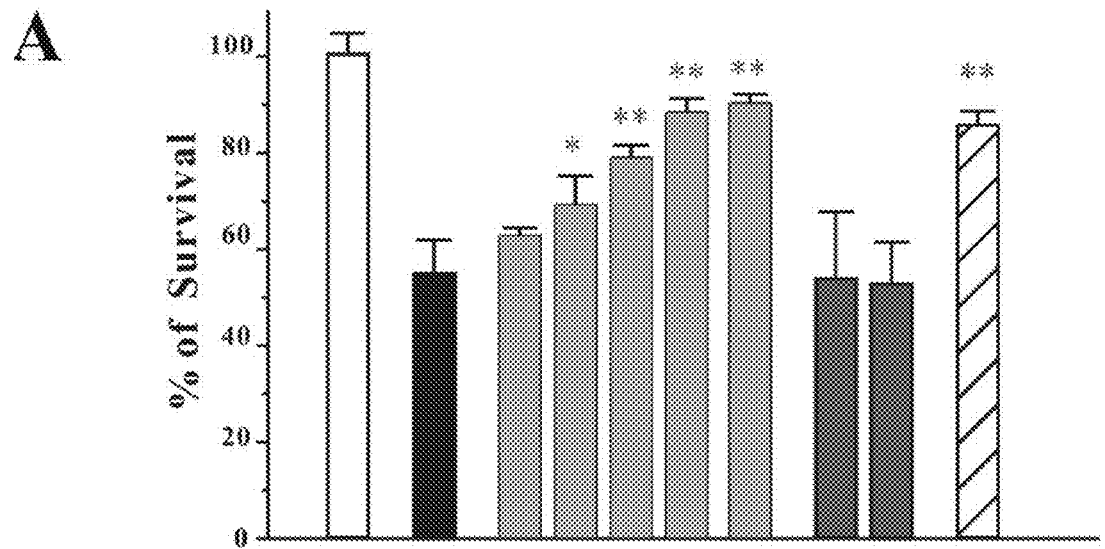
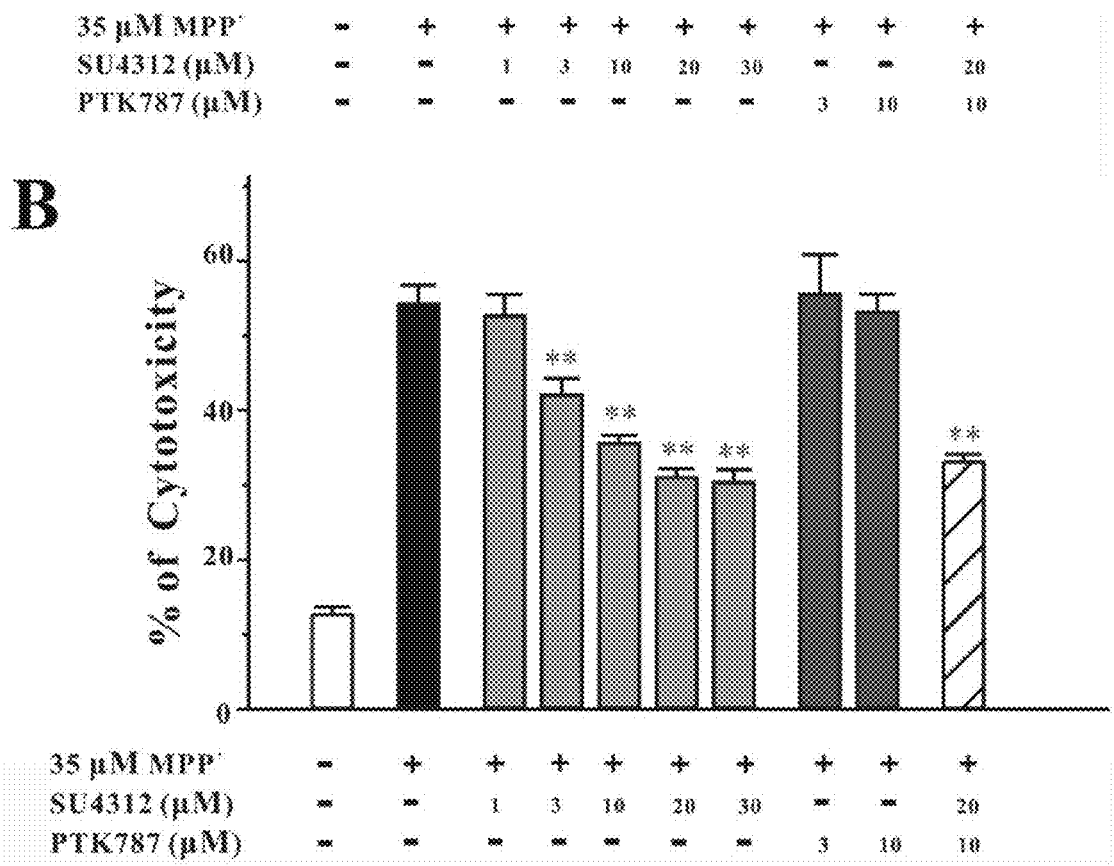

Figure 1 C-D
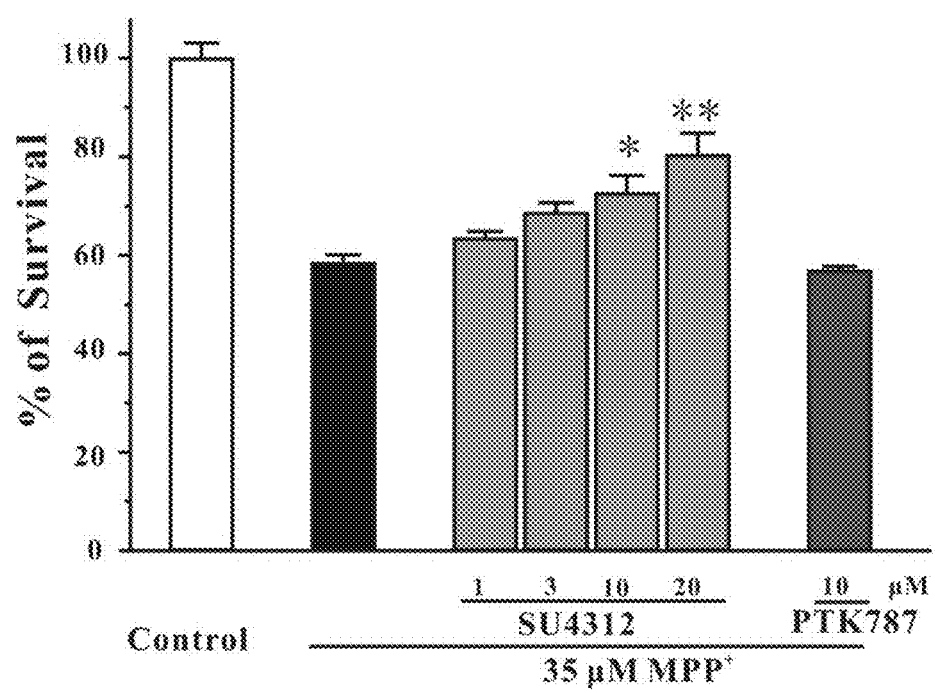
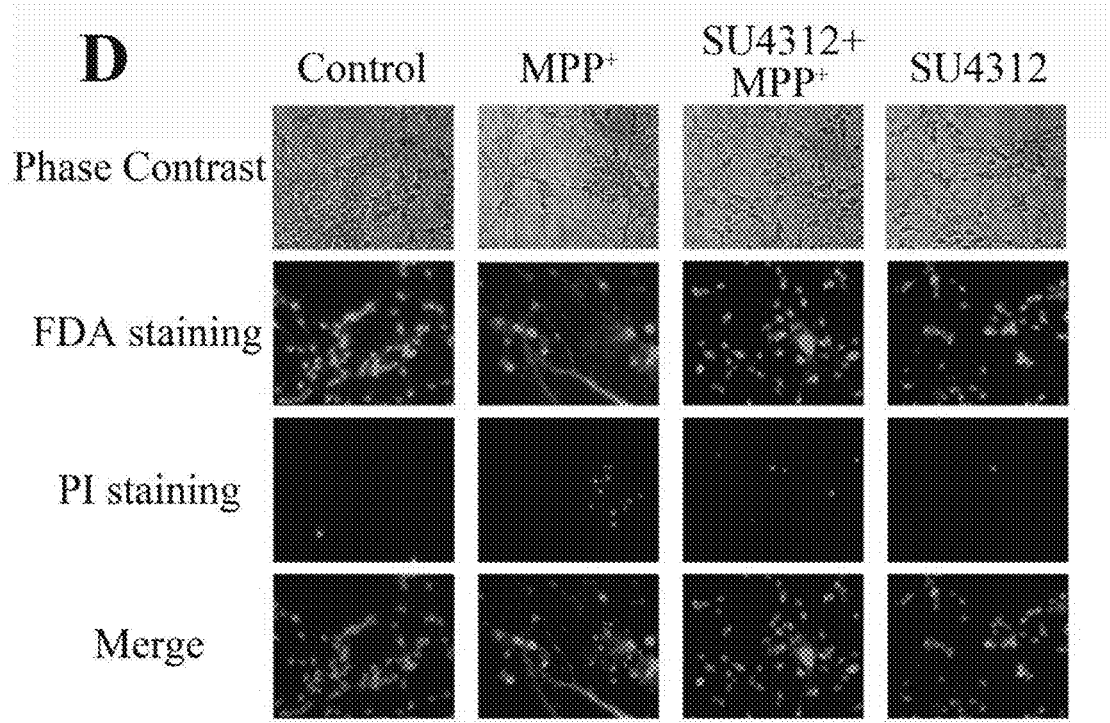

Figure 2
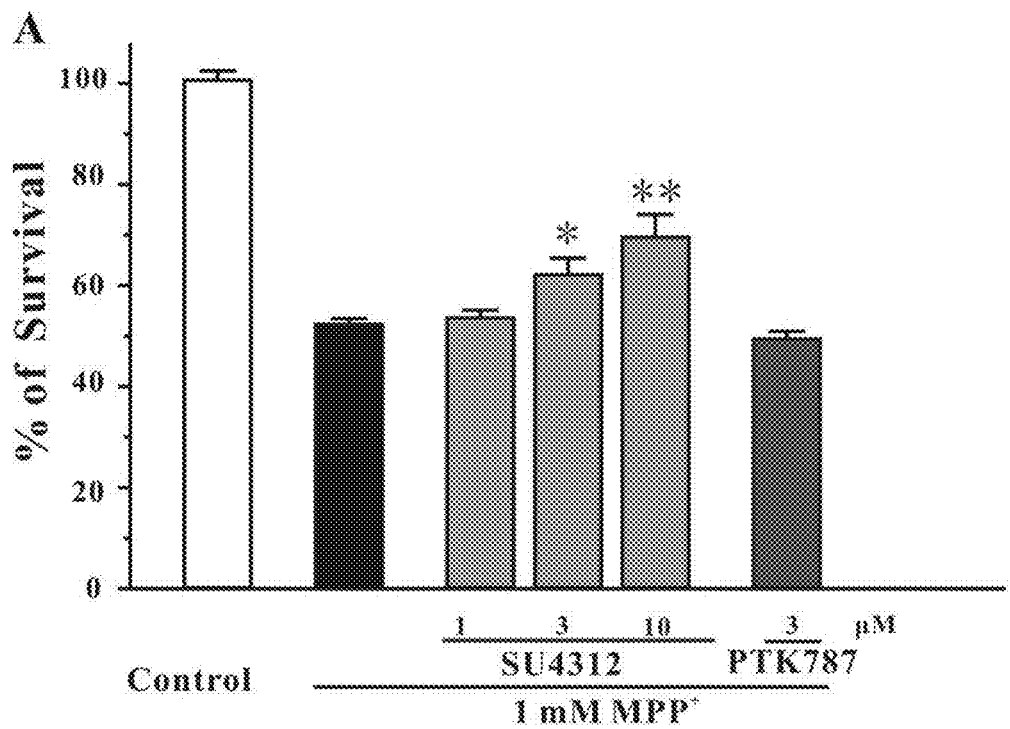
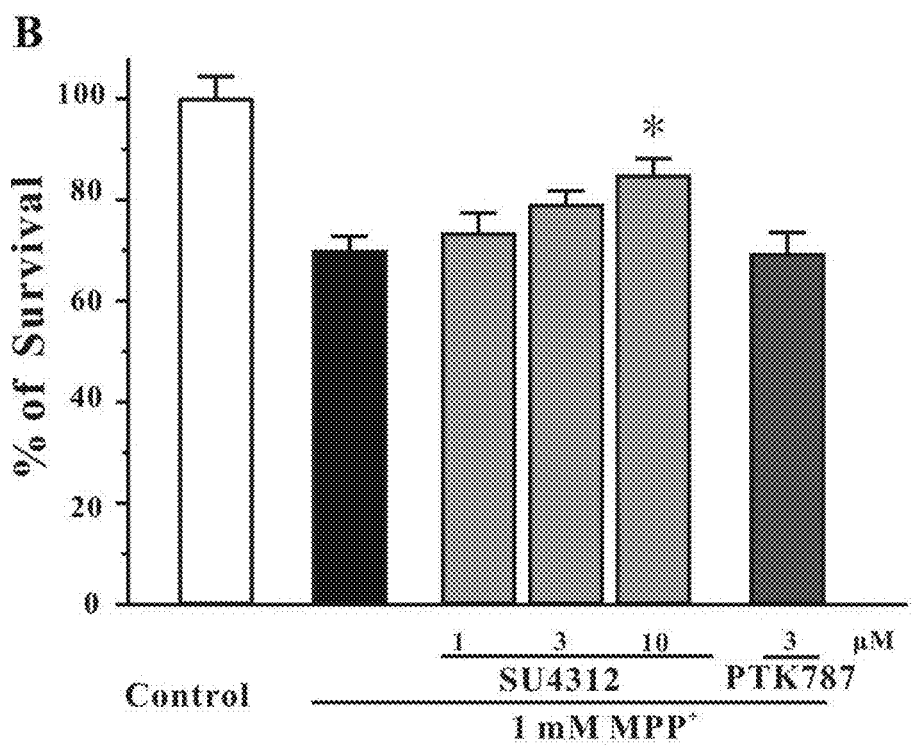

Figures 3 B-C
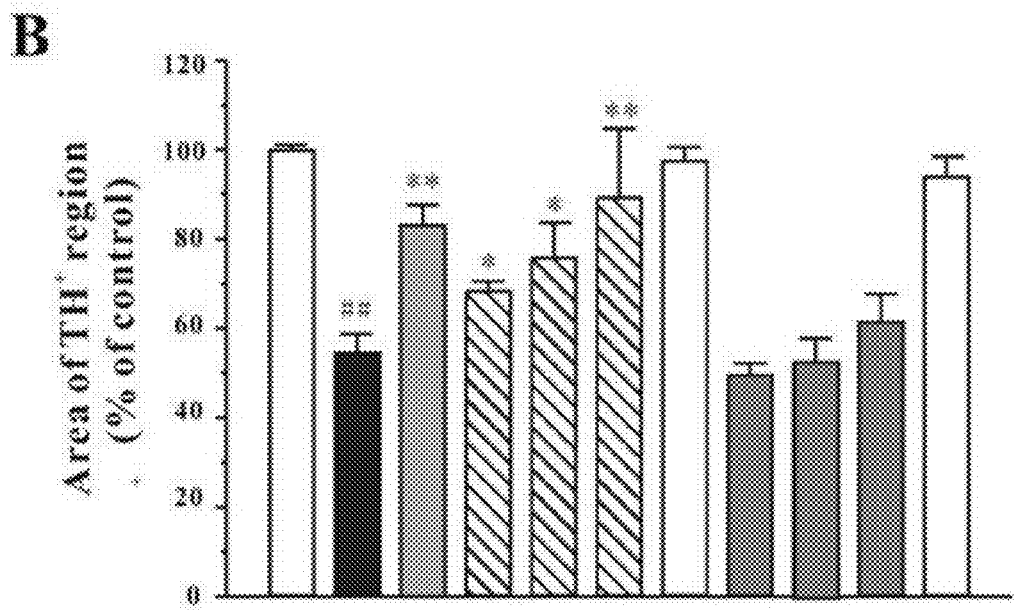
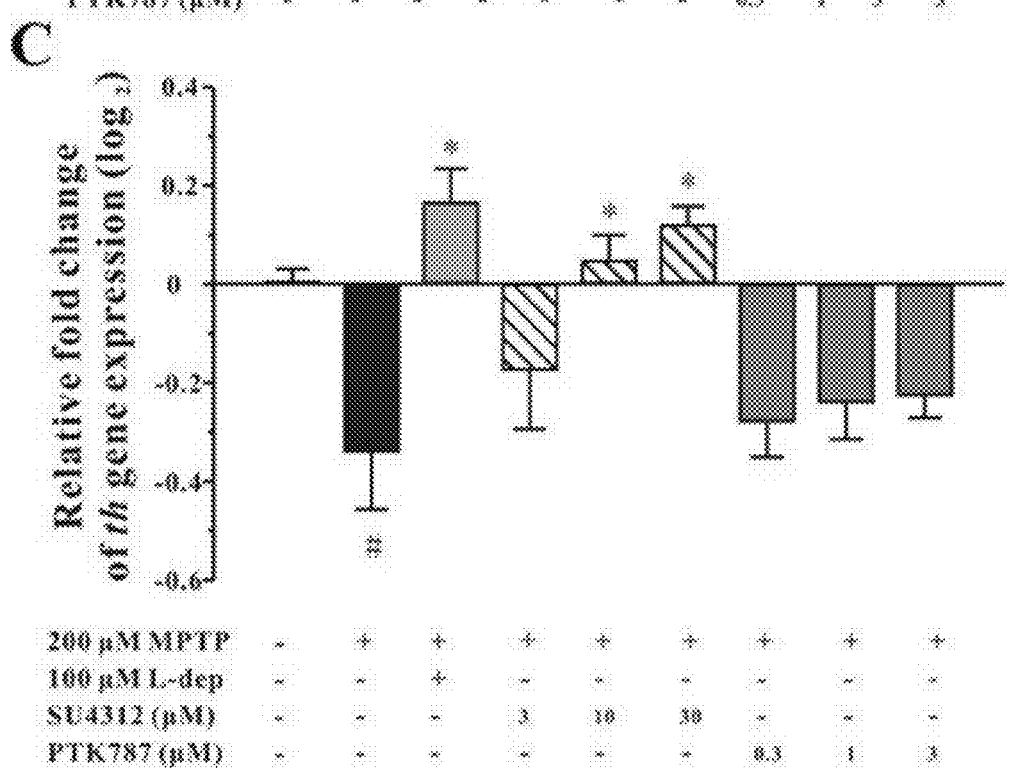

Figure 6B-C
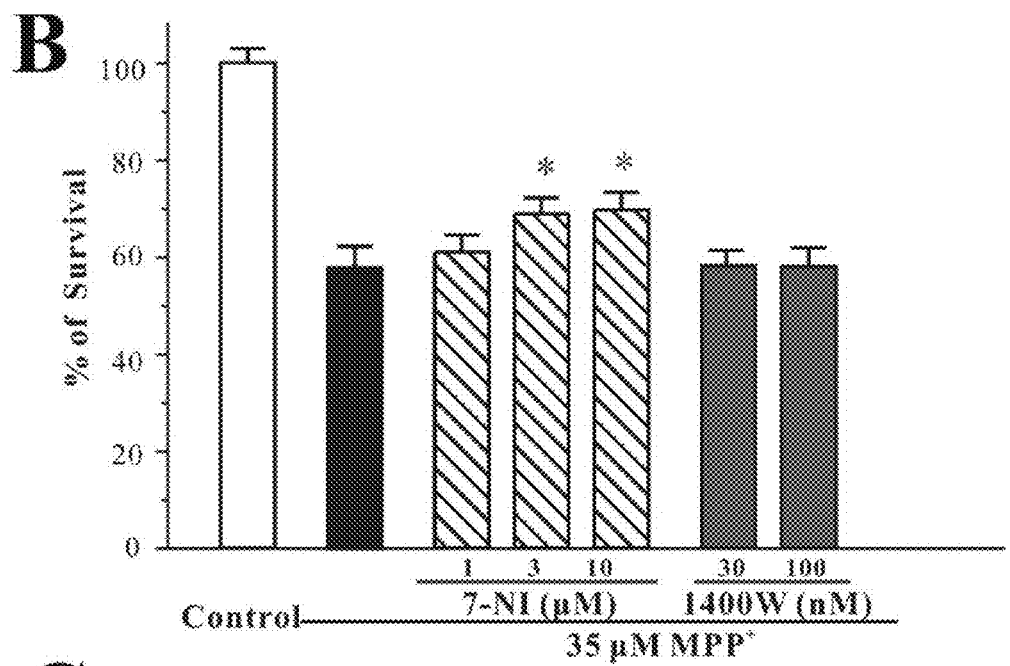
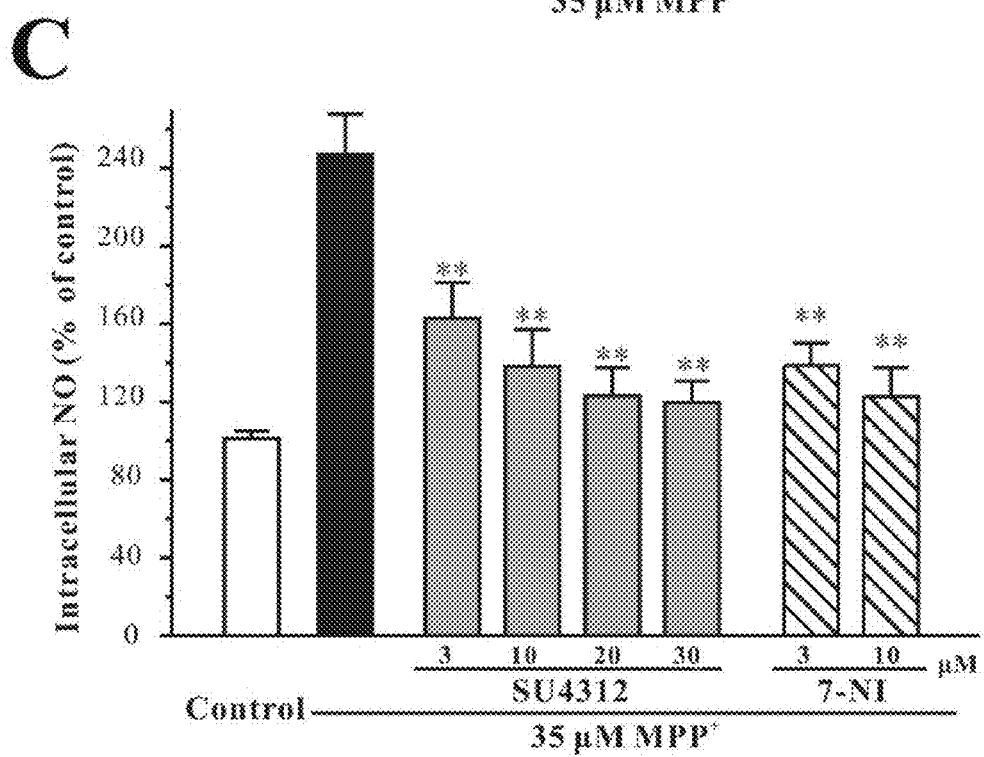

Figure 7
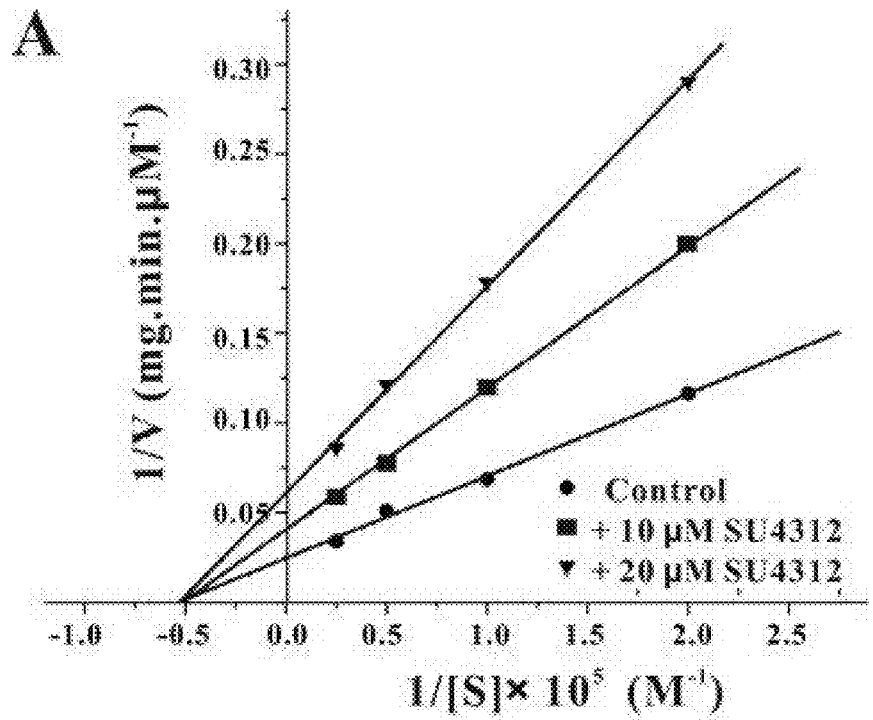
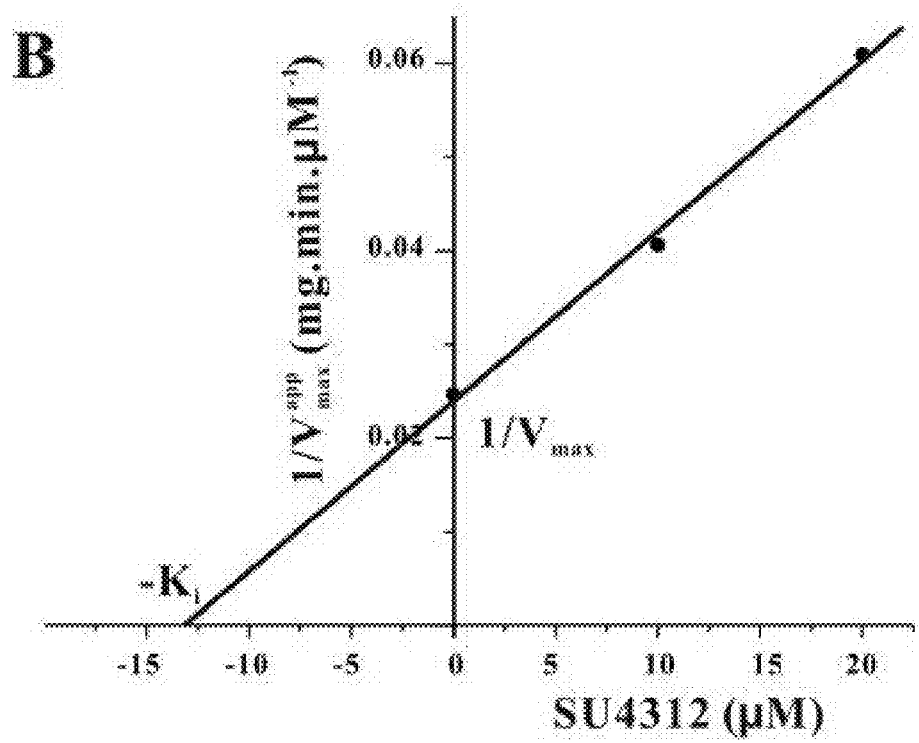

Figures 9A-C
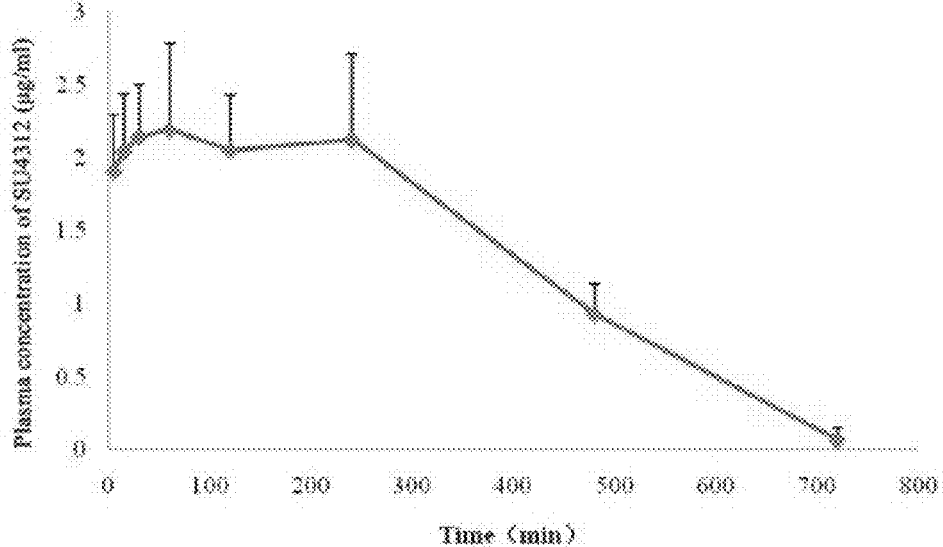
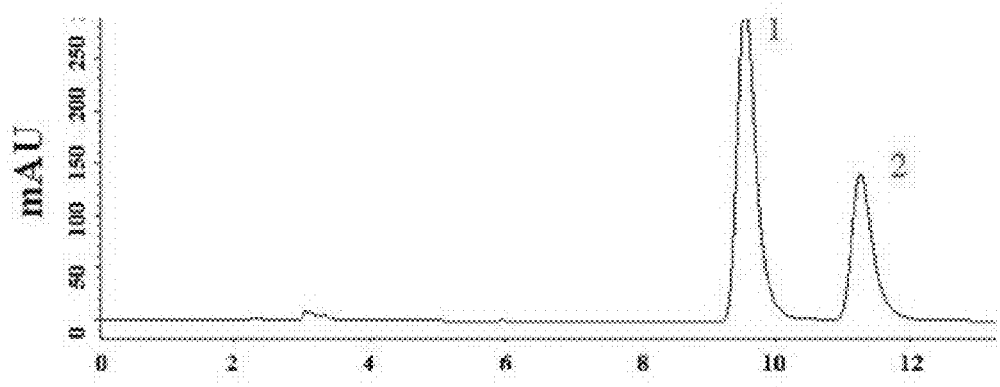
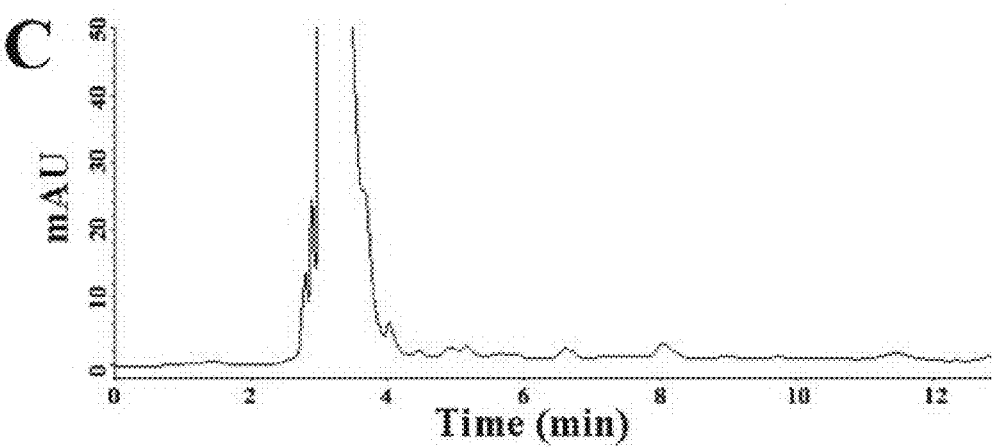

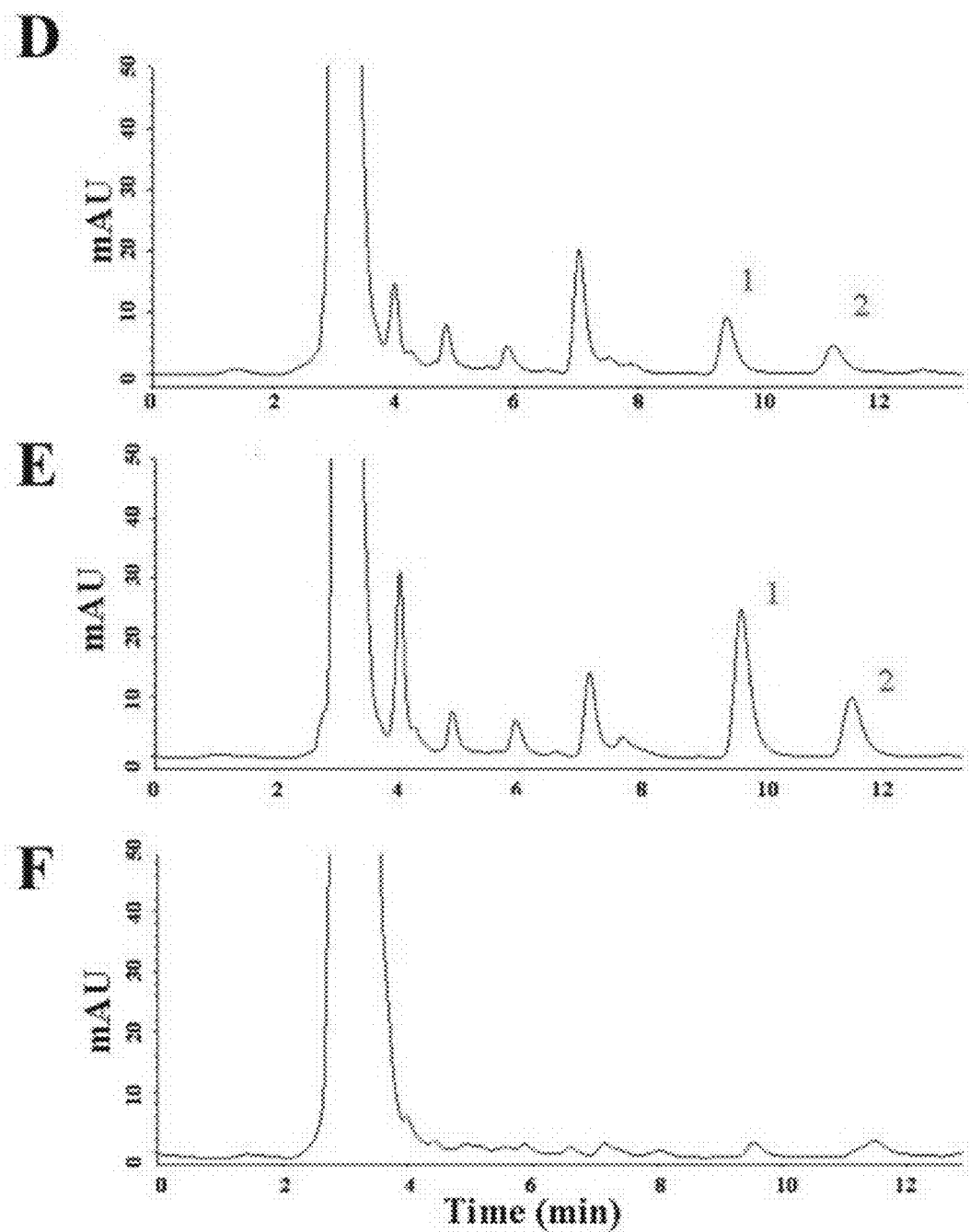
Figures 9D-F

Figures 12 A-B
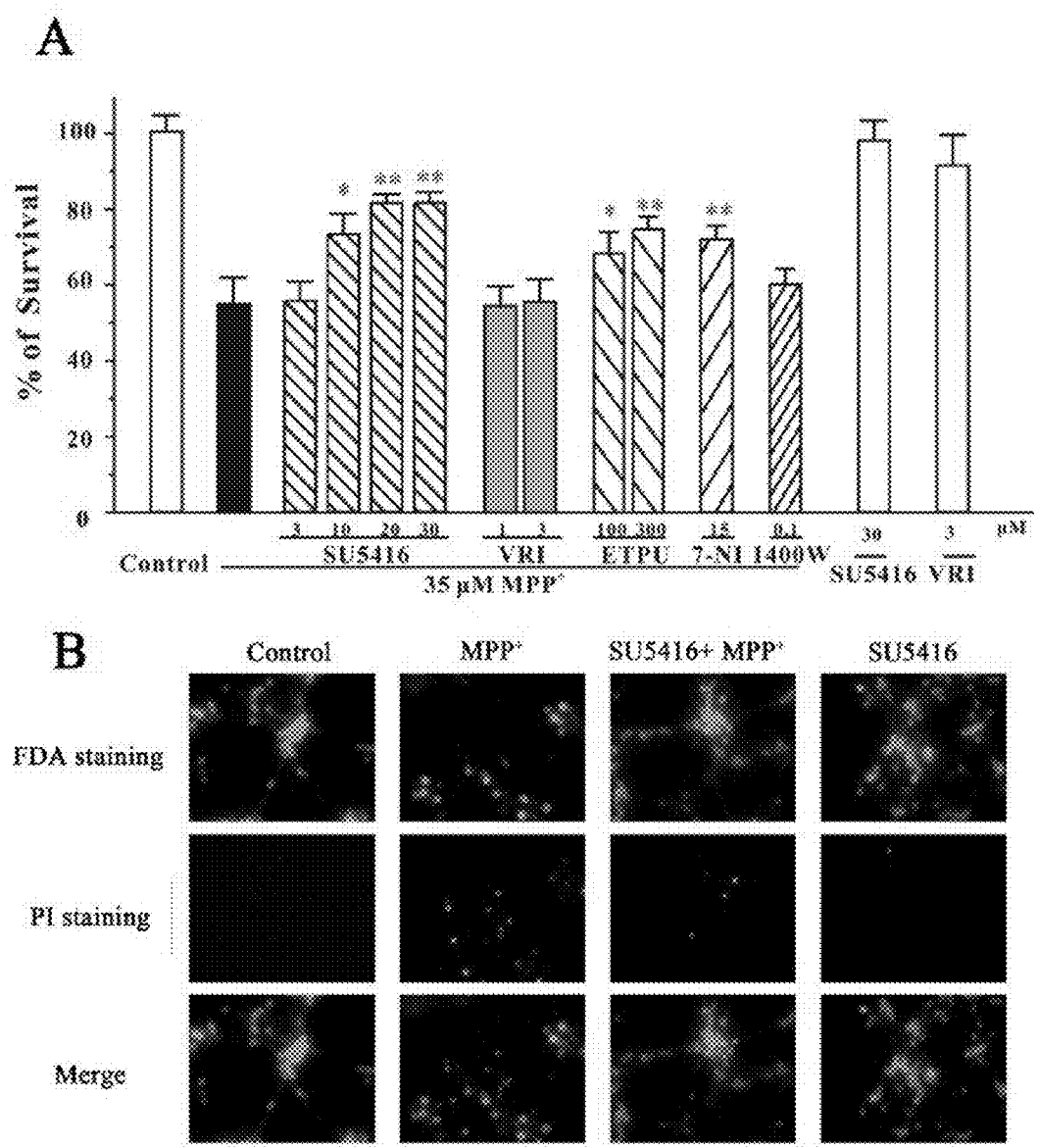

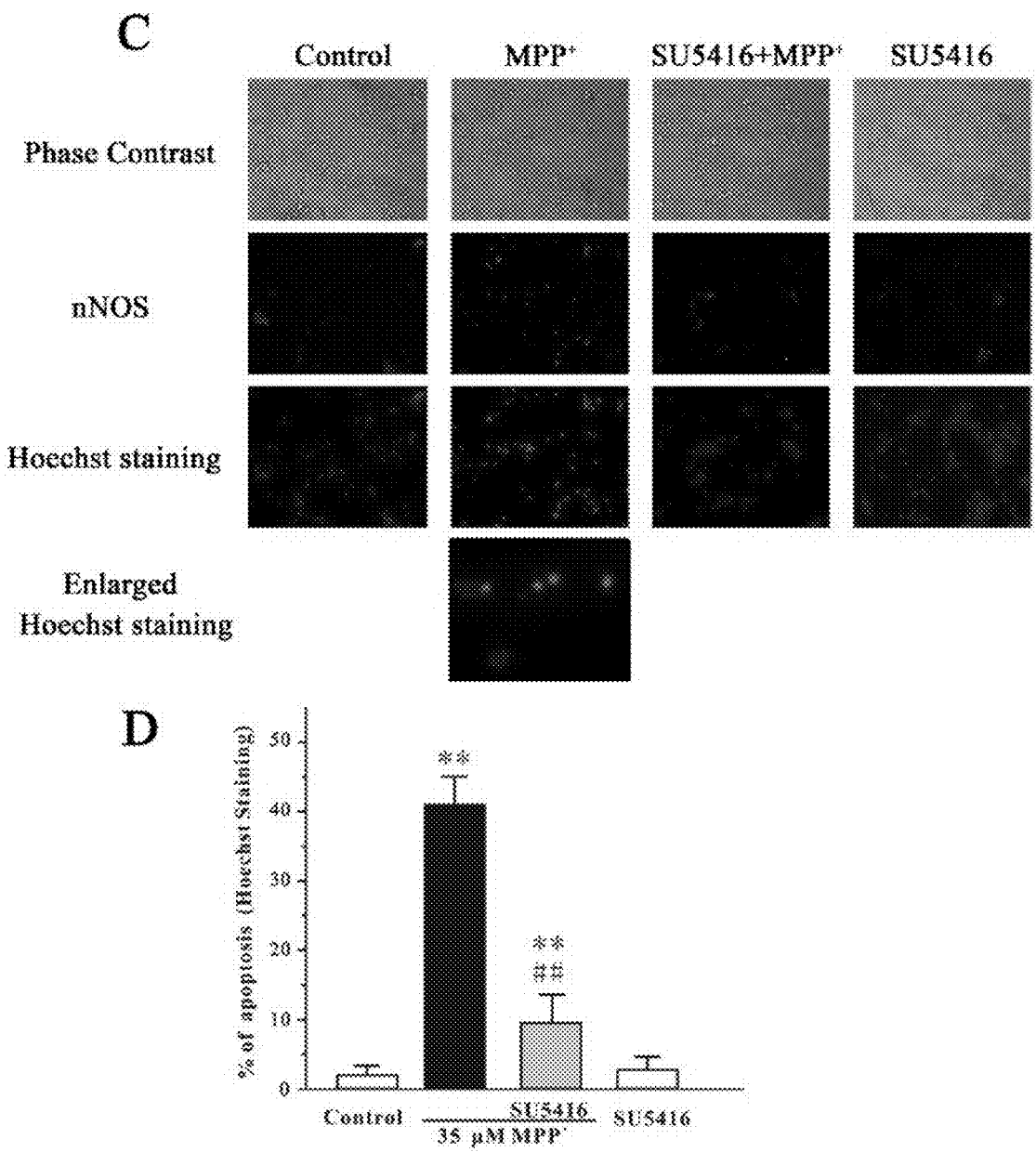
Figures 12 C-D

Figure 14
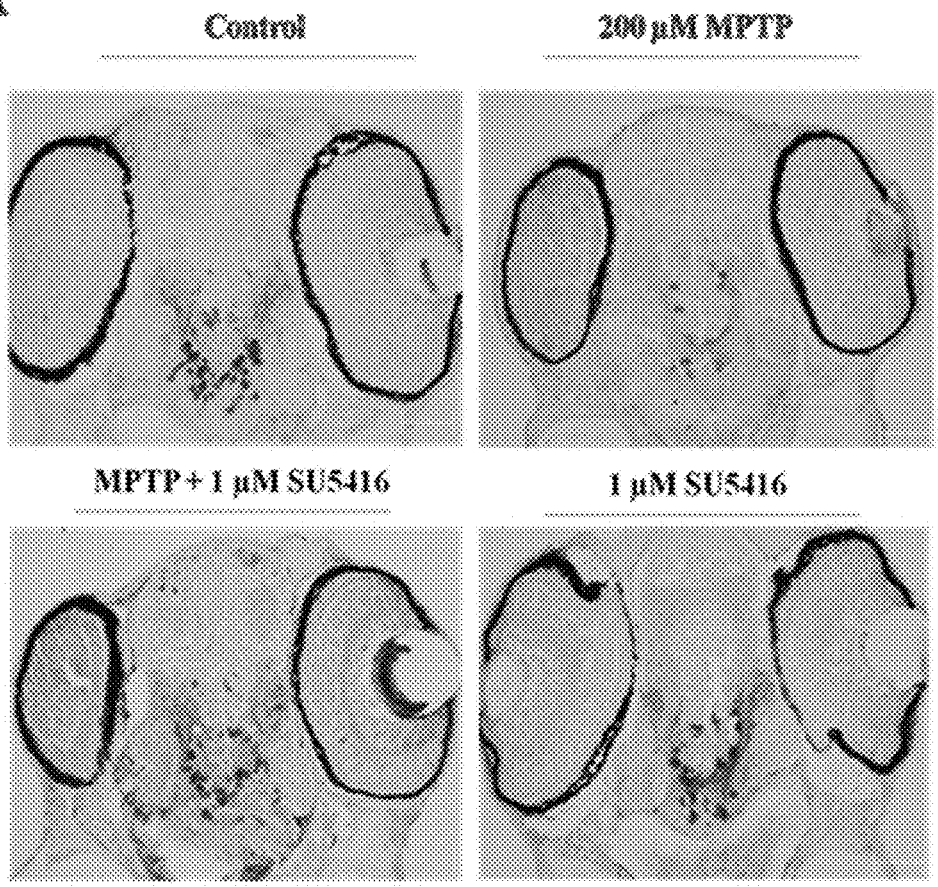
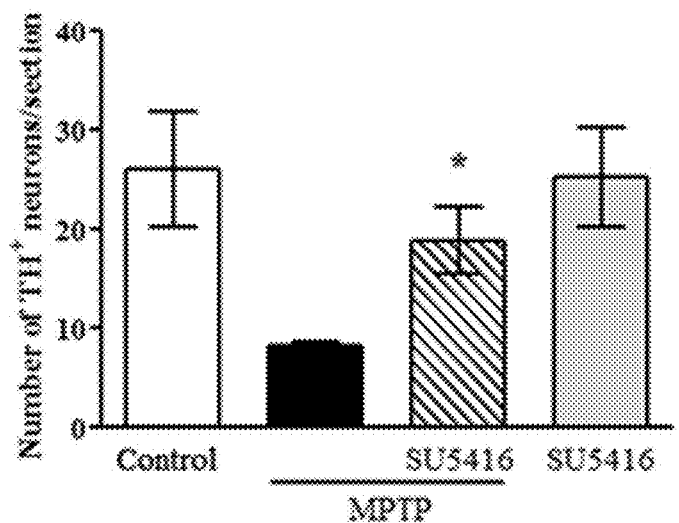

Figure 21
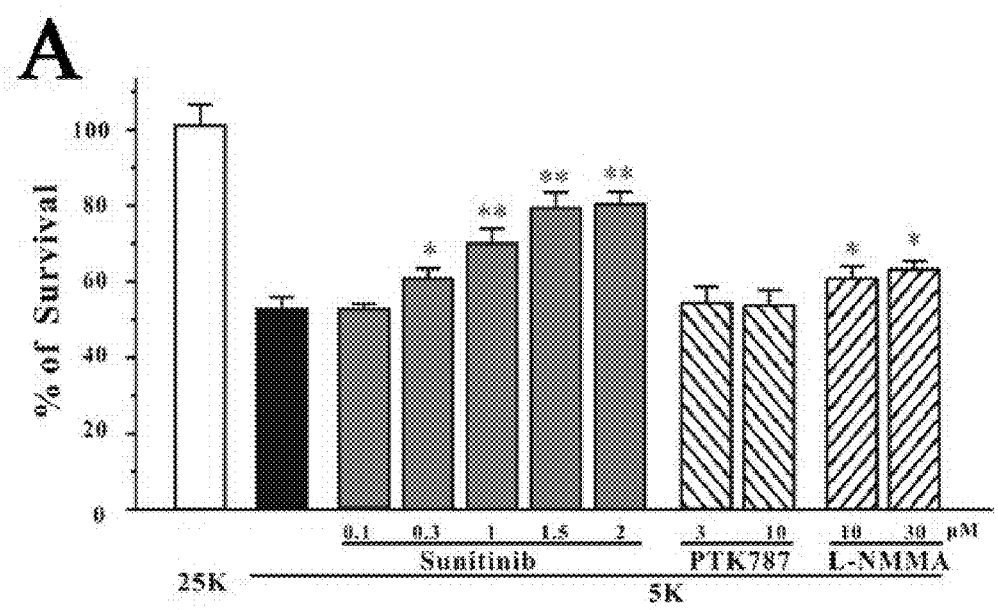
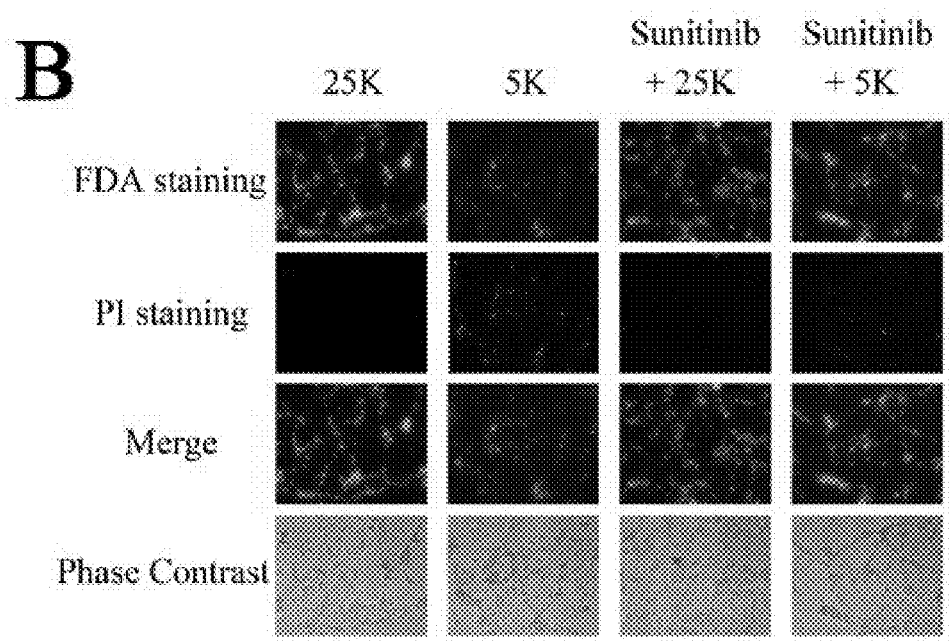

Figure 21
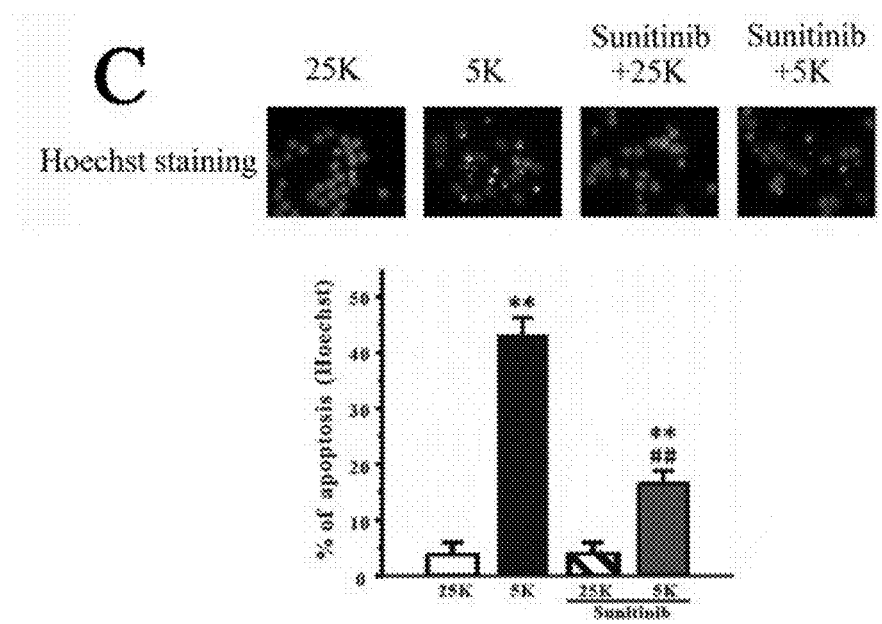
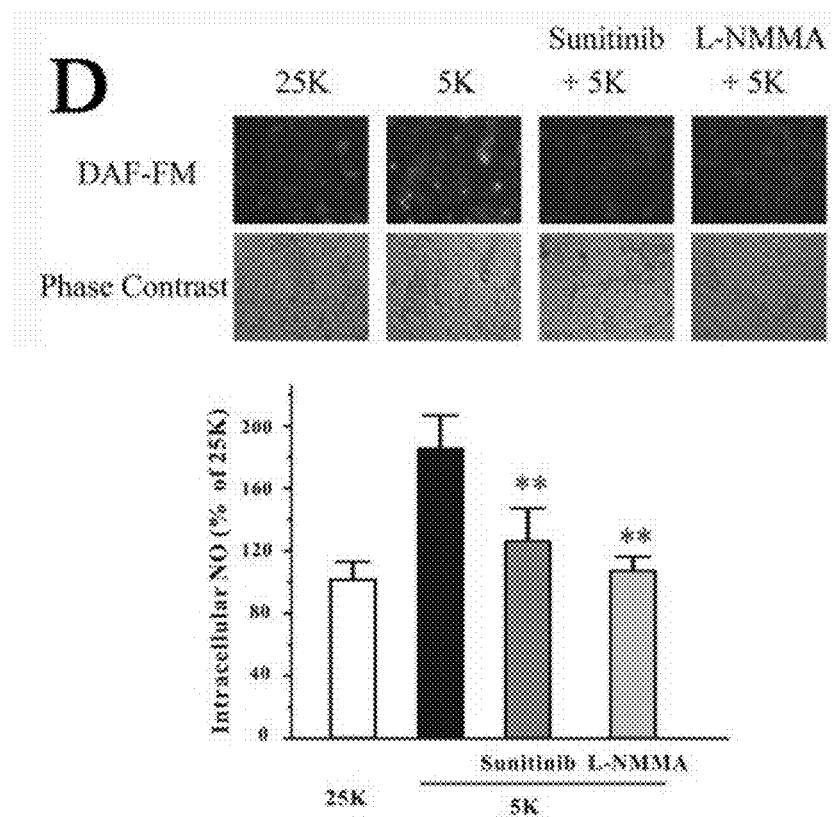

USES OF INDOLE-KETONES OR INDOLIDONES AS NEURO-PROTECTIVE DRUGS

This application is the National Stage of International Application No. PCT/IB2012/055891, filed Oct. 25, 2012, which claims priority of Chinese Application No. 201110327436.8, filed Oct. 25, 2011. The contents and disclosures of the preceding application is hereby incorporated in its entirety by reference into this application. Throughout this application, various publications are referenced. Disclosures of these publications in their entireties are hereby incorporated by reference into this application in order to more fully describe the state of the art to which this invention pertains.

FIELD OF THE INVENTION

This invention relates to the uses of indole-ketones or indolidones in the preparation of drugs for the treatment of neurodegenerative diseases such as Parkinson's disease. In one aspect of this invention, one mechanism of neuroprotection by indole-ketones or indolidones is through their inhibition of neuronal nitric oxide synthase (nNOS).

BACKGROUND OF THE INVENTION

Parkinson's disease (PD) is the second most common neurodegenerative disorder among the elderly worldwide (Lees et al., 2009; Grayson, 2010; Shin et al., 2009). Although the etiology of PD remains largely unknown, overproduction of nitric oxide (NO) is considered as a causative factor for the loss of dopaminergic neurons (Kavya et al., 2006).

1-Methyl-4-phenyl-1,2,3,6-tetrahydropyridine (MPTP) is a common neurotoxin widely used to produce PD models (Langston & Irwin, 1986). MPTP is converted into its active metabolite 1-methyl-4-phenylpyridinium ion ($MPP^+$) by the monoamine oxidase B (MAO-B) in the inner mitochondrial membrane (Tipton & Singer, 1993). $MPP^+$ stimulates the production of superoxide radical and activates nitric oxide synthase (NOS) to produce nitric oxide (NO) radical (Gonzalez-Polo et al., 2003; Gonzalez-Polo et al., 2004b). Superoxide radical not only inhibits mitochondrial complex I of the electron transport chain, but also reacts with NO radical to form peroxynitrite ion ($ONOO^-$), the precursor of the tissue-damaging hydroxyl radical (Beckman et al., 1990). Thus, inhibition of NOS activity decreases the production of NO radicals and further attenuates $MPTP/MPP^+$-induced neurotoxicity (Przedborski et al., 1996).

High levels of neuronal nitric oxide synthase (nNOS) are found in the nigrostriatal regions and basal ganglia of post-mortem PD brains and animals treated with 1-methyl-4-phenyl-1,2,3,6-tetrahydropyridine (MPTP), a PD-inducing neurotoxin (Muramatsu et al., 2003). On the other hand, transgenic mice that lack the nNOS gene are more resistant to MPTP than wild-type mice (Hantraye et al., 1996). Selective nNOS inhibitors produce neuroprotective effects against MPTP both in vitro and in vivo. These results suggest that nNOS inhibitors might have therapeutic potential in the treatment of PD (Kavya et al., 2006; Li et al., 2007; Li et al., 2006; Choi et al., 2009).

SU4312 (3-[4-(dimethylamino)benzylidenyl]indolin-2-one) is a cell-permeable, potent and selective inhibitor of the vascular endothelial growth factor receptor-2 (VEGFR-2) tyrosine kinase, that has been designed as a candidate drug for cancer therapy (Sun et al., 1998). SU4312 competes with ATP for binding to VEGFR-2 and is able to completely block vascular endothelial growth factor (VEGF) signaling in a non-competitive manner (Sun et al., 1998). Previous studies have demonstrated that SU4312 specifically inhibits VEGF-dependent angiogenesis without damaging normal cells (Miki et al., 2010; Tran et al., 2007). SU4312 also significantly reduces the proliferation of multiple myeloma and leukemia tumor cells in vitro (McMillin et al., 2010). It is suggested that the anticancer activity of SU4312 is achieved through direct inhibition of the proliferation of cancer cells and indirect suppression of angiogenesis. Moreover, the recently discovered capabilities of SU4312 to block Aβ plaque-induced vessel formation in APP23 transgenic mice, and to direct inhibit Parkinson's disease (PD)-associated leucine rich repeat kinase 2 (LRRK2) autophosphorylation highlight its potential to be developed for the treatment of neurodegenerative disorders (Lee et al., 2010; Schultheiss et al., 2006)

SU5416 ((3Z)-3-[(3,5-dimethyl-1H-pyrrol-2-yl)methylidene]-1,3-dihydro-2H-indol-2-one) was originally designed as a potent and selective inhibitor of vascular endothelial growth factor receptor-2 (VEGFR-2) for cancer therapy (Sun et al., 1998). It occupies the ATP binding site of VEGFR-2, and thereby abolishes vascular endothelial growth factor (VEGF) signaling (Sun et al., 1998). In the pre-clinical studies, SU5416 inhibits VEGF-dependent angiogenesis both in vitro and in vivo (Fong et al., 1999). As the first VEGFR-2 inhibitor evaluated in clinical trial, SU5416 is well tolerated even at the concentration of 145 $mg/m^2$ in patients with advanced malignancies in phase I clinical study (Stopeck et al., 2002). It was found that SU5416 and 5-fluorouracil-leucovorin in combination showed better efficacy than standard 5-fluorouracil-leucovorin therapy in the pilot phase I/II study (Ye et al., 2006). Nevertheless, test on this drug was discontinued for there were no significant clinical benefits in a randomized phase III trial (Shawver et al., 2002). Notably, SU5416 could be rapidly distributed to all organs, and accumulated in orthotopically implanted central nerve system (CNS) tumor model and in patients with refractory pediatric CNS tumors, suggesting that SU5416 could be delivered to the CNS by passing through the blood-brain barrier (Kieran et al., 2009).

Sunitinib (SU11248, N-(2-diethylaminoethyl)-5-[(Z)-(5-fluoro-2-oxo-1H-indol-3-ylidene)methyl]-2,4-dimethyl-1H-pyrrole-3-carboxamide) is an oral, multiple receptor tyrosine kinases (RTKs) inhibitor that was approved in U.S. for the treatment of advanced or metastatic renal cell carcinoma and imatinib-resistant gastrointestinal stromal tumors (Rock et al., 2007; Adams & Leggas, 2007). Sunitinib occupies the ATP binding sites of RTKs including vascular endothelial growth factor receptor-2 (VEGFR-2) and platelet-derived growth factor receptor (PDGFR), and thereby abolishes RTKs-mediated tumor angiogenesis and tumor cell proliferation (Blay, 2010). Clinical study has shown that daily oral administration of sunitinib lead to a plasma steady-state levels between 50 and 100 ng/ml (Desar et al., 2009). After oral administration, sunitinib could rapidly reach brain tissue (Patyna & Peng, 2006; van der Veldt et al., 2007). Moreover, sunitinib treatment has been shown safe and efficient in brain metastasis of renal cell carcinoma (Medioni et al., 2007). These results suggest that sunitinib is able to penetrate the blood brain barrier and may be used to treat central nerve system diseases (Addeo & Caraglia., 2011).

As a result of their physiological properties and proven safety for human consumption, it would be attractive for the indole-ketones or indolidones, such as SU4312, SU5416 and SU11248, to be used in preparation of drugs for the treatment of neurodegenerative diseases such as Parkinson's disease if they can be proven as NOS inhibitors. This disclosure hereby describes the uses of indole-ketones or indolidones as NOS inhibitors and drugs for treatment of neurodegenerative diseases.

SUMMARY OF THE INVENTION

In one embodiment, the present invention provides uses of indole-ketones or indolidones in preparing drugs for the treatment of neurodegenerative diseases responsive to nNOS inhibition. For example, said neurodegenerative diseases comprises any of Parkinson's disease, Alzheimer's disease, Amyotrophic lateral sclerosis, Ataxia telangiectasia, Bovine spongiform encephalopathy, Creutzfeldt-Jakob disease, Huntington's disease, Cerebellar atrophy, Multiple sclerosis, Primary Lateral Sclerosis and Spinal Muscular Atrophy.

It was demonstrated that SU4312 exhibits neuroprotection against $MPP^+$ at least partially via selective and direct inhibition of nNOS. Docking simulation revealed a possible molecular interaction between isoforms of SU4312 and nNOS. In view of the capability of SU4312 to reach the brain in rats, these results offer support for further development of SU4312 in the treatment of neurodegenerative disorders, particularly those associated with NO-mediated neurotoxicity.

It was also shown that SU5416, as well as sunitinib, possess neuroprotective potential against $MPP^+$/MPTP-induced neurotoxicity both in vitro and in vivo. It was demonstrated that neurotoxicity was prevented by reducing nNOS protein expression and directly inhibiting the enzyme activity of nNOS. In view of the capability of SU5416 and sunitinib to cross the blood-brain barrier and the safety for human use, these findings further indicate that SU5416 and sunitinib might be a novel drug candidate for neurodegenerative disorders and CNS cancers, particularly those associated with NO-mediated neurotoxicity.

In one embodiment, the present invention provides the uses of any of SU43112, SU5416, sunitinib, or their optical isomers or their salts that are capable of inhibiting nNOS in the preparation of drugs for the treatment of neurodegenerative diseases.

The present invention also provides a method of screening for candidate drug compounds for the treatment of neurodegenerative diseases. In one embodiment, the screening method involves examining the activities of monoamine oxidase-B (MAO-B) or neuronal nitric oxide synthase (nNOS) in zebrafish.

BRIEF DESCRIPTION OF THE DRAWINGS

FIG. 2 shows SU4312, but not PTK787/ZK222584, prevented $MPP^+$-induced neurotoxicity in dopaminergic neurons. (A) SU4312, but not PTK787/ZK222584, prevents $MPP^+$-induced neurotoxicity in SH-SY5Y cells. SH-SY5Y cells were treated with SU4312 or PTK787/ZK222584 at the indicated concentrations for 2 hours and then exposed to 1 mM $MPP^+$. Cell viability was measured by the MTT assay at 24 hours after $MPP^+$ challenge. (B) SU4312, but not PTK787/ZK222584, prevents $MPP^+$-induced neurotoxicity in PC12 cells. PC12 cells were treated with SU4312 or PTK787/ZK222584 at the indicated concentrations for 2 hours and then exposed to 1 mM $MPP^+$. Cell viability was measured by the MTT assay at 24 hours after $MPP^+$ challenge. Data, expressed as percentage of control, were the mean±SEM of three separate experiments; *$p<0.05$ and **$p<0.01$ versus $MPP^+$ group (ANOVA and Dunnett's test).

FIG. 7 shows SU4312 inhibited nNOS in a non-competitive manner. (A) Pattern analysis of nNOS inhibition with L-arginine by SU4312. Recombinant nNOS (2.5 µg) was assayed in either the presence (10 or 20 µM) or absence of SU4312 under the condition with 5 to 40 µM L-[3H] arginine. The plots of 1/V versus 1/[S] were fitted by a Lineweaver-Burk Straight-line with an intercept of $1/V_{max}$ and a slope of $K_m/V_{max}$. The data were expressed as the means of three independent experiments. (B) The Ki value of SU4312 in the inhibition of nNOS. The plot of the apparent $1/V_{max}$ from (A) versus concentration of SU4312 was drawn by the linear fit.

FIG. 9 shows SU4312 reached the brain after i.p. administration. (A) Plasma concentration-time profile of SU4312 in rats after i.p. administration. After 12 mg/kg SU4312 administration by i.p., serial blood samples were collected and analyzed. Data were the mean±SD (n=3). (B-F) HPLC Chromatograms of (B) standard SU4312 solution (150 µg/ml); (C) Brain homogenate extract from control rat; (D-F) Brain homogenate extract from rat at 15 min (D), 30 min (E) and 1 hour (F) after i.p. administration of SU4312 (12 mg/kg). Peak 1: cis-SU4312; Peak 2: trans-SU4312.

FIG. 12 shows SU5416 prevented $MPP^+$-induced apoptosis in a concentration-dependent manner. (A) SU5416, but not VRI, prevented $MPP^+$-induced cell death in a concentration-dependent manner. CGNs were treated with SU5416, VRI, EPTU, 7-nitroindazole (7-NI), 1400W or DMSO (vehicle control) at the indicated concentrations for 2 hours and then exposed to 35 µM $MPP^+$. Cell viability was measured by MTT assay at 24 hours after $MPP^+$ challenge. (B) SU5416 blocked neuronal loss induced by $MPP^+$. CGNs were pre-incubated with or without 20 µM SU5416 and exposed to 35 µM $MPP^+$ 2 hours later. At 24 hour after $MPP^+$ challenge, CGNs were assayed with FDA/PI double staining. (C) SU5416 reversed the morphological alteration induced by $MPP^+$. CGNs were pre-incubated with or without 20 µM SU5416 and exposed to 35 µM $MPP^+$ 2 hours later. At 24 hour after $MPP^+$ challenge, CGNs were assayed with nNOS and Hoechst double staining. (D) The number of apoptotic nuclei with condensed chromatin was counted from representative Hoechst staining photomicrographs and represented as a percentage of the total number of nuclei counted. Data, expressed as percentage of control, were the mean±SEM of three separate experiments; *p<0.05 and **p<0.01 versus $MPP^+$ group in (A) or versus control in (D); ##p<0.01 versus $MPP^+$ group in (D) (Turkey's test).

FIG. 14 shows SU5416 increased the number of dopaminergic neurons in MPTP-treated zebrafish larval. One dpf zebrafish embryos were co-incubated with 200 µM MPTP and 1 µM SU5416 or 0.3% DMSO (vehicle control) for 2 days. After treatment, zebrafish were collected to perform paraffin-embedding, sectioning and immunostaining. (A) Representative picture of immunostaining of zebrafish section. (B) Statistical analysis of the number of TH-positive neurons in each treatment group (n=12 fish/group). *p<0.05 versus MPTP group (Turkey's test)

FIG. 21 shows Sunitinib blocks low potassium-induced neuronal apoptosis and NO over-production in cerebellar granule neurons (CGNs). (A) Sunitinib, but not PTK787, prevented low potassium-induced cell death in a concentration-dependent manner. At 8 day in vitro, CGNs were switched to the 5 mM KCl BME medium containing sunitinib, PTK787, L-NMMA or DMSO (vehicle control). Cell viability was measured by MTT assay at 24 hours after low potassium challenge. (B) Sunitinib blocked neuronal loss induced by low potassium in CGNs. CGNs were switched to the 5 mM KCl BME medium with or without 1.5 μM sunitinib. After 24 hours of low potassium challenge, CGNs were assayed with an FDA/PI double staining. (C) Sunitinib reversed the morphological alteration induced by low potassium in CGNs. CGNs were switched to the 5 mM KCl BME medium with or without 1.5 μM sunitinib. After 24 hours of low potassium challenge, CGNs were assayed with Hoechst staining. The number of apoptotic nuclei with condensed chromatin were counted from representative Hoechst staining photomicrographs and represented as a percentage of the total number of nuclei counted. (D) Sunitinib reversed the elevated intracellular NO induced by low potassium in CGNs. CGNs were switched to the 5 mM KCl BME medium containing 1.5 μM sunitinib, 10 μM L-NMMA or DMSO (vehicle control). Intracellular NO level was measured using DAF-FM diacetate as a probe at 4 hour after low potassium challenge. Data, expressed as percentage of control (CGNs were cultured in high potassium medium), were the mean±SEM of three separate experiments; *$p<0.05$ and **$p<0.01$ versus low potassium group in (A) and (D) or versus control in (C); $^{\#\#}p<0.01$ versus low potassium group in (C) (Turkey's test).

DETAILED DESCRIPTION OF THE INVENTION

Figure 1:
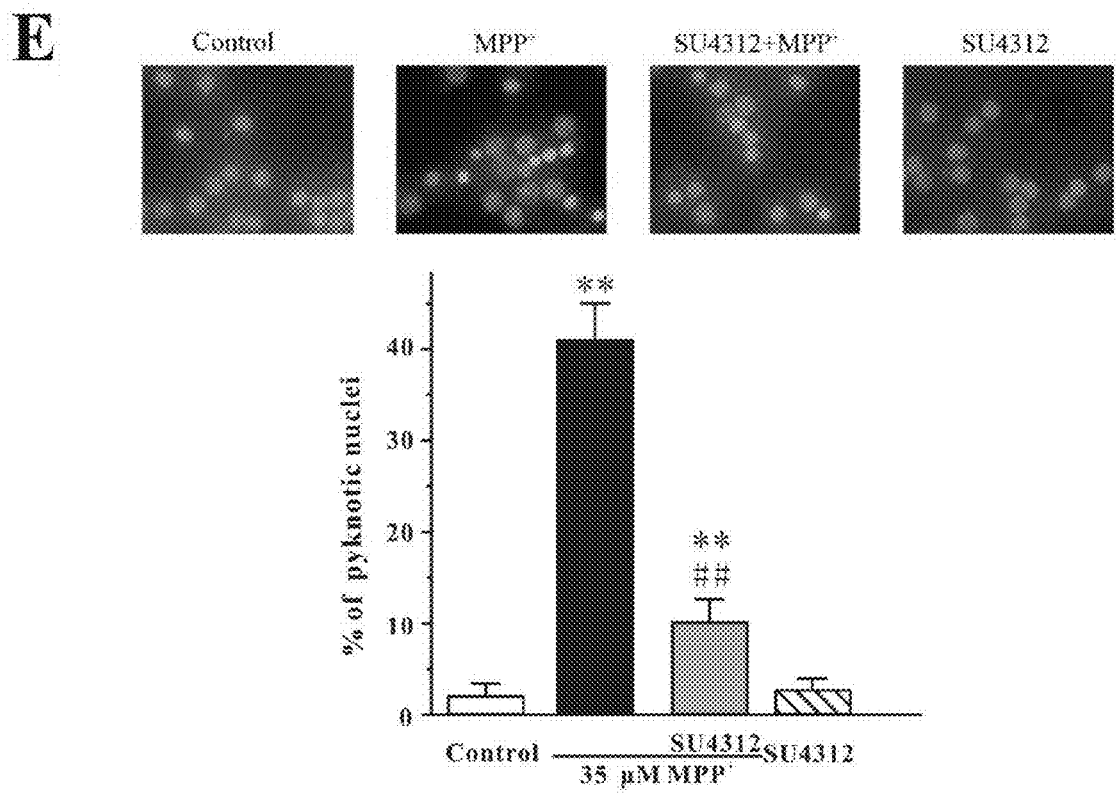
FIG. 1 shows SU4312 prevented $MPP^+$-induced apoptosis in a concentration-dependent manner. CGNs were treated with SU4312 and/or PTK787/ZK222584 at the indicated concentrations for 2 hours and then exposed to 35 µM $MPP^+$. Cell viability (A) and cytotoxicity (B) were measured at 24 hours after $MPP^+$ challenge by MTT and LDH assays, respectively. (C) CGNs were co-administrated SU4312 or PTK787/ZK222584 with 35 µM $MPP^+$. Cell viability was measured at 24 hours after $MPP^+$ challenge by MTT assay. (D) SU4312 blocks neuronal loss and reverses the morphological alterations induced by $MPP^+$. CGNs were pre-incubated with or without 20 µM SU4312 and exposed to 35 µM $MPP^+$ 2 hours later. At 24 hour after the $MPP^+$ challenge, CGNs were assayed with FDA/PI double staining. (E) SU4312 blocks $MPP^+$-induced neuronal apoptosis. CGNs were exposed to 35 µM $MPP^+$ for 24 hours with or without pre-treatment of 20 µM SU4312 for 2 hours. The neurons were then performed by Hoechst 33342 staining assay. The number of pyknotic nuclei with condensed chromatin was counted from representative photomicrographs and represented as a percentage of the total number of nuclei counted. Data, expressed as a percentage of the control, were the mean±SEM of three separate experiments; *$p<0.05$ and **$p<0.01$ versus $MPP^+$ group in (A), (B), and (C), or versus control in (E); ###$p<0.01$ versus $MPP^+$ group in (E) (Turkey's test).

This invention provides uses of indole-ketones or indolidones in the preparation of drugs for treatment of neurodegenerative diseases. It will be appreciated by persons skilled in the art that the uses of indole-ketones or indolidones disclosed herein may be used for the treatment of Parkinson's disease but its application could be extended to any neurodegenerative disease which can be treated, alleviated or prevented by inhibition of neuronal nitric oxide synthase.

The data presented herein indicate that SU4312/5416/11248 blocked neuronal loss and reversed the morphological alterations induced by MPP⁺, implying there is a reversal of neuronal loss. Presumably, besides stopping neuronal loss or apoptotic actions of MPP⁺, the indole-ketones or indolidones could also induce replacement of loss neurons and connections.

The data presented herein show that the nNOS inhibition action of indole-ketones, as illustrated by SU4312, is mediated by blocking catalysis in the "binding pocket" by the $N(CH_3)_2$ (N,N-dimethyl aniline) group of SU4312 interacting with nNOS $NH_2^+$ of Pro565 and/or Pro565 and Arg596, and the NH of SU4312 interacting with the COO— of the nNOS heme group. One of ordinary skill in the art would readily utilize these results in the study and design of nNOS inhibitor for the treatment of neurodegenerative disease or disorder.

As used herein, indole-ketones or indolidones is used as that term is commonly understood in the art. In general, the term "indolidones" refers to a large subclass of substituted or unsubstituted compounds that are capable of being synthesized from an aldehyde moiety and an oxindole moiety. In one embodiment, the indole-ketones or indolidones include indirubin, indirubin-3-oxime and derivatives such as 6-bromoindirubin-3'-oxime and indirubin-5-nitro-3'-oxime. Descriptions of indole-ketones or indolidones and their derivatives are readily available in the art, see e.g. U.S. Pat. Nos. 6,573,293, 7,125,905; U.S. Patent Application Publication Nos. 20120258995, 20070010569, and 20100331327; and CN101023944.

In one embodiment, the present invention provides a method of treating or preventing a neurodegenerative disease or disorder, the method comprises administering to a subject in need thereof an effective amount of a pharmaceutical composition comprising indole-ketone or indolidone. In general, the subject is a vertebrate, a mammal or human. In one embodiment, the concentration of said indole-ketone or indolidone is about 0.3-30 μM.

The present invention also provides uses of indole-ketone or indolidone in the preparation of medicament for the treatment or prevention of neurodegenerative disease or disorder.

In one embodiment, the neurodegenerative disease or disorder is associated with excessive neuronal Nitric Oxide Synthase (nNOS) activity. In another embodiment, the neurodegenerative disease or disorder has one or more symptoms of cognitive function degeneration, movement function degeneration, neuronal loss, neuronal synaptic dysfunction, excessive monoamine oxidase-B activity, lack of tyrosine hydroxylase activity, excessive deposition of proteins as fibers or plaques extra- or intra-cellularly, mitochondrial dysfunction, and/or neural inflammation.

In one embodiment, the neurodegenerative disease or disorder is Parkinson's Disease (PD), PD-associated Alzheimer's Disease or other PD-associated neurodegenerative disease.

In another embodiment, the neurodegenerative disease or disorder is Parkinson' Disease in combination with major symptoms from other neurodegenerative diseases such as Alzheimer's Disease, Huntington Disease, Multiple Sclerosis, and Amyotrophic Lateral Sclerosis, etc.

In one embodiment, a pharmaceutical composition comprising indole-ketone SU4312, its optical isomers or salts, or its derivatives is administered to the subject. In another embodiment, a pharmaceutical composition comprising indole-ketone SU5416, its optical isomers or salts, or its derivatives is administered to the subject. In yet another embodiment, a pharmaceutical composition comprising indole-ketone SU11248 (Sunitinib), its optical isomers or salts, or its derivatives is administered to the subject. Descriptions for indole-ketones or indolidones and their derivatives are readily available in the art, see e.g. U.S. Pat. Nos. 6,573,293, 7,125,905; U.S. Patent Application Publication Nos. 20120258995, 20070010569, and 20100331327; and CN101023944; see also Rodamer et al. (2011). In one embodiment, the present invention also provides a composition effective in treating or preventing a neurodegenerative disease or disorder, said composition comprises indole-ketones or indolidones. In one embodiment, the concentration of said indole-ketone or indolidone is about 0.3-30 μM.

One of ordinary skill in the art would readily determine the route and dosage of administration for the pharmaceutical composition comprising indole-ketones or indolidones. In one embodiment, the pharmaceutical composition is administered in combination with other compounds to achieve synergistic treatment or prevention of the multi-symptomic neurodegenerative disease or disorder.

In another embodiment, the indole-ketones or indolidones are delivered to target cells using one of many delivery vehicles known in the art, e.g. stem cells, induced pluripotent cells (iPSC), mesenchymal stem cells (MSC), bacterial ghosts or mini-cells, nano-encapsulated particles, or liposomes.

In another embodiment, the pharmaceutical composition can be administered via one of the routes generally used in the art; for example, oral, nasal, otic, ocular, sublingual, buccal, systemic, cerebral spinal fluid injection, transdermal, and mucosal.

One of ordinary skill in the art would readily formulate the indole-ketones or indolidones for pharmaceutical administration. For example, the indole-ketones or indolidones can be formulated in the form of tablets, granules, injection, powder, solution, suspension, sprays, patches or capsules. In one embodiment, the present invention includes formulations of indole-ketones or indolidones effective in treating or preventing a neurodegenerative disease or disorder. In one embodiment, the concentration of said indole-ketone or indolidone is about 0.3-30 μM.

Data presented herein show that in cells of neurodegenerative subjects or models, the function or expression of certain gene or enzyme were expressed at 40-55% of the normal level. After exposing such cells to the candidate drugs, such as those described herein, the function or expression of the deficient gene was restored to at least 60-80% of the normal level, with up to 40% pyknotic nuclei reduces to 10%. Example of deficient gene includes tyrosine hydroxylase. One the other hand, there are genes that were over-expressed 1.5 to 3 folds higher than normal, and treatment with candidate drugs would reduce such level to 1-1.5 fold of normal. Examples of over-expressed gene include monoamine oxidase-B and neuronal nitric oxide synthase. Data below also show that for neurotoxic insulted cells or animals, the survival rate after treatment may increase from 15% to 55%.

Accordingly, the present invention also provides a method of using indole-ketone or indolidone to modulate the function or enzymatic activities in neurodegenerative disease cells, wherein contacting cells with said indole-ketone or indolidone would result in one or more of the following: decrease the function or expression of monoamine oxidase-B; decrease the function or expression of neuronal nitric oxide synthase; increase the function or expression of tyrosine hydroxylase; and increase movement of the cells. In one embodiment, the cells are obtained from a subject having Parkinson's Disease (PD), PD-associated Alzheimer's Disease or other PD-associated neurodegenerative disease. The present invention also provides a composition effective in modulating the function or enzymatic activities in neurodegenerative disease cells, said composition comprises indole-ketones or indolidones. In one embodiment, the concentration of said indole-ketone or indolidone is about 0.3-30 µM.

The present invention also provides a method of screening for a candidate compound for the treatment of a neurodegenerative disease, comprising the steps of contacting the candidate compound with a population of cells; and examining the function or expression of one or more of: neuronal nitric oxide synthase (nNOS), vascular endothelial growth factor receptor-2 tyrosine kinase (VEGFR-2 TK), neurotoxic protection, mitochondrial function, monoamine oxidase-B (MAO-B), tyrosine hydroxylase, and movement functions in said cells, wherein changes in the function or expression of the above in the presence of said candidate compound as compared to a control compound indicates that said candidate compound is useful for the treatment of a neurodegenerative disease. In one embodiment, the function or expression of MAO-B or nNOS is decreased in the presence of said candidate compound, or the function or expression of tyrosine hydroxylase is increased in the presence of said candidate compound. Examples of neurodegenerative diseases include, but are not limited to, Parkinson's disease, Alzheimer's disease, Amyotrophic lateral sclerosis, Ataxia telangiectasia, Bovine spongiform encephalopathy, Creutzfeldt-Jakob disease, Huntington's disease, Cerebellar atrophy, Multiple sclerosis, Primary Lateral Sclerosis and Spinal Muscular Atrophy. In one embodiment, the screening method is performed in cells obtained from zebrafish. In another embodiment, the screening method is performed in vitro or in vivo. In yet another embodiment, the present invention includes candidate compounds for the treatment of a neurodegenerative disease as screened by the method described above.

The invention will be better understood by reference to the Experimental Details which follow, but those skilled in the art will readily appreciate that the specific examples are for illustrative purposes only and should not limit the scope of the invention which is defined by the claims which follow thereafter. It is to be noted that the transitional term "comprising", which is synonymous with "including", "containing" or "characterized by", is inclusive or open-ended and does not exclude additional, un-recited elements or method steps.

Example 1

Neuroprotection by SU4312

1.1) Materials and Methods
1.1.1) Primary Cerebellar Granule Neuron Culture

All animal experiments were conducted according to the ethical guidelines of ICMS, Macau University and the Animal Care Facility, The Hong Kong Polytechnic University. Rat CGNs were prepared from 8-day-old Sprague-Dawley rats (The Animal Care Facility, The Hong Kong Polytechnic University) as described by Li et al., 2005. Briefly, neurons were seeded at a density of $2.7 \times 10^5$ cells/ml in basal modified Eagle's medium (Invitrogen) containing 10% fetal bovine serum, 25 mM KCl, 2 mM glutamine, and penicillin (100 units/ml)/streptomycin (100 µg/ml). Cytosine arabinoside (10 µM) was added to the culture medium 24 hour after plating to limit the growth of non-neuronal cells. With the use of this protocol, more than 95% of the cultured cells were granule neurons.

1.1.2) Cell Lines Culture

The human neuroblastoma SH-SY5Y cells were obtained from ATCC. The cells were maintained in supplemented Dulbecco's modified eagle medium (DMEM), 10% fetal bovine serum, 100 U/ml penicillin, and 100 µg/ml streptomycin in a 37° C., 5% CO2 incubator. PC12 pheochromocytoma cells were also obtained from ATCC. The cells were cultured in medium that consisted of DMEM, 10% heat-inactivated horse serum, 5% fetal bovine serum, 100 U/ml penicillin, and 100 µg/ml streptomycin in a 37° C., 5% CO2 incubator. All experiments were carried out 48 hours after the cells were seeded.

1.1.3) Measurement of Neurotoxicity

The percentage of surviving neurons in the presence of SU4312 and/or MPP$^+$ was estimated by determining the activity of mitochondrial dehydrogenases with 3(4,5-dimethylthiazol-2-yl)-2.5-diphenyltetrazolium bromide (MTT) assay (Li et al., 2007). The assay was performed according to the specifications of the manufacturer (MTT kit I; Roche Applied Science). Briefly, the neurons were cultured in 96-well plates, 10 µl of 5 mg/ml MTT labeling reagent was added to each well containing cells in 100 µl of medium, and the plates were incubated for 4 hours in a humidified incubator at 37° C. After the incubation, 100 µl of the solvating solution (0.01 N HCl in 10% SDS solution) was added to each well for 16-20 hours. Absorbance of the samples was measured at a wavelength of 570 nm with 655 nm as a reference wavelength. Unless otherwise indicated, the extent of MTT conversion in cells exposed to MPP$^+$ is expressed as a percentage of the control.

Cytotoxicity was determined by measuring the release of lactate dehydrogenase (LDH). Briefly, cells were precipitated by centrifugation at 500 g for 5 min at room temperature, 50 µl of the supernatants was transferred into new wells, and LDH was determined using the in vitro toxicology assay kit (Roche). The absorbance of the samples was measured at a wavelength of 490 nm with 655 nm as a reference wavelength.

1.1.4) FDA/PI Double Staining Assay

Viable granule neurons were stained with fluorescein formed from fluorescein diacetate (FDA), which is de-esterified only by living cells. Propidium iodide (PI) can penetrate cell membranes of dead cells to intercalate into double-stranded nucleic acids. Briefly, after incubation with 10 µg/ml FDA and 5 µg/ml PI for 15 min, the neurons were examined and photographed using UV light microscopy; and the pictures were compared with those photographed under phase contrast microscopy.

1.1.5) Hoechst Staining Assay

Chromatin condensation was detected by nucleus staining with Hoechst 33342 as described by Li et al., 2005. CGNs ($2.7 \times 10^6$ cells) grown in a 35-mm dish were washed with ice-cold phosphate-buffered saline (PBS) and fixed with 4% formaldehyde in PBS. The cells were then stained with Hoechst 33342 (5 µg/ml) for 5 min at 4° C. The nuclei were visualized using a fluorescence microscope at ×400 magnification.

1.1.6) Measurement of Intracellular NO

Intracellular NO was monitored with 4-Amino-5-methyl-amino-2',7'-difluorofluorescein (DAF-FM) diacetate, a pH-insensitive fluorescent dye that emits increased fluorescence after reaction with an active intermediate of NO formed during the spontaneous oxidation of NO to $NO_2$ (Sheng et al., 2005). DAF-FM solution was added to the culture medium (final concentration: 5 μM). After 30 min in a $CO_2$ incubator, cultures were washed twice with PBS and incubated for an additional 30 min to allow complete de-esterification of the intracellular diacetate for stronger fluorescence. The DAF-FM fluorescence in CGNs was quantified by a multi-detection microplate reader using excitation and emission wavelengths of 495 nm and 515 nm, respectively. The measured fluorescence values were expressed as a percentage of the fluorescence in the control cells.

1.1.7) Maintenance of Zebrafish and Drug Treatment

Wild-type zebrafish (AB strain) and Tg (fli-1:EGFP) transgenic zebrafish were maintained as described in the Zebrafish Handbook (Westerfield, 1993). Zebrafish embryos were generated by natural pair-wise mating (3-12 months old) and raised at 28.5° C. in embryo medium (13.7 mM NaCl, 540 μM KCl, pH 7.4, 25 μM $Na_2HPO_4$, 44 μM $KH_2PO_4$, 300 μM $CaCl_2$, 100 μM $MgSO_4$, 420 μM $NaHCO_3$, pH 7.4). Drugs were dissolved in DMSO and directly added into the zebrafish embryo medium to treat fish in 2-3 days (Final concentration of DMSO was always less than 0.5%, and showed no toxicity to zebrafish). An equal concentration of DMSO in embryo medium was used as vehicle control in each experiment.

1.1.8) Exposure to MPTP

Healthy zebrafish embryos were picked out and dechlorinated manually at 1 day post fertilization (dpf) and distributed into a 12-well plate with 20 fish embryos or a 6-well microplate with 30 fish embryos in each well. In pilot experiments, several doses of MPTP were added to the embryo medium (final concentration from 50 to 800 μM) and treated 1 dpf fish embryo for 48 hours, the optimal dose used (200 μM) induced significantly decreases in brain diencephalic DA neurons and without any detectable systematic toxicities (data not shown). Thus subsequent studies were done with 200 μM MPTP for whole-mount immunostaining and gene expression experiments.

As late as 3 dpf, zebrafish larvae showed very little spontaneous swimming but by 5 dpf, they spontaneously swam longer distances and independently searched for food. Thus the MPTP exposure needs to last 5 day from 1 dpf. In pilot locomotion behavioral test, treatment for 3 days starting from 1 dpf with 200 μM MPTP in embryo medium killed all the fish larvae, however, after treatment for 2 days at 1 dpf with 200 μM MPTP and drug withdraw for 3 days, the deficit behavior was recovered at 6 dpf. Finally, the optimal MPTP exposure was at 3 dpf, 2 days after treatment starting from 1 dpf with 200 μM MPTP, zebrafish larvae were maintained in embryo medium containing 10 μM MPTP for another 3 days, the swimming distance significantly decreased without any detectable systematic toxicities. Thus subsequent locomotion behavioral studies were done with 200 μM MPTP for treatment for 2 days at 1 dpf then replacing insult with 10 μM MPTP for incubation for another 3 days.

1.1.9) Whole-Mount Immunostaining with Antibody Against Tyrosine Hydroxylase

Whole-mount immunostaining in zebrafish was performed as previously described by Zhang et al., 2011. Briefly, zebrafish were fixed in 4% paraformaldehyde in PBS for 5 hours. Fixed samples were blocked (2% lamb serum and 0.1% BSA in PBST) for 1 hour at room temperature. A mouse monoclonal anti-tyrosine hydroxylase antibody (Millipore, USA) was used as the primary antibody and incubated with samples overnight at 4° C. On the next day, samples were washed 6 times with PBST (each wash lasted 30 min), followed by incubation with secondary antibody according to the instruction provided by the Vectastain ABC kit (Vector Laboratories, USA). After staining, zebrafish were flat-mounted with 3.5% methylcellulose and photographed. Semi-quantification of area of $TH^+$ cells were assessed by an investigator blinded to drug treatment history of zebrafish using Image-Pro Plus 6.0 software (Media Cybernetics, Silver Spring, Md., USA). Results are expressed as percentage of area of $TH^+$ cells in untreated normal control group.

1.1.10) Morphological Observation of Zebrafish

After drug treatment, zebrafish were removed from microplate and observed for gross morphological changes of blood vessel under a fluorescence microscope (Olympus am Motorized Inverted Microscope, Japan) equipped with a digital camera (DP controller, Soft Imaging System, Olympus). Images were analyzed with Axiovision 4.2 and Adobe Photoshop 7.0.

1.1.11) Locomotion Behavioral Test of Zebrafish

After drug treatment, zebrafish larvae at 6 dpf were transferred into 96-well plates (1 fish/well and 12 larvae/group). Fishes responded with excessive stress reaction (such as rapid and disorganized swimming or immobility for 2 min) due to the handling and monitoring of the behavior were discarded. The experiments were performed in a calm enclosed area. The larvae were allowed to habituate to the new environment for 30 min prior to experiments. Behavior was monitored by an automated video tracking system (Viewpoint, ZebraLab, LifeSciences). The 96-well plates and camera were housed inside a Zebrabox and the swimming pattern of each fish was recorded for 10 min and repeated 3 times, once every other 10 min. The total distance moved was defined as the distance (in cm) that the fish had moved during one session (10 min).

1.1.12) Total RNA Extraction, Reverse Transcription, and Real-Time PCR

Total RNA was extracted from 30 zebrafish larvae of each treatment group using the RNeasy Mini Kit (Qiagen, USA) according to the manufacturer's instructions. RNA was reverse transcribed to single-strand cDNA using SuperScript™ III First-Strand Synthesis System for RT-PCR (Invitrogen™, USA), followed by real-time PCR using the TaqMan Universal PCR Master Mix and 2 μL TaqMan gene expression assay primers for the zebrafish th gene (assay ID:Dr03437803_g1, Applied Biosystems, USA) in the ABI 7500 Real-Time PCR System (Applied Biosystems). The expression of the mRNA was normalized to the amount of bactin1 using the relative quantification method described by the manufacturer. The zebrafish bactin1 primers (Applied Biosystems, USA) were

```
                                          (SEQ ID NO: 1)
    5'-CAAGATTCCATACCCAGGAAGGA-3' (F)
    and (SEQ ID NO: 2)
    5'- CAACGGAAACGCTCATTGC -3' (R)
```

1.1.13) NOS Activity Assays

In the in vitro NOS activity assay (Li et al., 2007), purified recombinant human nNOS, endothelial NOS (eNOS), and inducible NOS (iNOS) were bought from Alexis Biochemicals (Lausen, Switzerland). NOS activity was determined by monitoring the conversion of L-[3H]arginine to [3H]citrulline following the instructions provided in the kit (Calbiochem, USA). The reaction mixture contained a final volume of 40 μl with 25 mM Tris-Cl at pH 7.4, 3 μM tetrahydrobiopterin, 1 μM FAD, 1 μM FMN, 1 mM NADPH, 0.6 mM CaCl$_2$, 0.1 μM calmodulin, 2.5 μg of pure NOS enzyme, 5 μl L-[3H]arginine (Perkin Elmer, Waltham, Mass., USA), and different concentrations of the tested reagents. The reaction mixture was incubated at 22° C. for 45 min. The reaction was quenched by adding 400 μl of stopping buffer (50 mM HEPES, pH 5.5, and 5 mM EDTA) for nNOS and eNOS reactions or by heating reactive tubes for iNOS. Unreacted L-[3H]arginine was then trapped by 100 μl of equilibrated resin provided in a spin cup followed by centrifugation for 30 s at 13,200 rpm. The filtrate was quantified by liquid scintillation counting.

1.1.14) Molecular Docking

Molecular docking was performed using the ICM-Pro 3.6-1d program (Molsoft) (Totrov & Abagyan, 1997). According to the ICM method, the molecular system was described using internal coordinates as variables. The biased probability Monte Carlo (BPMC) minimization procedure was used for global energy optimization. The BPMC global energy optimization method consists of the following steps: (1) a random conformation change of the free variables according to a predefined continuous probability distribution; (2) local energy minimization of analytical differentiable terms; (3) calculation of the complete energy including non-differentiable terms such us entropy and solvation energy; and (4) acceptance or rejection of the total energy based on the Metropolis criterion and return to Step 1. A series of five grid potential representations of the receptor were automatically generated and superimposed that accounted for the hydrophobicity, carbon-based and hydrogen-based van der Waals boundaries, hydrogen-bonding profile, and electrostatic potential. The binding between SU4312 and NOS protein (PDB code for nNOS: 3NLV; PDB code for eNOS: 3NOS; and PDB code for iNOS: 1VAF) was evaluated by a binding score that reflected the quality of the complex. ICM docking was performed to find out the most favorable orientation. The resulting SU4312 and NOS protein complex trajectories were energy minimized, and the scores were computed.

1.1.15) Determination of SU4312 in the Brain Homogenate and Plasma

To investigate whether SU4312 could reach the brain, an HPLC method was used to detect SU4312 in the brain homogenate and plasma of rats (Scott et al., 2004; Spitsin et al., 2008). Briefly, after drug administration by i.p., the animals were transcardially perfused with PBS/heparin (1000 U/L). Then rats were sacrificed by decapitation and brain tissue was homogenized. SU4312 in the brain homogenate was extracted with 3 ml acetyl acetate. After evaporating the solvent, the residue was reconstituted in 50 μl methanol. SU4312 in the brain tissue was identified by an Agilent 1200 Series HPLC coupled with UV detector at a wavelength of 254 nm. Prior to the preparation of brain homogenate, transcardial perfusion with PBS/heparin was conducted in order to remove blood from cerebravascular system so as to avoid the interference of the SU4312 that simply retained in the brain vasculature.

Plasma concentration of SU4312 was also assayed by an HPLC method. Briefly, after drug administration by i.p., serial blood samples were collected through right internal jugular vein catheterization at various time points postdosing. The plasma samples were treated with acetonitrile and methanol followed by centrifugation, and 20 μl supernatants were injected into the liquid chromatographic system. The mobile phase consisted of a mixture of methanol and water (80:20, v/v) at a flow rate of 1 ml/min.

1.1.16) MAO-B Inhibition Activity of SU4312

The MAO-B inhibition activity of SU4312 was determined by MAO-Glo™ Assay kit (Promega Inc., USA). The recombinant human MAO-B enzymes and selegiline used in this study were purchased from Sigma-Aldrich. Concentrations of SU4312 tested were 0.01, 0.03, 0.1, 0.3, 1.0 and 10 μM. Selegiline, a known MAO-B inhibitor, was used as positive control at 0.001, 0.01, 0.1, 1, 10 μM. Briefly, SU4312 and selegiline were incubated in 96-well opaque white plates with MAO substrate and rhMAO-B (0.25 mg protein/mL final concentration). Reactions were started by addition of rhMAO-B. Samples were incubated for 1 hour at room temperature. Reactions were terminated by addition of luciferin detection reagent, and samples were incubated an additional 20 minutes to allow development of luciferase- and esterase-dependent luminescence. Relative luminescence was determined with a plate luminometer and was corrected for background using no-MAO-B controls. Results are presented as percent of vehicle (total MAO-B activity).

1.1.17) Data Analysis and Statistics

The data are expressed as the means±SEM, and statistical significance was determined by analysis of variance with Dunnett's test in the case of multiple comparisons with control or Tukey-Kramer means separation test for multiple comparisons among the treatment groups. Differences were accepted as significant at $p<0.05$.

1.1.18) Materials

SU4312, MPP$^+$ and MPTP were obtained from Sigma-Aldrich (Germany). PTK787/ZK222584 was purchased from LC laboratories (USA). 7-nitroindazole, 1400W, PBITU was from Calbiochem (USA).

1.2) Results 1.2.1) SU4312 but not PTK787/ZK222584 unexpectedly prevents MPP$^+$-induced neuronal death in a concentration-dependent manner.

At 8 days in vitro (DIV), CGNs were pre-treated with gradually increased concentrations of SU4312 (1, 3, 10, 20 and 30 μM) for 2 hours and then treated with 35 μM MPP$^+$ for 24 hours. Cell viability was measured using the MTT and LDH assays. It was found that SU4312 unexpectedly prevented MPP$^+$-induced cell death in a concentration-dependent manner (FIGS. 1A and 1B). However, SU4312 itself did not affect cell proliferation or show any cytotoxic effects at the experimental concentrations (1-30 μM) for 26 hours (data not shown). For comparison, PTK787/ZK222584 (VATALANIB®), another specific VEGFR-2 inhibitor, was also tested in this model. PTK787/ZK222584 at 3-10 μM failed to block neuronal loss in vitro (FIGS. 1A and 1B). Moreover, SU4312 and PTK787/ZK222584 co-application did not significantly affect the neuroprotection of SU4312 against MPP$^+$ in CGNs, suggesting that the neuroprotective effects of SU4312 might be independent of VEFGR-2 inhibition (FIGS. 1A and 1B).

Co-administration experiments were performed and it was found that SU4312 (10-20 μM) still had neuroprotective effects against MPP$^+$-induced neurotoxicity when it was co-administrated with 35 μM MPP$^+$ (FIG. 1C). However, in the same condition, PTK787/ZK222584 at 10 μM did not show neuroprotective effects (FIG. 1C).

For microscopy-based analysis of apoptosis, CGNs were pretreated with 20 μM SU4312 for 2 hours and then exposed to 35 μM MPP$^+$. Phase contrast microscopy and FDA/PI double staining assay showed that SU4312 significantly blocked MPP$^+$-induced loss of neurons and reversed MPP$^+$-induced morphological alterations, including unhealthy bodies and broken extensive neuritic network (FIG. 1D). In addition, staining of pyknotic nuclei by Hoechst 33342 showed that SU4312 significantly reversed nuclear condensation induced by MPP$^+$ (FIG. 1E).

To further investigate the neuroprotective effects of SU4312 in dopaminergic neurons, the two commonly used in vitro models of dopaminergic neurons for PD, SH-SY5Y cells and PC12 cells, were used. SH-SY5Y or PC12 cells were pre-treated with gradually increasing concentrations of SU4312 for 2 hours and then treated with 1 mM MPP$^+$ for 24 hours. Cell viability was measured using the MTT assay. SU4312 prevented MPP$^+$-induced dopaminergic neuronal death at 3-10 μM in SH-SY5Y cells, and at 10 μM in PC12 cells (FIG. 2). PTK787/ZK222584 was also tested in the same models. PTK787/ZK222584 at 3 μM failed to block neuronal loss induced by MPP$^+$ in both SH-SY5Y cells and PC12 cells (FIG. 2). The treatment with 10 μM SU4312 or 3 μM PTK787/ZK222584 alone for 26 hours did not show cell proliferative or cytotoxic effects (data not shown). However, SU4312 and PTK787/ZK222584 at higher concentration conferred toxicity to both SH-SY5Y cells and PC12 cells (data not shown).

1.2.2) SU4312 but not PTK787/ZK222584 Unexpectedly Prevents MPTP-Induced Neurotoxicity in Zebrafish.

Figure 3:
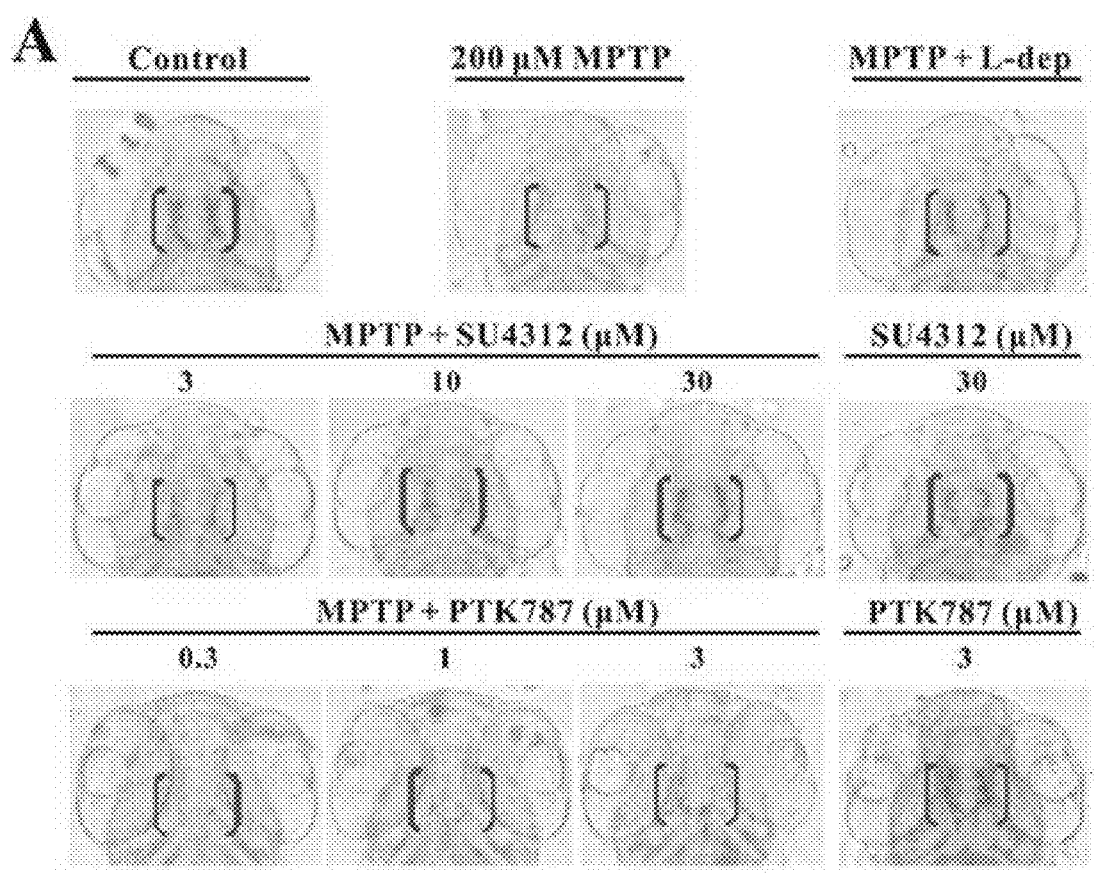
FIG. 3 shows SU4312 protected MPTP-induced neurotoxicity in zebrafish. One dpf zebrafish embryos were co-incubated with 200 µM MPTP and SU4312 or PTK787/ZK222584 at the indicated concentrations for 48 hours, and zebrafish embryos that had been co-treated with MPTP and 100 µM L-deprenyl (L-dep, a monoamine oxidase B inhibitor) were used as the positive control. After treatment, zebrafish were collected to perform immunohistochemistry, or total RNA extraction and real-time quantitative PCR. (A, B) SU4312, but not PTK787/ZK222584, prevents MPTP-induced $TH^+$ neuronal loss in the brain of zebrafish in a concentration-dependent manner. (A) Representative pictures of DA neurons in the zebrafish brain from different treatment groups. Immunohistochemistry was performed with anti-TH primary antibody, and $TH^+$ neurons in the diencephalic area of the zebrafish brain, which were indicated by red bracket, were considered as DA neurons. (B) Statistic analysis of $TH^+$ neurons in each treatment group, 20 fish embryos per group from 3-time independent experiments. Values were expressed as a percentage of the control. (C) SU4312, but not PTK787/ZK222584, reverses th gene expression down-regulated by MPTP. Data were expressed as relative fold change of control ($log_2$), *$p<0.05$ and **$p<0.01$ versus MPTP group; #$p<0.05$ and ###$p<0.01$ versus control (Turkey's test).

To test the neuroprotective effect of SU4312 and PTK787/ZK222584 in vivo, zebrafish embryos at 1 dpf were exposed to 200 μM MPTP for 2 days, the DA system in the brain of the zebrafish was determined by immunostaining of TH with specific antibody and analysis of the gene expression by quantitative PCR. After MPTP treatment, ventral diencephalic TH populations which are highly sensitive to MPTP exposure, were included in the analysis (Wen et al., 2008). The number of DA neurons in the diencephalons of zebrafish (indicated by red bracket) decreased dramatically (FIG. 3A), and the level of th gene expression was significantly downregulated (FIG. 3C). SU4312 significantly alleviated the loss of DA neurons and decrease of th gene expression in a concentration-dependent manner. In contrast, PTK787/ZK222584 (0.3-3 μM) could not prevent MPTP-induced DA neuronal loss in the zebrafish (FIG. 3).

Figure 4:
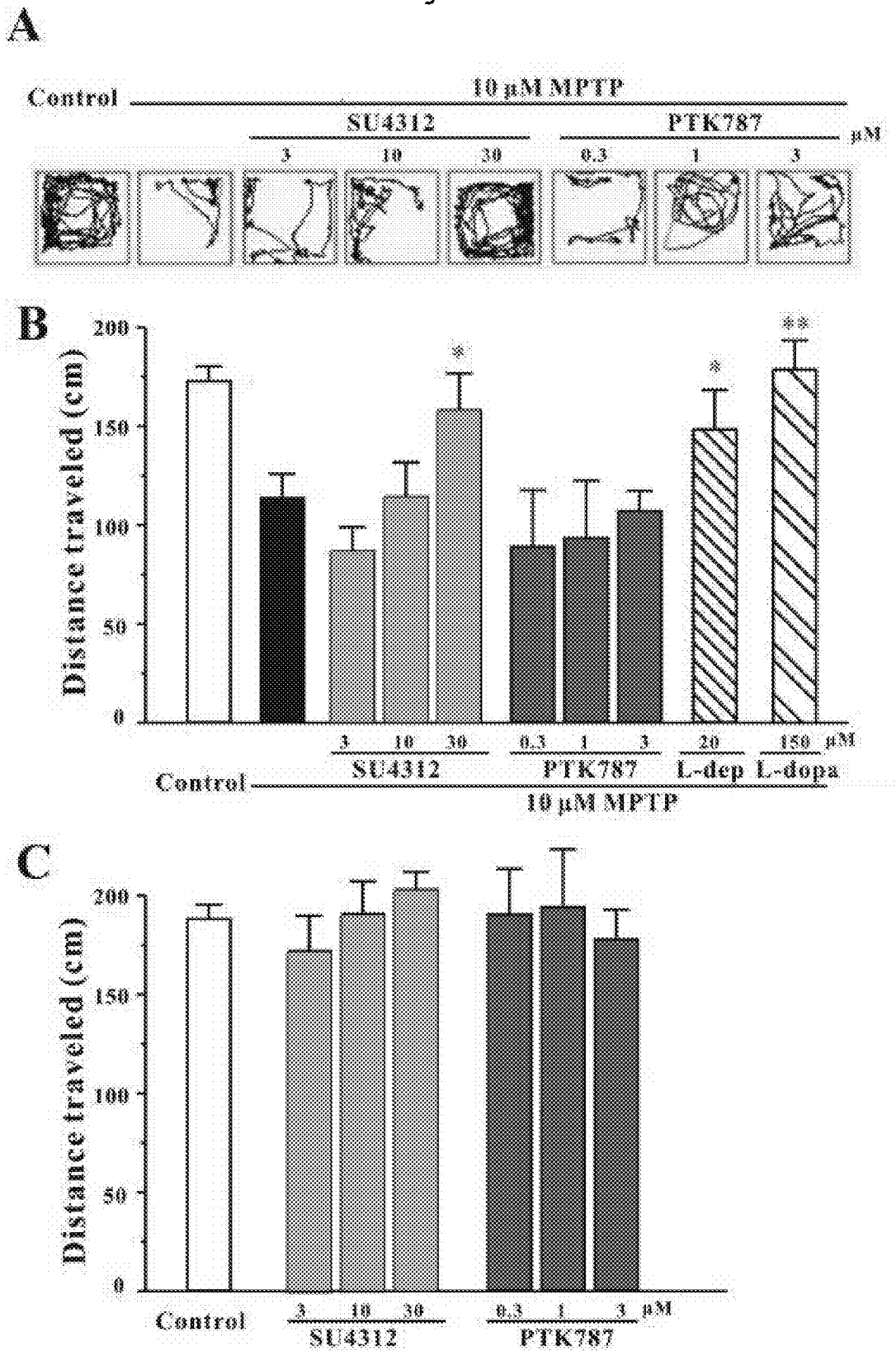
FIG. 4 shows SU4312 attenuated the deficit of locomotion behavior in zebrafish larvae induced by MPTP. (A-C) 1 dpf zebrafish embryos were treated with 200 µM MPTP for 2 days, then co-incubated with 10 µM MPTP and SU4312 or PTK787/ZK222584 at the indicated concentrations for 3 days, and zebrafish larvae co-treated with MPTP and 20 µM L-deprenyl (L-dep) or 150 µM levodopa (L-dopa) were used as the positive controls. After treatment, zebrafish were collected to perform locomotion behavior test using Viewpoint Zebrabox system and the total distance moved in 10 min was calculated. (A) Representative patterns of zebrafish locomotion traced from different treatment groups. (B) Statistic analysis of total distance travelled by each zebrafish larva in different treatment groups, 12 fish larval per group from three independent experiments. (C) 3 dpf zebrafish larvae were treated with SU4312 or PTK787/ZK222584 but without MPTP at the indicated concentrations for 3 days, then locomotion behavior test was performed. The results represented the mean distance travelled by 36 larvae and are expressed in cm/10 min. Values were mean±SEM. *p<0.05 and **p<0.01 versus MPTP group (ANOVA and Dunnett's test).

MPTP markedly altered the swimming behavior of the zebrafish as a consequence of DA neuronal injury (McKinley et al., 2005). As shown in FIG. 4A, the total distance travelled by the zebrafish larvae decreased significantly after exposure to MPTP. SU4312 but not PTK787/ZK222584 ameliorated MPTP-induced deficit of swimming behavior. At the same condition, MPTP-induced deficit of swimming behavior were rescued by positive controls, L-deprenyl (L-dep or selegiline) and levodopa (L-dopa) (FIGS. 4A-C). Neither SU4312 nor PTK787/ZK222584 treatment alone notably altered the swimming behavior of normal zebrafish larvae (FIG. 4D).

1.2.3) Neuroprotective Effects of SU4312 are not Directly Correlated with its Anti-Angiogenic Activity.

Figure 5:
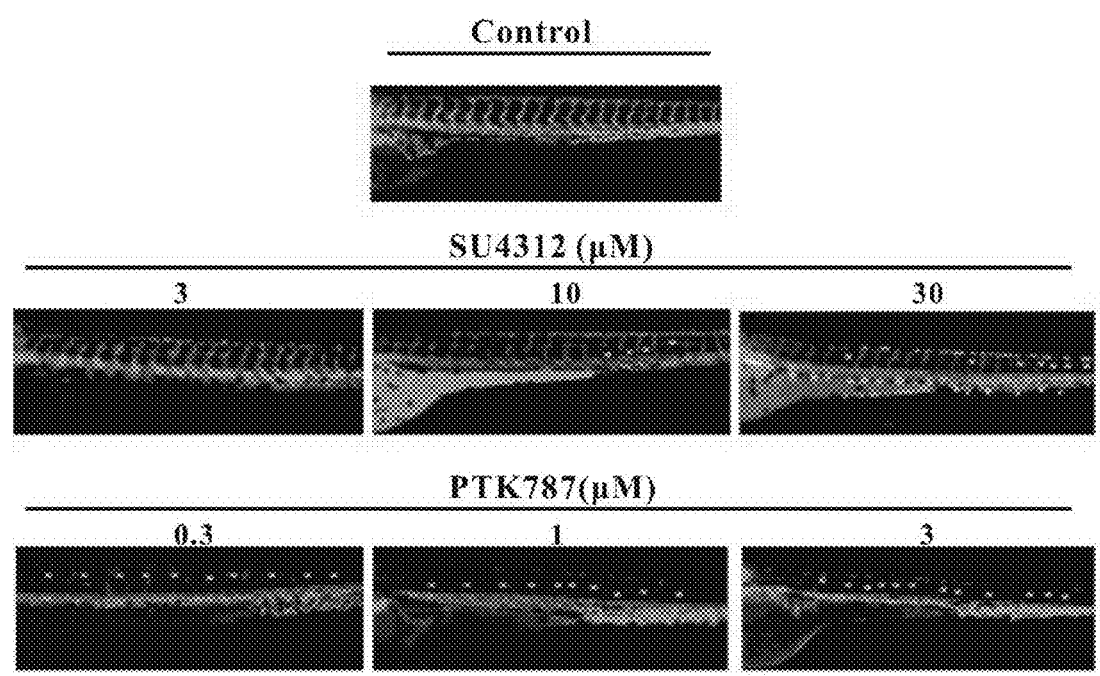
FIG. 5 shows the comparison of anti-angiogenesis effect between SU4312 and PTK787/ZK222584 in zebrafish. One dpf Tg (Fli-1:EGFP) transgenic zebrafish embryos were treated with SU4312 or PTK787/ZK222584 at the indicated concentrations for 48 hours. After treatment, inter segmental vessels (ISV) of zebrafish were observed under fluorescent microscopy. The deficit of blood vessels was indicated by yellow asterisks.

It was further determined if SU4312 and PTK787/ZK222584 within the particular concentration ranges exhibited any anti-angiogenic activities in Tg(fli1:EGFP) transgenic zebrafish embryos. This transgenic model harbors EGFP gene under the control of the fli-1 promoter and thereby allows direct monitoring of endothelial cells under a fluorescence microscopy. FIG. 5 shows the inhibitory effects of SU4312 and PTK787/ZK222584 at different concentrations on intersegmental-vessel (ISV) formation in zebrafish larvae. Compared with the vehicle control, SU4312 (3-30 μM) and PTK787/ZK222584 (0.3-3 μM) showed differential concentration-dependent inhibition of ISV formation in Zebrafish larvae at 3 dpf (FIG. 5). Concordantly, PTK787/ZK222584 evidently exhibited more potent and effective anti-angiogenic activity than SU4312. These results suggested that SU4312 (3-30 μM) but not PTK787/ZK222584 (0.3-3 μM) could prevent MPTP-induced neuronal loss and locomotion deficit in zebrafish. However, the anti-angiogenic activities of these molecules are not correlated with their neuroprotective activities in vivo.

1.2.4) SU4312 Prevents MPP$^+$-Induced Increase of Intracellular NO Level.

Figure 6A:
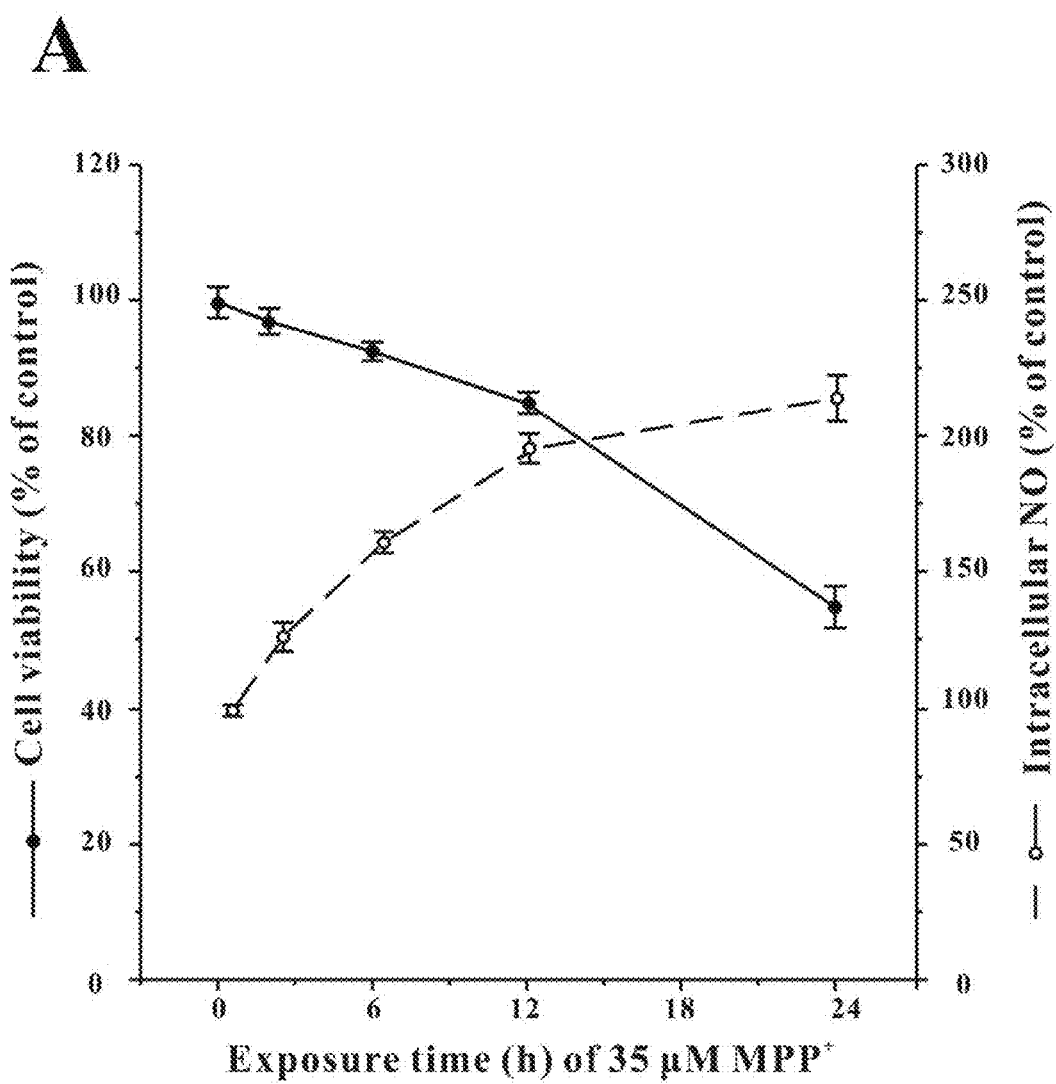
FIG. 6 shows SU4312 reversed the elevated intracellular NO induced by $MPP^+$ in CGNs. (A) $MPP^+$ induces neuronal death and increases the level of intracellular NO in a time-dependent manner. CGNs were exposed to 35 µM $MPP^+$ for different durations as indicated. Cell viability was measured by the MTT assay; and intracellular NO level was measured using DAF-FM diacetate after the $MPP^+$ challenge. (B) Selective nNOS inhibitor prevents $MPP^+$-induced neurotoxicity. CGNs were treated with 7-nitroindazole (7-NI) or 1400W at the indicated concentrations for 2 hours and then exposed to 35 µM $MPP^+$. Cell viability was measured by the MTT assay at 24 hour after the $MPP^+$ challenge. (C) SU4312 reverses the elevated intracellular NO induced by $MPP^+$. CGNs were pre-incubated with or without SU4312 or 7-NI at the indicated concentrations for 2 hours, and exposed to 35 µM $MPP^+$. Intracellular NO level was measured using DAF-FM diacetate as a probe at 24 hour after the $MPP^+$ challenge. Data, expressed as percentage of control, were the mean±SEM of three separate experiments; *p<0.05 and **p<0.01 versus $MPP^+$ group in (B) and (C) (ANOVA and Dunnett's test).

It was reported that NO is associated with MPP$^+$-/MPTP-induced neurotoxicity (Hantraye et al., 1996; Przedborski et al., 1996). To clarify whether NO is involved in neuronal loss in CGNs caused by MPP$^+$, DAF-FM diacetate was used to evaluate the intracellular NO level. It was found that MPP$^+$ induced neuronal death and increased the intracellular NO level in a time-dependent manner (FIG. 6A). For comparison, two NOS inhibitors were also selected to pretreat neurons for 2 hours before the addition of MPP$^+$. A specific nNOS inhibitor, 7-nitroindazole (7-NI), at the concentrations ranging from 3 to 10 μM, inhibited neuronal death and elevated level of intracellular NO induced by MPP$^+$ (FIGS. 6B and 6C). In contrast, a specific iNOS inhibitor 1400W failed to block neuronal death (FIG. 6B).

CGNs were pre-treated with SU4312 (3-30 μM) for 2 hours and then exposed to MPP$^+$ for another 24 hours. It was found that SU4312 attenuated MPP$^+$-triggered elevation of intracellular NO level, indicating that SU4312 prevents MPP$^+$-induced neuronal loss possibly through inhibiting NO overproduction (FIG. 6C).

1.2.5) SU4312 Selectively Inhibits nNOS in a Non-Competitive Manner.

To investigate whether SU4312 directly inhibited NOS, an in vitro assay of NOS activity was used in this study. SU4312 was found to directly and selectively inhibit recombinant human nNOS relative to iNOS, but there was no activity against eNOS. In contrast, PTK787/ZK222584 did not inhibit any of the isoforms even at 1 mM (Table 1).

To investigate the mode of nNOS inhibition by SU4312, SU4312 at the concentrations of 10 and 20 μM was added to the nNOS reaction system containing L-[3H]arginine at the concentrations ranging from 5 to 40 μM. Lineweaver-Burk plots in FIG. 7A show that SU4312 inhibited nNOS in a non-competitive manner, and the Ki value of nNOS inhibition by SU4312 was 12.7 μM (FIG. 7B).

1.2.6) Molecular Docking Simulation Reveals the Interaction Between SU4312 and nNOS.

Figure 8:
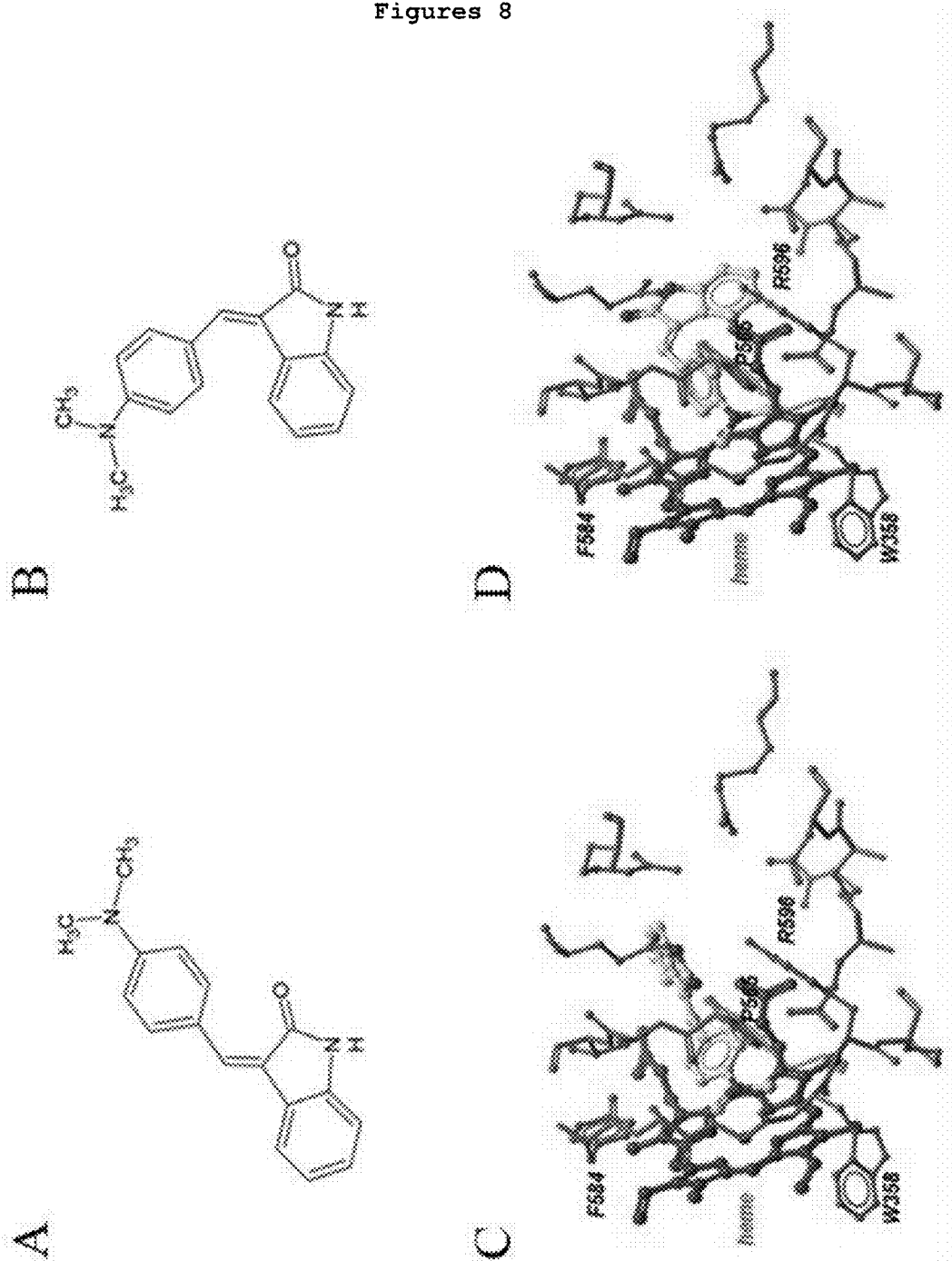
FIG. 8 shows the molecular docking simulation of interactions between SU4312 and nNOS. The structures of cis- and trans-SU4312 were shown in (A) and (B), respectively. Molecular dockings show the binding of cis- and trans-SU4312 with nNOS (PDB code: 3NLV) in (C) and (D), respectively.

To gain further insight into the interaction mechanisms between SU4312 and nNOS, computational docking was performed. Both the cis- and trans-isomers of SU4312 (FIGS. 8C and 8D) showed favorable interaction with the heme group inside nNOS protein (PDB code: 3NLV), with a binding score of −31.25 and −38.98 respectively. As a reference, a binding score of −36.44 was obtained for a known nNOS binder 6-(-4-[2-({2,2-difluoro-2-[(2R)-piperidin-2-yl]ethyl}amino)ethoxy)-4-methylpyridin-2-amine (Xue et al., 2010). In both cis- and trans-cases, the $N(CH_3)_2$ group of SU4312 might interact with $NH_2^+$ of Pro565 and the NH of SU4312 might interact with the COO— of the heme group. The N,N-dimethyl aniline group is located in the binding pocket of nNOS, which is formed by the heme, Pro565 and Arg596 (FIGS. 8C and 8D). On the other hand, neither of the two SU4312 forms showed relatively favorable interactions with iNOS protein as reflected by their binding scores of −11.47 and −12.66 respectively; while no druggable binding pocket could be found near the heme for eNOS.

1.2.7) SU4312 could Reach the Brain

To investigate whether SU4312 could reach the brain, an HPLC method was used to detect SU4312 after i.p. administration. The plasma concentration-time profile of SU4312 after i.p. administration was shown in FIG. 9A. Most importantly, SU4312 could rapidly penetrate into the brain and be detected in the brain 15 min post-administration (FIG. 9D). However, the brain concentration of SU4312 quickly decreased as almost no SU4312 was detected in the brain at 60 min after i.p. administration (FIG. 9F).

1.3) Discussion

SU4312 is originally designed as an anti-cancer drug candidate from targeting VEGFR-2. Under light illumination, SU4312 could interchange freely between the cis- and trans-forms in solution. These forms of SU4312 selectively inhibit VEGFR-2 with $IC_{50}$ values of 0.8 (cis-form) and 5.2 (trans-form) μM, respectively (Sun et al., 1998). The experimental results showed that SU4312, even at a concentration as high as 30 μM, did not induce any neurotoxicity in primary neuron culture or in zebrafish. These results, together with those of a previous study that showed that prolonged SU4312 treatment (3 mg of SU4312 every 5 days for 12 weeks) did not damage retinal photoreceptors or ganglion cells in rodents (Miki et al., 2010), indicate the safety of SU4312 in neurons.

The same in vitro model used in the current study had previously demonstrated the neuroprotective effects of VEGF against $MPP^+$-induced neuronal death in CGNs (Cui et al., 2011). VEGF (10-300 ng/ml) protected neurons against $MPP^+$-induced neurotoxicity via activating VEGFR-2/Akt pathway (Cui et al., 2011). Further, unpublished results have also shown that VEGF did not significantly affect the production of NO at the concentration exhibiting its neuroprotective activity. If SU4312 works only as a VEGFR-2 inhibitor to inhibit VEGFR-2/Akt pathway, it will promote but not decrease $MPP^+$-induced neurotoxicity. Therefore, the neuroprotection of SU4312 must be independent from its anti-VEGFR-2 action. To further rule out the possibility that SU4312 protected neurotoxicity via inhibiting angiogenesis, PTK787/ZK222584 was applied in same models. PTK787/ZK222584 inhibits VEGFR-2 with an $IC_{50}$ value of 37 μM in vitro, which is about 20 times lower than that of cis-SU4312 (Sun et al., 1998). As expected, PTK787/ZK222584 at 1 μM inhibited angiogenesis with the potency similar to that of SU4312 at 30 μM in zebrafish (FIG. 5). Interestingly, PTK787/ZK222584 at the same concentration failed to inhibit $MPP^+$-induced neurotoxicity in CGNs, SH-SY5Y cells, PC12 cells or MPTP-induced neurotoxicity in zebrafish. These results suggest that the neuroprotective effects of SU4312 might not be closely correlated with its anti-angiogenic property.

It is known that NO mediates $MPP^+$- and MPTP-induced neurotoxicity both in vitro and in vivo (Gonzalez-Polo et al., 2004a; Przedborski et al., 1996). As shown in FIG. 6, SU4312 inhibited $MPP^+$-induced increase of intracellular NO level, indicating that SU4312 may affect the formation or degradation of endogenous NO. Endogenous NO is produced only by NOS while L-arginine is converted to L-citruline (Fedorov et al., 2004). Three isotypes of NOS, namely, nNOS, iNOS and eNOS, have been identified (Alderton et al., 2001). nNOS is the predominant form in neurons in the central nervous system; eNOS is mainly present in cerebral vascular endothelial cells whereas iNOS is expressed in astrocytes and microglia (Estevez et al., 1998). It is noteworthy that ablation of eNOS has no bearing on $MPP^+$-induced neurotoxicity (Gonzalez-Polo et al., 2004a). According to the experimental results, $MPP^+$-induced neuronal death was significantly inhibited by the selective nNOS inhibitor 7-NI, but not the selective iNOS inhibitor 1400W, whereas the increase of intracellular NO level was also similarly reduced. Consequently, SU4312 may prevent $MPP^+$-induced neurotoxicity by inhibiting nNOS. Using in vitro NOS activity assay, it was found that SU4312 directly inhibited the activity of purified NOS while it showed high selectivity toward nNOS. Furthermore, SU4312 did not alter $K_m$ but increased the appeared $1/V_{max}$. There is a linear relationship between the appeared $1/V_{max}$ and SU4312 concentrations. All these results suggest that SU4312 prevented neurotoxicity at least partially by directly inhibiting nNOS in a non-competitive manner.

Docking simulation revealed a possible molecular interaction between isoforms of SU4312 and nNOS. In cis-form-SU4312-nNOS and trans-form-SU4312-nNOS complexes, the NH group of SU4312 has close contact with the heme domain of nNOS. The heme domain is required for nNOS dimerization, a process to convert inactive nNOS monomer into active dimeric form (Roman & Masters, 2006). The heme domain is also the final electron acceptor in the electron flow, which is required for NO production (Zhou & Zhu, 2009). The interaction between SU4312 and the heme domain of nNOS may disrupt nNOS dimerization and/or impair the electron transfer process, and subsequently causes a non-competitive inhibition event. Furthermore, the binding pocket involving the heme, Pro565 and Arg596 of nNOS may facilitate the interaction between SU4312 and nNOS and support a prolonged inhibition.

Figure 10:
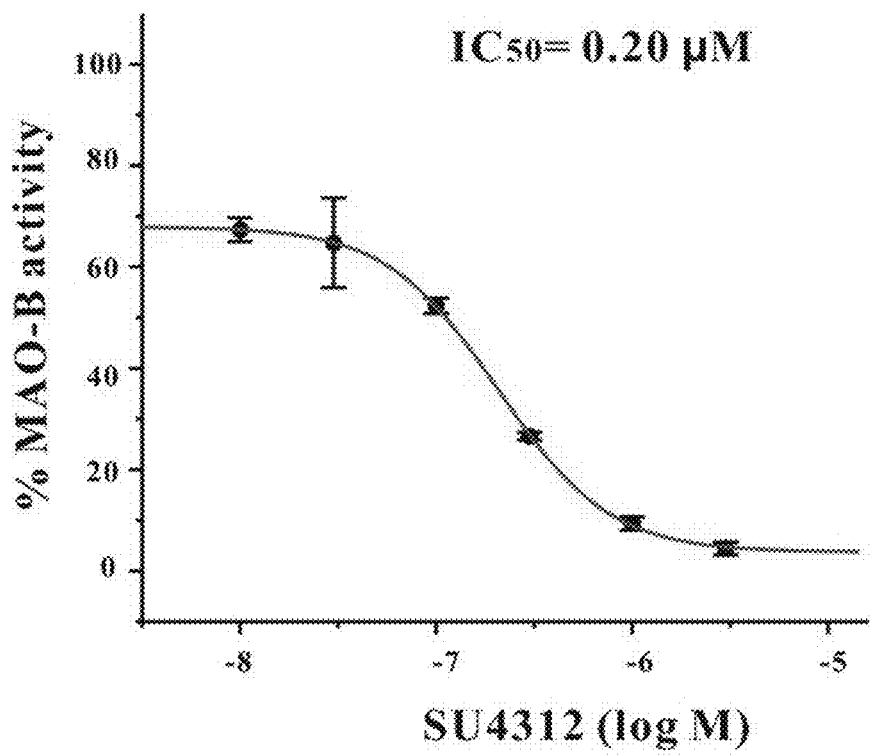
FIG. 10 shows SU4312 inhibited monoamine oxidase-B (MAO-B) activity in a concentration dependent manner in vitro.
Figure 11:
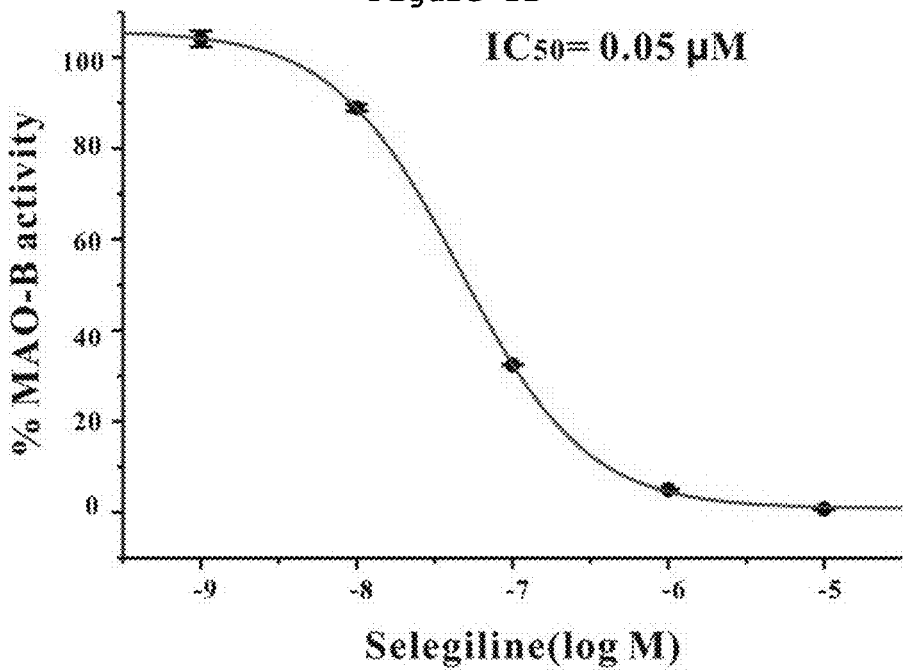
FIG. 11 shows Selegiline inhibited MAO-B activity in a concentration dependent manner in vitro.

Besides nNOS inhibition, other molecular mechanisms, such as monoamine oxidase-B (MAO-B) inhibition and kinases antagonizing, may also contribute to neuroprotective effects of SU4312. For example, some NOS inhibitors were found to be MAO-B inhibitors that prevented MPTP neurotoxicity (Herraiz et al., 2009). Moreover, recent studies have shown that chemicals with indoline-one structure might inhibit LRRK2, a kinase associated with an increased risk of PD, implying that the neuroprotective effects of SU4312 might be from LRRK-2 inhibition (Lee et al., 2010). To rule out the possibility that SU4312 protected against neurotoxicity via directly inhibiting MAO-B, MAO-B inhibition activity of SU4312 was examined using the MAO-Glo™ assay kit (Promega Inc., USA). The experimental results have shown that SU4312 significantly inhibit the activity of MAO-B with $IC_{50}$ at about 0.2 μM (FIG. 10), while selegiline, or L-deprenyl, a well-known selective MAO-B inhibitor, also notably inhibit MAO-B activity with $IC_{50}$ at about 0.05 μM (FIG. 11), suggesting the neuroprotective effects of SU4312 may be directly via inhibiting MAO-B.

1.4) Conclusion

In conclusion, the above findings demonstrated that SU4312 exhibits neuroprotection against $MPP^+$ at least partially via selective and direct inhibition of nNOS. In view of the capability of SU4312 to reach the brain in rats, these results offer support for further development of SU4312 in the treatment of neurodegenerative disorders, particularly those associated with NO-mediated neurotoxicity.

Example 2

Neuroprotection by SU5416

2.1) Materials and Methods 2.1.1) Ethics Statement of Animal Experiments

All rodent experiments were conducted according to the ethical guidelines of Animal Subjects Ethics Sub-committee (ASESC), the Hong Kong Polytechnic University; and the protocol was approved by ASESC, the Hong Kong Polytechnic University (permit No. 10/15). All surgeries were performed under sodium pentobarbital anesthesia, and all efforts were made to minimize animal suffering.

All zebrafish experiments were conducted according to the ethical guidelines of Institute of Chinese Medical Sciences (ICMS), University of Macau; and the protocol was approved by ICMS, University of Macau.

2.1.2) Primary Cerebellar Granule Neuron Cultures

Rat CGNs were prepared from 8-day-old Sprague-Dawley rats (The Animal Care Facility, The Hong Kong Polytechnic University) as described by Li et al., 2005. Briefly, neurons were seeded at a density of $2.7 \times 10^5$ cells/ml in basal modified Eagle's medium (Invitrogen) containing 10% fetal bovine serum, 25 mM KCl, 2 mM glutamine, and penicillin (100 units/ml)/streptomycin (100 µg/ml). Cytosine arabinoside (10 µM) was added to the culture medium 24 hours after plating to limit the growth of non-neuronal cells. With the use of this protocol, more than 95% of the cultured cells were granule neurons.

2.1.3) Measurement of Neurotoxicity

The percentage of surviving neurons in the presence of SU5416 and/or MPP$^+$ was estimated by determining the activity of mitochondrial dehydrogenases with 3(4,5-dimethylthiazol-2-yl)-2.5-diphenyltetrazolium bromide (MTT) assay (Li et al., 2007). The assay was performed according to the specifications of the manufacturer (MTT kit I; Roche Applied Science). Briefly, the neurons were cultured in 96-well plates, 10 µl of 5 mg/ml MTT labeling reagent was added to each well containing cells in 100 µl of medium, and the plates were incubated at 37° C. for 4 hours in a humidified incubator. After the incubation, 100 µl of the solvating solution (0.01 N HCl in 10% SDS solution) was added to each well for 16-20 hours. The absorbance of the samples was measured at a wavelength of 570 nm with 655 nm as a reference wavelength. Unless otherwise indicated, the extent of MTT conversion in cells exposed to MPP$^+$ is expressed as a percentage of the control.

Cytotoxicity was determined by measuring the release of lactate dehydrogenase (LDH). Briefly, cells were precipitated by centrifugation at 500 g for 5 min at room temperature, 50 µl of the supernatants was transferred into new wells, and LDH was determined using the in vitro toxicology assay kit (Roche). The absorbance of the samples was measured at a wavelength of 490 nm with 655 nm as a reference wavelength.

2.1.4) FDA/PI Double Staining Assay

Viable granule neurons were stained with fluorescein formed from fluorescein diacetate (FDA) by esterase in viable cells. Propidium iodide (PI) can penetrate cell membranes of dead cells to intercalate into double-stranded nucleic acids. Briefly, after incubation with 10 µg/ml of FDA and 5 µg/ml of PI for 15 min, the neurons were examined and images were acquired using UV light microscopy for comparison with photos taken under phase contrast microscopy.

2.1.5) Hoechst Staining and Immunostaining

Chromatin condensation was detected by staining the cell nucleus with Hoechst 33342 as described by Li et al., 2005. CGNs ($2.7 \times 10^6$ cells) grown in a 35-mm dish were washed with ice-cold phosphate-buffered saline (PBS), fixed with 4% formaldehyde in PBS, membrane-permeabilized in 0.1% Triton X-100 and blocked in 1% BSA. Cells were then exposed to a primary nNOS antibody (Santa Cruz) overnight at 4° C. followed by incubation at room temperature with an Alexa Fluor 488-conjugated secondary antibody. After immunostaining, cells were then stained with Hoechst 33342 (5 µg/ml) at 4° C. for 5 min. Images were acquired using a fluorescence microscope at ×100 magnification.

To quantify the percentage of apoptotic nuclei in each group, photos of each dish (n=3 dishes in each group for three independent experiments) were taken at five random fields and the numbers of apoptotic nuclei and total nuclei (n=300) were counted, and the percentage of apoptotic nuclei was averaged.

2.1.6) Measurement of Intracellular NO

Intracellular NO was monitored with (4-amino-5-methylamino-2',7'-difluorofluorescein) DAF-FM diacetate, a pH-insensitive fluorescent dye that emits increased fluorescence after reaction with an active intermediate of NO formed during the spontaneous oxidation of NO to $NO_2$ (Sheng et al., 2005). DAF-FM solution was added to the culture medium (final concentration: 5 µM). After incubation for 30 min in a $CO_2$ incubator, cultures were washed twice with PBS and incubated for another 30 min to allow complete de-esterification of the intracellular diacetate for strong fluorescence. The DAF-FM fluorescence in CGNs was quantified by a multi-detection microplate reader using excitation and emission wavelengths of 495 nm and 515 nm, respectively. The measured fluorescence values were expressed as a percentage of the fluorescence in the control cells.

2.1.7) Western Blotting Analysis

Briefly, neurons were harvested in a cell lysis buffer. Protein was separated on SDS-polyacrylamide gel and transferred onto polyvinyldifluoride membranes. After membrane blocking, proteins were detected using primary antibodies. After incubation at 4° C. overnight, signals were obtained after binding to chemiluminescent secondary antibodies. Blots were developed using an ECL plus kit (Amersham Bioscience, Aylesbury, UK) and exposed to Kodak autoradiographic films. All data were from three independent experiments and were expressed as the ratio to optical density (OD) values of the corresponding controls for statistical analyses.

2.1.8) Maintenance of Zebrafish and Drug Treatment

Wild-type zebrafish (AB strain) and Tg(fli-1:EGFP) transgenic zebrafish were maintained as described in the Zebrafish Handbook (Westerfield, 1993). Zebrafish embryos were generated by natural pair-wise mating (3-12 months old) and were raised at 28.5° C. in embryo medium (13.7 mM NaCl, 540 µM KCl, pH 7.4, 25 µM $Na_2HPO_4$, 44 µM $KH_2PO_4$, 300 µM $CaCl_2$, 100 µM $MgSO_4$, 420 µM $NaHCO_3$, pH 7.4). Drugs were dissolved in DMSO and directly added into zebrafish embryo medium to treat fish without refreshing in 2-3 days (Final concentration of DMSO was always less than 0.5%, and showed no toxicity to zebrafish). Equal concentration of DMSO in embryo medium was used as vehicle control in each experiment.

2.1.9) Exposure of Zebrafish to MPTP

Healthy zebrafish embryos were picked and dechorionated manually at 1 day post fertilization (dpf) then distributed into a 12-well plate with 20 fish embryos or a 6-well microplate with 30 fish embryos in each well. In pilot experiments, several doses of MPTP were added to embryo medium (final concentration from 50 to 800 µM) and 1 dpf fish embryo were treated for 48 hours, The optimal dose used (200 µM) induced a significant decrease in brain diencephalic dopaminergic neurons without any detectable systematic toxicity (data not shown). Thus subsequent studies were performed with 200 µM MPTP for whole-mount immunostaining and gene expression experiments.

Normally as late as 3 dpf, zebrafish larvae show very little spontaneous swimming, but by 5 dpf they spontaneously swim longer distances and independently search for food. The MPTP exposure therefore needs to last 5 days from 1 dpf. In pilot locomotion behavioral test, 3-day treatment starting from 1 dpf with 200 μM MPTP in embryo medium killed all the fish larvae, however, after 2-day treatment at 1 dpf with 200 μM MPTP then withdraw 3 days, and the deficit behavior recovered at 6 dpf. Finally, the optimal MPTP exposure was after 2-day treatment starting from 1 dpf with 200 μM MPTP, zebrafish larvae were maintained in embryo medium containing 10 μM MPTP for another 3 days, the swimming distance significantly decreased and without any detectable systematic toxicities. Thus subsequent locomotion behavioral studies were performed with 200 μM MPTP for 2-day treatment at 1 dpf then replacing with media containing 10 μM MPTP for another 3-day incubation.

2.1.10) Whole-Mount Zebrafish Immunostaining with Antibody Against Tyrosine Hydroxylase Whole-mount immunostaining in zebrafish was performed as described in Zhang et al., 2011. Briefly, zebrafish were fixed in 4% paraformaldehyde (wt/vol in PBS) for 5 h at room temperature or overnight at 4° C., washed with PBS 3 times, then kept in absolute ethanol at −20° C. to dehydrate for at least 2 h or up to 1 week. Fixed samples were bleached in 10% H2O2 then blocked (2% lamb serum and 0.1% BSA in PBST) for 1 h at room temperature. A mouse anti-tyrosine hydroxylase (TH) monoclonal antibody (Millipore, USA) was used as the primary antibody and incubated with the sample overnight at 4° C. On the next day, samples were washed 6 times with PBST (30 min each wash), followed by incubation with secondary antibody according to the method provided by the Vectastain ABC kit (Vector Laboratories, USA). After staining, zebrafish were flat-mounted with 3.5% methylcellulose and photographed. Semi-quantification of area of TH+ region was assessed by an investigator blinded to the drug treatment history of zebrafish using Image-Pro Plus 6.0 software (Media Cybernetics, Silver Spring, Md., USA). Results were expressed as percentage of area of TH+ region in untreated control group.

2.1.11) Paraffin-Embedding, Serial Sectioning and Immunostaining of Zebrafish Larval After drug treatment, fixation of zebrafish larval was performed as the procedure in whole-mount immunostaining. The fixed specimens were then mounted on 1% agarose blocks in a common linear plane to ensure that the microtome blade passes through each specimen simultaneously. The specimen-containing agarose was converted into a sectionable paraffin wax block and conducted processes as described by Sabaliauskas et al., 2006. Consecutive coronal sections were cut 5 μM thick using a rotary microtome (Leica RM2235, Germany) and mounted on microscope slides. Immunostaining of zebrafish larval sections was performed as described by Gal et al., 2010 with minor modifications. Paraffin sections were deparaffinized in xylene, hydrated in graduated alcohol solutions and incubated for 30 min in 3% $H_2O_2$ in PBS to inactivate endogenous peroxidases. Following antigen retrieval in citrate buffer for 15 min in a microwave oven, sections were blocked at room temperature with 10% horse serum for 1 hour. Sections were reacted overnight at 4° C. with rabbit anti-mouse TH polyclonal antibody (Millipore, USA) at 1:400 dilutions in immunostaining primary antibody dilution buffer (Beyotime, China). For detection of primary antibody, the EnVision Detection kit (Gene Tech., Shanghai, China) was used. Detection was done by the appropriate second antibody with peroxidase conjugate and DAB substrate. Finally, sections were coverslipped with neutral balsam. The results were analyzed by counting the numbers of TH-positive cells at ×20 magnifications on a stereomicroscope (BX51, Olympus Corp. Japan). TH-positive cells in 3 matched sections of each zebrafish were counted and averaged. 12 fish per treatment group were employed. The average number of TH-positive cells per section was used to represent dopaminergic neuron livability.

2.1.12) Locomotion Behavioral Test of Zebrafish

After drug treatment, zebrafish larvae at 6 dpf were transferred into 96-well plates (1 fish/well and 12 larvae/group). The larvae were discarded due to excessive stress reaction to the handling and monitoring of behavior (such as rapid and disorganized swimming or immobility for 2 min). The experiments were performed in a calm sealed area. The larvae were allowed to habituate to the new environment for 30 min. Swimming behavior was monitored by an automated video tracking system (Viewpoint, ZebraLab, Life-Sciences). The 96-well plates and camera were housed inside a Zebrabox and the swimming pattern of each fish was recorded for 10 min and for 3 times, once every other 10 min. The total distance moved was defined as the distance (in cm) that the fish had moved during one session (10 min).

2.1.13) Morphological Observation of Zebrafish

After drug treatment, zebrafish were removed from the microplate and observed for gross morphological changes of blood vessel under a fluorescence microscope (Olympus am Motorized Inverted Microscope, Japan) equipped with a digital camera (DP controller, Soft Imaging System, Olympus). Images were analyzed with Axiovision 4.2 and Adobe Photoshop 7.0.

2.1.14) In Vitro nNOS Activity Assay

Rat cerebellum nNOS was from Calbiochem. NOS activity was determined by monitoring the conversion of L-[3H] arginine to [3H]citrulline following the instructions provided by the kit (Calbiochem). The reaction mixture contained a final volume of 40 μl with 25 mM Tris-Cl at pH 7.4, 3 μM tetrahydrobiopterin, 1 μM FAD, 1 μM FMN, 1 mM NADPH, 0.6 mM $CaCl_2$, 0.1 μM calmodulin, 2.5 μg of pure NOS enzyme, 5 μl L-[3H]arginine (Perkin Elmer, Waltham, Mass., USA), and different concentrations of the tested reagents. The reaction mixture was incubated at 22° C. for 45 min. The reaction was quenched by adding 400 μl of stopping buffer (50 mM HEPES, pH 5.5, and 5 mM EDTA). Unreacted L-[3H]arginine was then trapped by 100 μl of equilibrated resin in a spin cup followed by centrifugation at 13,200 rpm for 30 s.

2.1.15) shRNA Design

ShRNA against rat nNOS was designed according to Mahairaki et al, 2009. Briefly, the siRNA sequence GCA-CUGGUGGAGAUCAACA (SEQ ID NO: 3), which corresponds to exon 10 of the rat nNOS (GenBank Accession No. NM_052799), was used to generate shRNA. Oligonucleotides that contained the sense and antisense sequences of the siRNA target of interest flanking a standard hairpin loop sequence (TTCAAGAGA) were synthesized. Sense and antisense oligonucleotides were then annealed and cloned into pG418-GFP vector to express shRNA directed against nNOS under the control of the U6 promoter (GenePharma, Shanghai, China). A negative control shRNA (ShNC) with the same nucleotide composition but lacks significant sequence homology to the genome was also used in the experiments.

2.1.16) Cell Transfection

PC12 pheochromocytoma cells were cultured in medium that consisted of DMEM, 10% heat-inactivated horse serum, 5% fetal bovine serum, 100 U/ml penicillin, and 100 µg/ml streptomycin in a 37° C., 5% $CO_2$ incubator. $2.0 \times 10^5$ cells were transfected with 3 µg indicated plasmids by using LIPOFECTAMINE 2000 (Invitrogen) according to the manufacturer's instructions. Selection media that contained 100 µg/ml G418 (Sigma) were added to the cells 24 hours after transfection.

2.1.17) Data Analysis and Statistics

Data are expressed as the means±SEM, and statistical significance was determined by analysis of variance with Dunnett's test in the case of multiple comparisons with control or Turkey's test. Differences were accepted as significant at $p<0.05$.

2.2) Results 2.2.1) SU5416 Prevented $MPP^+$-Induced Neuronal Apoptosis in a Concentration-Dependent Manner After cultured for 8 days in vitro, CGNs were pre-treated with SU5416 at the concentrations of 3, 10, 20 or 30 µM for 2 hours, and then treated with 35 µM $MPP^+$ for another 24 hours. Cell viability was measured using the MTT assay. It was found that SU5416 prevented 35 µM $MPP^+$-induced cell death in a concentration-dependent manner (FIG. 12A). However, treatments with 30 µM SU5416 alone for 26 hours did not produce any cell proliferative or cytotoxic effects. VEGFR-2 kinase inhibitor II (VRI), another specific VEGFR-2 inhibitor with an $IC_{50}$ value of 70 µM, was also tested in this model. Interestingly, VRI at 1 and 3 µM failed to block neuronal loss in vitro (FIG. 12A).

To further characterize the effects of SU5416 on the neurotoxicity of $MPP^+$, CGNs were pretreated with 20 µM SU5416 and exposed to 35 µM $MPP^+$ for 2 hours. The neurons were examined by FDA/PI double staining. It was found that SU5416 significantly blocked the loss of neurons and reversed the morphological alteration, including unhealthy bodies and broken extensive neuritic network, induced by $MPP^+$ (FIGS. 12B and 12C). According to the counts of apoptotic bodies stained by Hoechst 33342, SU5416 significantly reversed neuronal apoptosis induced by $MPP^+$ (FIGS. 12C and 12D).

NO is implicated in the neurotoxicity of $MPP^+$ (Hatraye et al., 1996; Przedborski et al., 1996). To investigate whether NO was involved in this neuronal apoptosis model, nNOS immunostaining and NOS inhibitors were used to treat neurons for 2 hours prior to the addition of $MPP^+$. It was observed that there were nNOS-positive neurons in the CGNs (FIG. 12C). Moreover, a pan-NOS inhibitor 2-ethyl-2-thiopseudourea (EPTU, IC50 values of 0.017 µM for iNOS. and 0.036 µM for nNOS) prevented $MPP^+$-induced neuronal death in CGNs (FIG. 12A). The roles of NOS iso-enzymes were also examined by using specific inhibitors. It was found that the specific nNOS inhibitor 7-nitroindazole ($IC_{50}$ values of 0.7 µM for nNOS, and 20 µM for iNOS) protected against neuronal apoptosis in this model, whereas iNOS inhibitor 1400W ($IC_{50}$ values of 0.007 µM for nNOS, and 2 µM for iNOS) did not show protection (FIG. 12A).

2.2.2) SU5416 Prevented MPTP-Induced Neurotoxicity in Zebrafish

Figure 13:
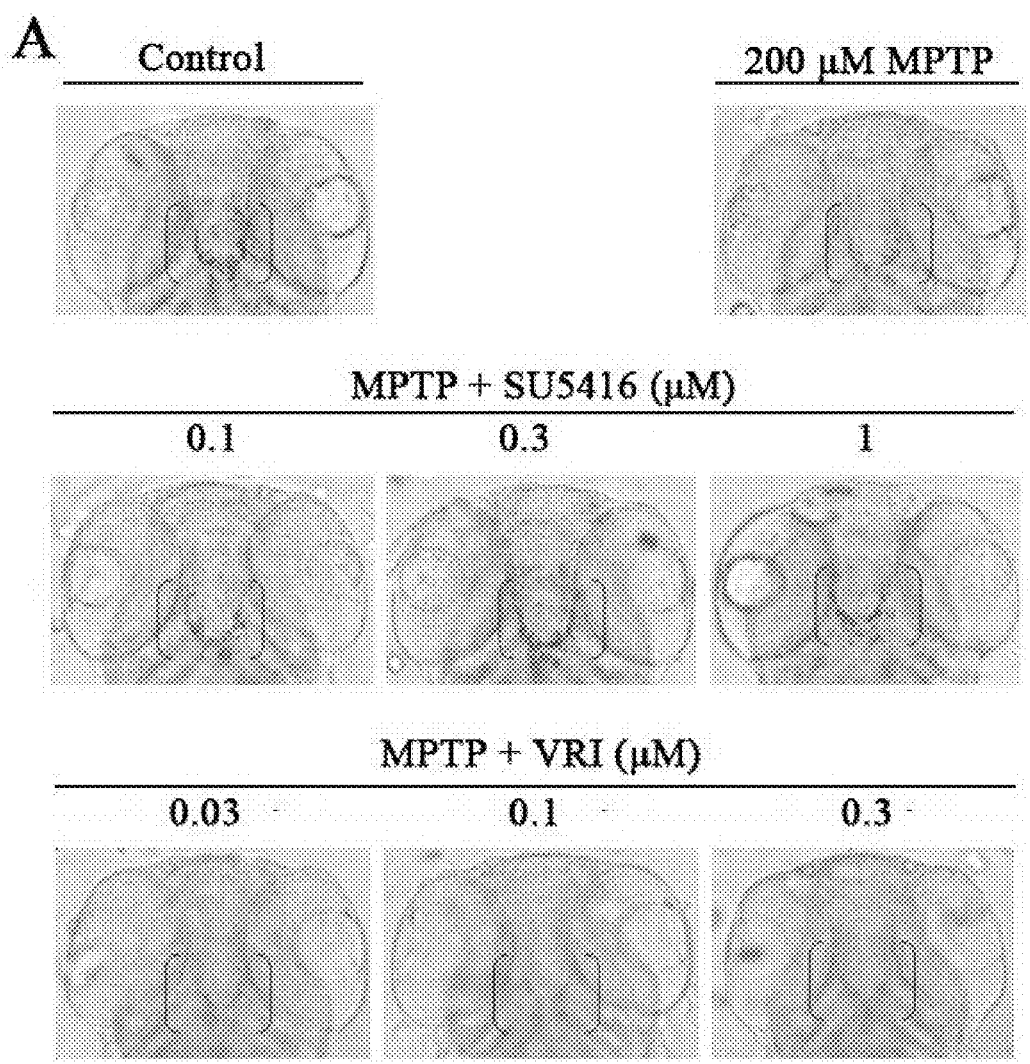
FIG. 13 shows SU5416 protected against MPTP-induced $TH^+$ region area decrease in zebrafish. One dpf zebrafish embryos were co-incubated with 200 µM MPTP and SU5416, VRI or 0.3% DMSO (vehicle control) at the indicated concentrations for 2 days. After treatment, zebrafish were collected to perform whole-mount immunohistochemistry. (A) Representative pictures of whole-mount immunostaining of zebrafish brain from different treatment groups. (B) Magnification of diencephalic area of zebrafish larval (indicated by red bracket in FIG. 2A). (C) Statistical analysis of $TH^+$ region area in each treatment group (20 fish embryos per group). Data, expressed as percentage of control, were the mean±SEM of three separate experiments; ##p<0.01 versus control; *p<0.05 and **p<0.01 versus MPTP group (Turkey's test).
Figure 13:
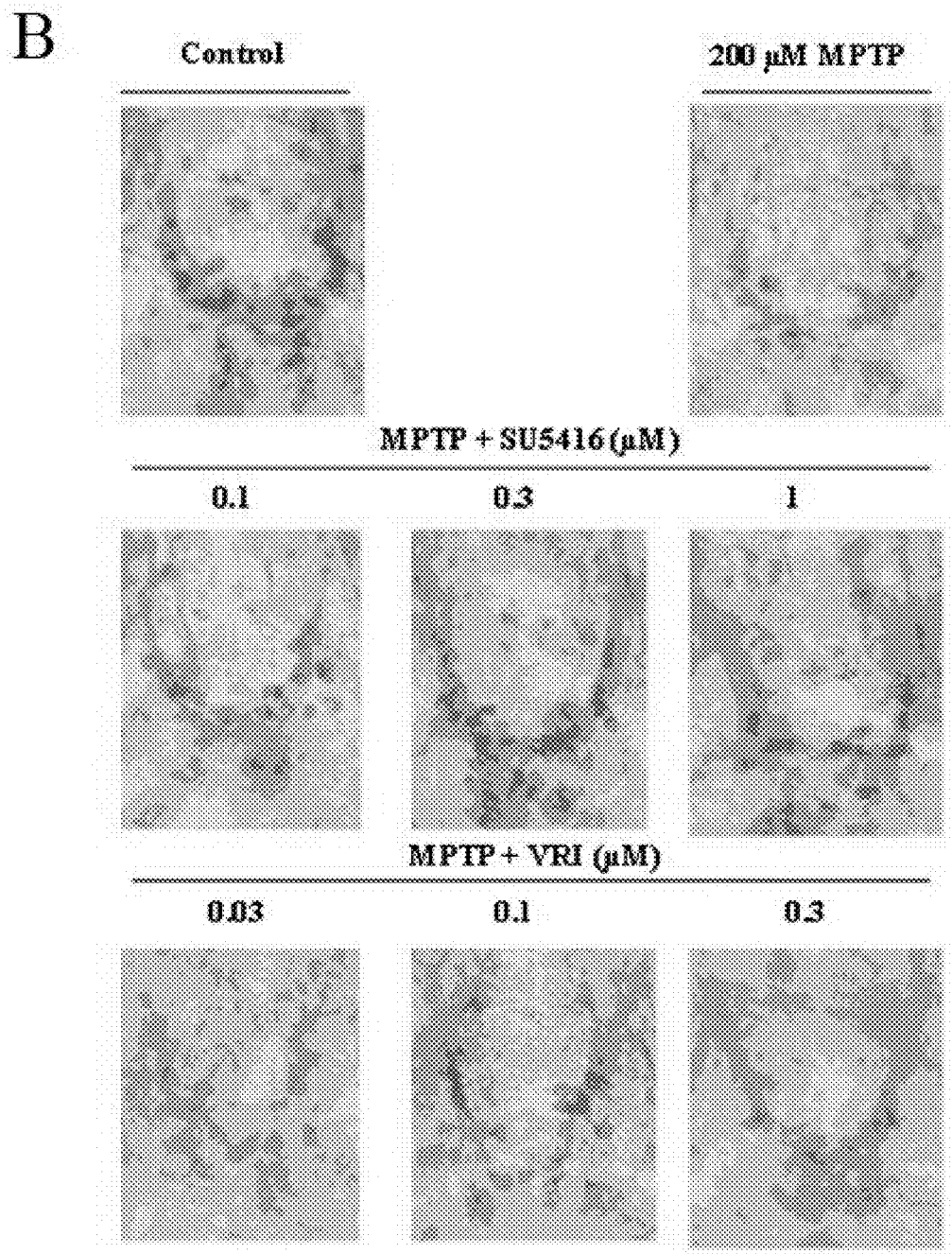
Figure 13:
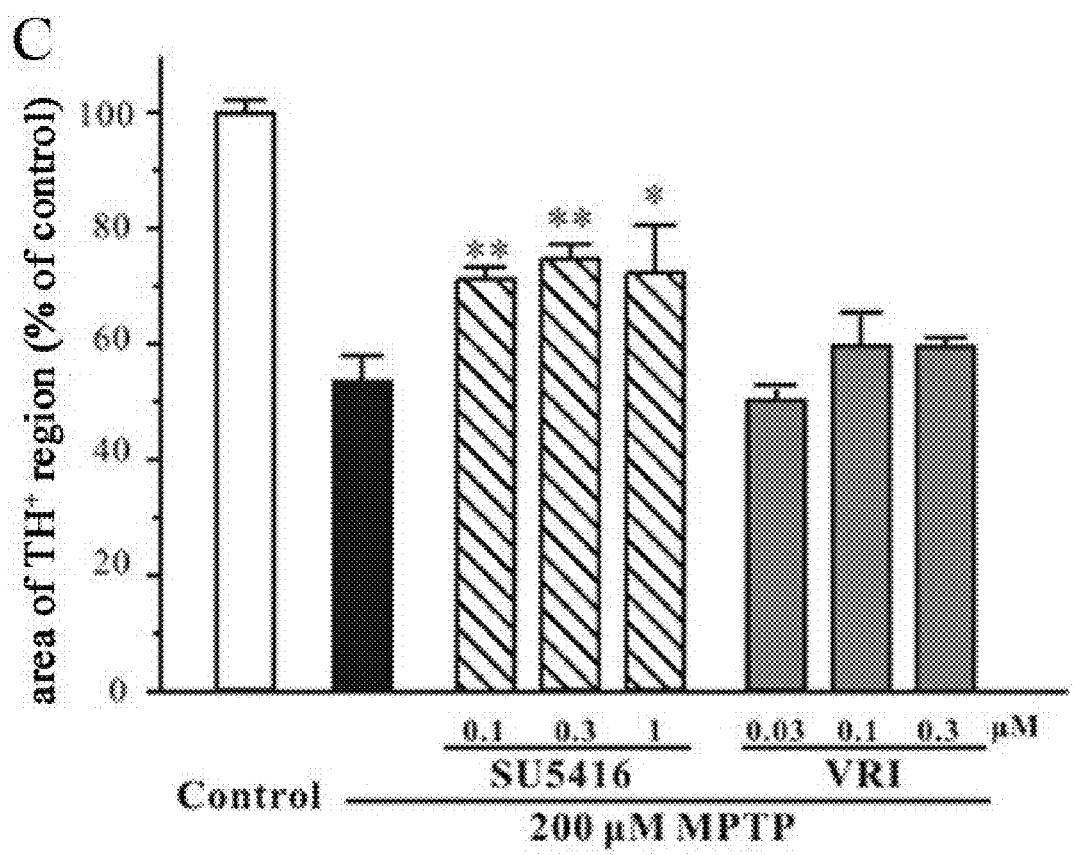

To assess the neuroprotective potential of SU5416 in vivo, zebrafish embryos at 1 dpf were exposed to 200 µM MPTP for 2 days, and the dopaminergic system in the brain of zebrafish was then examined by whole-mount immunostaining with specific antibody against TH. After MPTP treatment, the area of TH-immunoreactive regions observed in the diencephalons of zebrafish (indicated by red brackets) were decreased dramatically (FIGS. 13A and 13B). Importantly, SU5416 (0.1-1 µM) significantly prevented the decrease in the area of $TH^+$ region induced by MPTP. In contrast, VRI (0.03-0.3 µM) could not prevent MPTP-induced decrease in $TH^+$ region area in zebrafish (FIG. 13). Both drugs at higher concentration, SU5416 at 10 µM and VRI at 3 µM, showed toxicity to zebrafish (data not shown).

To further confirm the protective effect of SU5416 against MPTP-induced dopaminergic neurotoxicity and to accurately observe changes of dopaminergic neurons in zebrafish, paraffin-embedding, serial sectioning and immunostaining of zebrafish larval were performed. TH-positive neuron count showed MPTP treatment significantly decreased the number of dopaminergic neurons, and 1 µM SU5416 co-treatment obviously prevented the loss of dopaminergic neurons (FIG. 14). SU5416 treatment alone did not notably alter the number of dopaminergic neurons.

Figure 15:
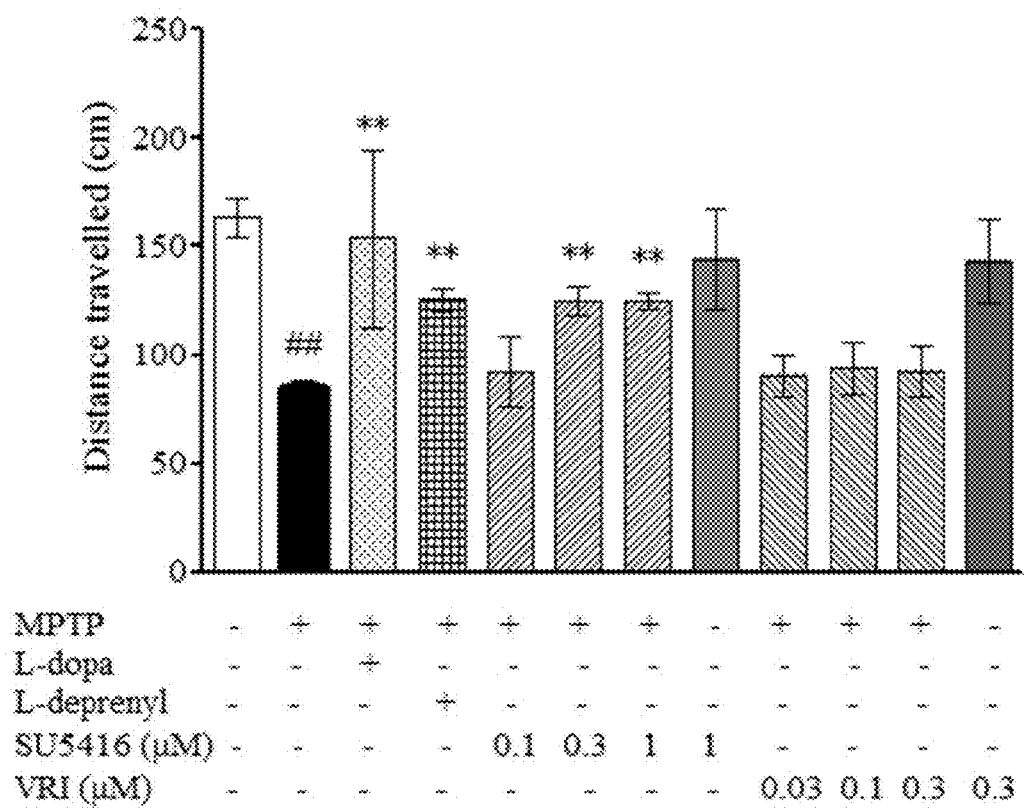
FIG. 15 shows SU5416 attenuated the deficit of locomotion behavior on zebrafish larval induced by MPTP. One dpf zebrafish embryos were treated with 200 µM MPTP for 2 days, and then co-incubated with 10 µM MPTP and SU5416 or VRI at the indicated concentrations for 72 hours, and zebrafish larval co-treated with MPTP and 150 µM L-dopa or 20 µM L-deprenyl were used as positive controls. After treatment, zebrafish were collected to perform locomotion behavior test using Viewpoint Zebrabox system and total distances travelled in 10 min were calculated. Data, expressed as percentage of control, were the mean±SEM of 12 fish larvae per group from 3-time independent experiments. ##p<0.01 versus control group; **p<0.01 versus MPTP group (Turkey's test).

As shown in FIG. 15, the total distance travelled by the zebrafish larvae decreased significantly after exposure to MPTP. SU5416 but not VRI ameliorated the MPTP-induced deficit of swimming behavior, which was also rescued by treatment with L-dopa and L-deprenyl (selegiline) as positive controls. Neither SU5416 nor VRI treatment alone notably altered the swimming behavior of normal zebrafish larvae (FIG. 15).

Figure 16:
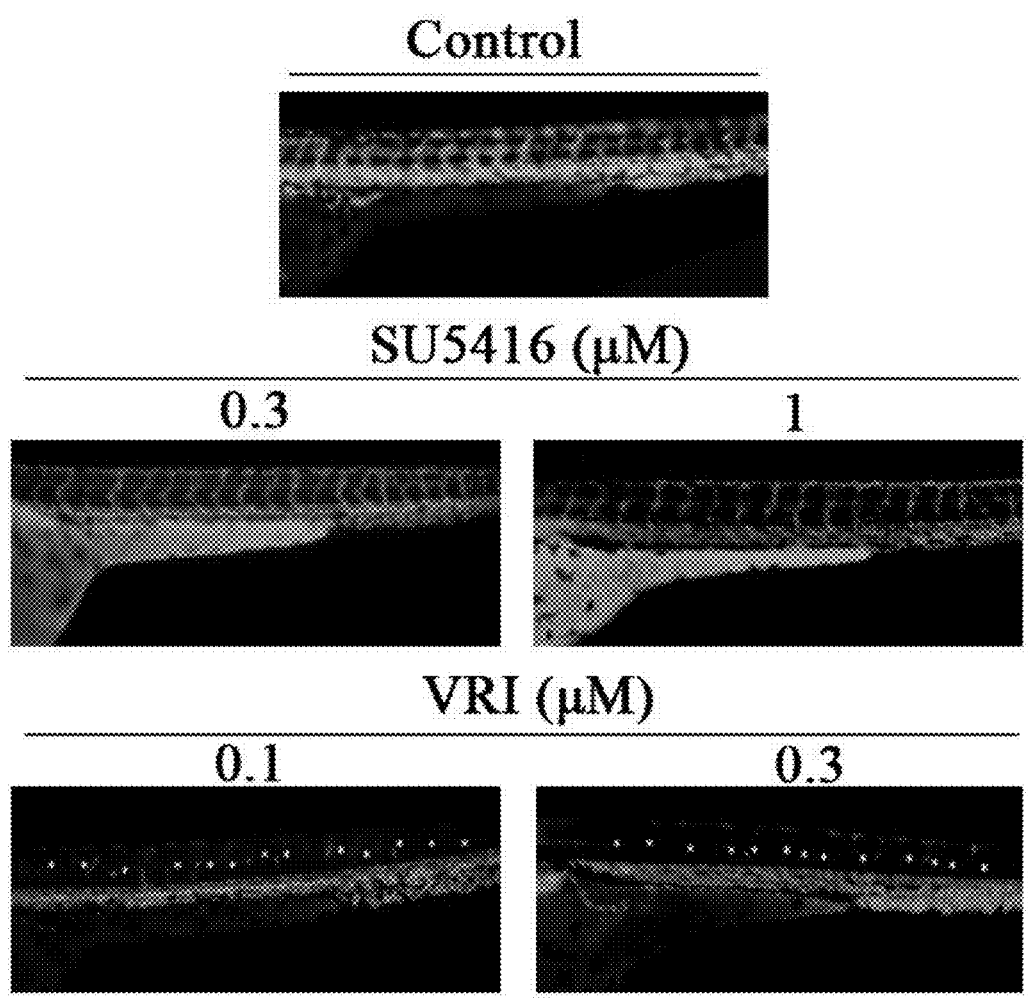
FIG. 16 shows the anti-angiogenic effects of SU5416 and VRI in zebrafish. One dpf Tg (fli-1:EGFP) transgenic zebrafish embryos were treated with SU5416, VRI or DMSO (vehicle control) at the indicated concentrations for 2 days. After treatment, intersegmental-vessel formations were observed under fluorescence microscopy. Deficit of blood vessels was indicated by yellow asterisks.

2.2.3) The Neuroprotective Effects of SU5416 were not Directly Correlated with its Anti-Angiogenic Action It was further determined if SU5416 at particular concentration ranges exhibited any anti-angiogenic activities in Tg(fli1:EGFP) transgenic zebrafish embryos. Owing to the genetic addition of a GFP gene under the control of the fli-1 promoter, the fli-1 promoter activity in the endothelial cells of such zebrafish model can be directly observed using fluorescence microscopy. As shown in FIG. 16, VRI (0.1-0.3 µM) inhibited the formation of intersegmental-vessels in zebrafish larvae, whereas SU5416 (0.3-1 µM) did not show this activity.

2.2.4) SU5416 Prevented $MPP^+$-Induced Increase of Intracellular NO Release

Figure 17:
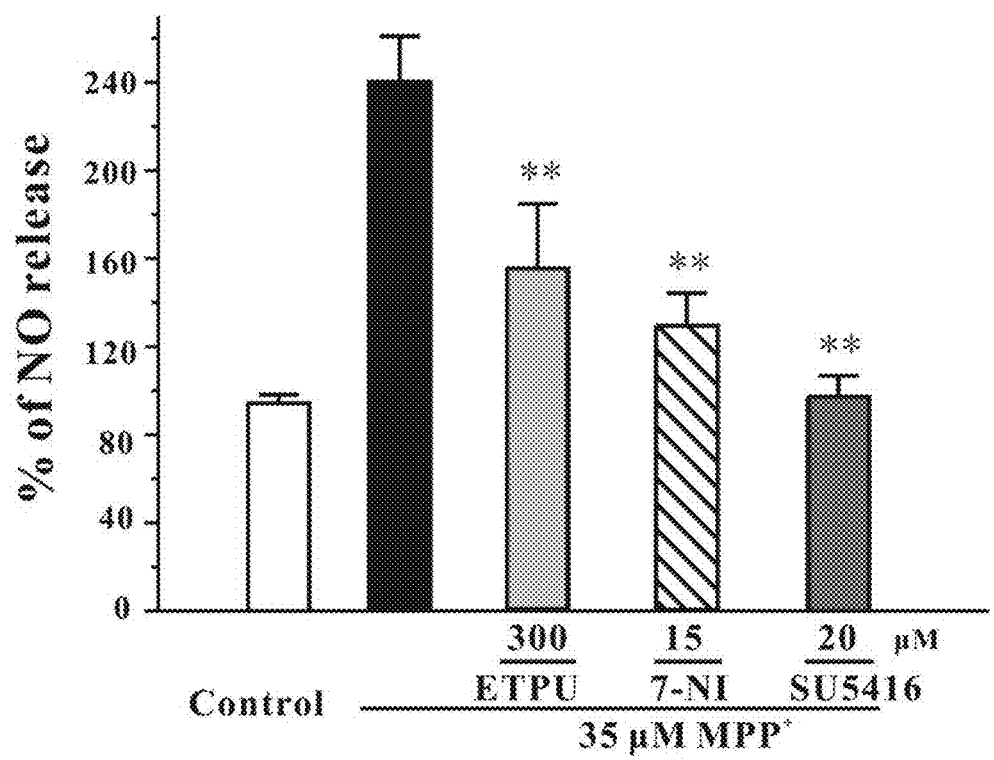
FIG. 17 shows SU5416 reversed the elevated intracellular NO induced by MPP$^+$ in CGNs. CGNs were pre-incubated with EPTU, 7-N1 or SU5416 at the indicated concentrations for 2 hours, and exposed to 35 μM MPP$^+$. Intracellular NO level was measured using DAF-FM diacetate as a probe at 8 hour after MPP$^+$ challenge. Data, expressed as percentage of control, were the mean±SEM of three separate experiments; **$p<0.01$ versus MPP$^+$ group (ANOVA and Dunnett's test).

To investigate whether SU5416 protected against $MPP^+$-induced neurotoxicity from acting on NO release, an intracellular NO measurement was used in this study. When CGNs were treated with SU5416 and $MPP^+$ simultaneously, SU5416 antagonized the stimulatory effect of $MPP^+$ on the NO production with an efficacy similar to 7-nitroindazole (15 µM) (FIG. 17). These results suggest that the neuroprotection of SU5416 against $MPP^+$-induced neuronal loss might be mediated by decreasing NO neurotoxicity, probably by inhibiting nNOS over-activation.

2.2.5) SU5416 Reduced $MPP^+$-Increased Expression of nNOS Protein

Figure 18:
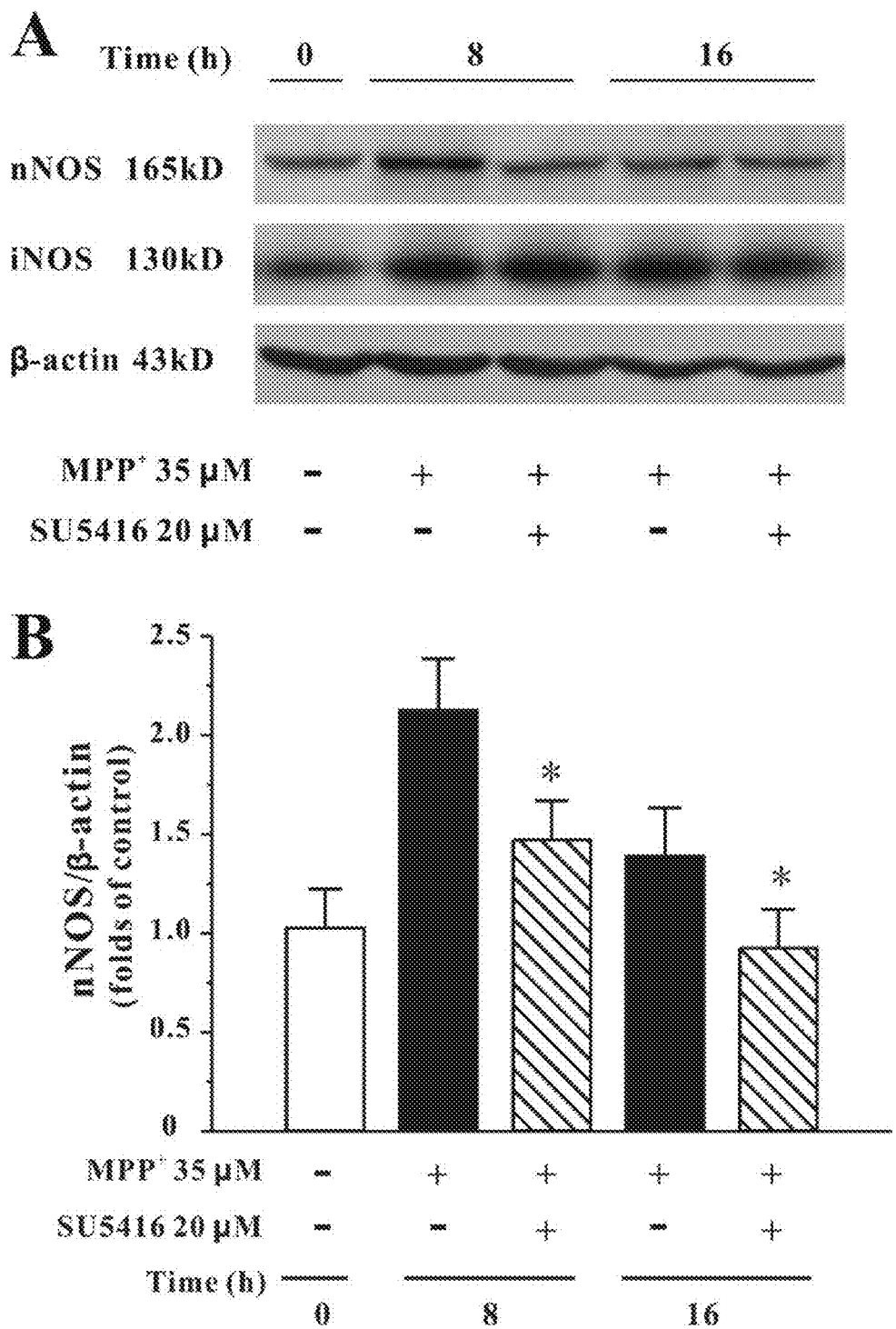
FIG. 18 shows SU5416 reduced the expression of nNOS protein elevated by MPP$^+$ in CGNs. (A) CGNs were pretreated with 20 μM SU5416 or DMSO (vehicle control) for 2 hours, and then treated with 35 μM MPP$^+$ for various durations as indicated. The total proteins were extracted for Western blot analysis with specific iNOS, nNOS and β-actin antibodies. (B) Statistical analysis of nNOS expression in each treatment group. Data are expressed as the ratio to OD values of the corresponding controls. Data, expressed as percentage of control, were the mean±SEM of five separate experiments; *$p<0.05$ versus MPP$^+$ group at the same time (Turkey's test).

To determine the effect of SU5416 on the protein expressions of nNOS and iNOS in CGNs, Western blotting analysis was used. As shown in FIG. 18, SU5416 at 20 µM reversed the increased expression of nNOS by $MPP^+$. However, SU5416 at the same concentration could not affect the elevated expression of iNOS by $MPP^+$ (FIG. 18A).

2.2.6) SU5416 Directly Inhibited the Activity of nNOS

Figure 19:
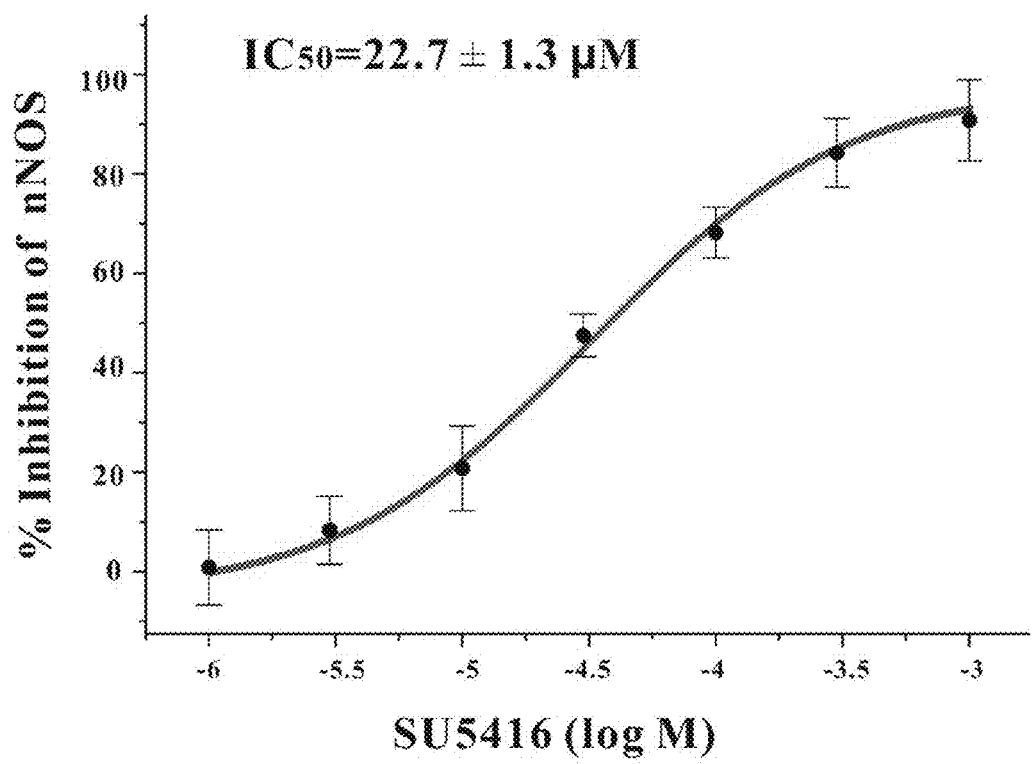
FIG. 19 shows SU5416 directly inhibited nNOS enzyme activity in a concentration-dependent manner. The inhibitory effects of SU5416 on rat cerebellum nNOS were shown in the graph. The IC50 value was also indicated. Each individual point was an average from three independent experiments.

Furthermore, to investigate whether SU5416 also affected the activity of nNOS, an in vitro NOS activity assay was used in this study. It was found that SU5416 directly inhibited rat cerebellum nNOS in a concentration-dependent manner with an $IC_{50}$ value of 22.7 µM (FIG. 19). These results suggest that SU5416 not only decreased the expression of nNOS, but also directly inhibited the activity of nNOS.

2.2.7) nNOS Depletion Abolished the Neuroprotective Effects of SU5416

Figure 20:
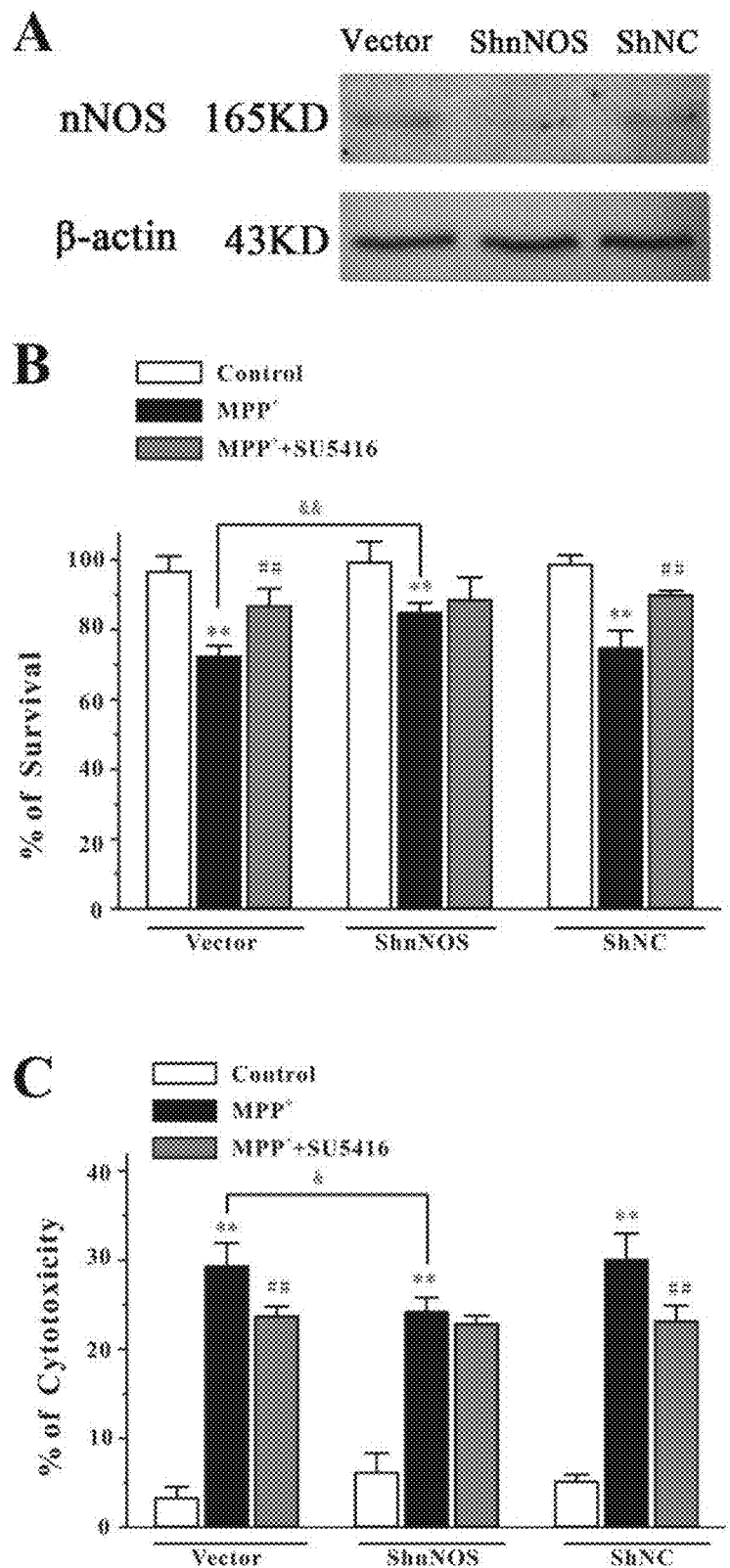
FIG. 20 shows nNOS depletion abolished the neuroprotective effects of SU5416 against MPP$^+$-induced neuronal death in PC12 cells. (A) PC12 cells were transfected with pG418-GFP plasmid (vector), pG418-GFP plasmid encoding nNOS ShRNA (ShnNOS) and pG418-GFP plasmid encoding negative control ShRNA (ShNC). The levels of nNOS and β-actin in the cell lysates were analyzed by Western blotting assay by using specific antibodies. (B, C) nNOS depletion abolished the neuroprotective effects of SU5416 against MPP$^+$-induced neuronal death in PC12 cells. PC12 cells transfected with vector, ShnNOS, or ShNC were treated with 20 μM SU5416 for 2 hours and then exposed to 1 mM MPP$^+$. Cell viability (B) and cytotoxicity (C) were measured at 24 hours after MPP$^+$ challenge by MTT and LDH assays, respectively. Data were the mean±SEM of three separate experiments; **$p<0.01$ versus control; $^{\#\#}p<0.01$ versus MPP$^+$ group; $^{\&}p<0.05$ and $^{\&\&}p<0.01$ versus MPP$^+$ vector group (Turkey's test).

To explore if the neuroprotective effects of SU5416 mainly act through nNOS, the neuroprotection of SU5416 against MPP$^+$-induced neurotoxicity in ShRNA-mediated nNOS knockdown PC12 cells was investigated. Western blot analysis showed that nNOS ShRNA (ShnNOS) caused a reduction in nNOS protein level, whereas the negative control ShRNA (ShNC) had no effect on nNOS protein level (FIG. 20A). Analyses of cell viability and cytotoxicity revealed that nNOS depletion resulted in a significant decrease in MPP$^+$-induced cell death (FIGS. 20B and 20C). It was found that, in contrast to the neuroprotection effects of SU5416 observed in the vector or in the ShNC treated PC12 cells, SU5416 in nNOS knockdown PC12 cells was no longer able to inhibit MPP$^+$-induced cell death (FIGS. 20B and 20C). These results provided direct supporting evidence that the neuroprotective effects of SU5416 mainly act through the nNOS enzyme.

2.3) Discussion

SU5416 is the first clinically evaluated VEGFR-2 inhibitor. Although previous clinical trials did not recommend SU5416 as an anti-cancer drug, SU5416 appeared to be safe in human use. In this study, it was demonstrated for the first time that SU5416 was a promising neuroprotectant against MPP$^+$/MPTP-induced neurotoxicity both in vitro and in zebrafish. These results further revealed that the neuroprotection of SU5416 was not closely correlated with its anti-angiogenic action, but via attenuating NO-mediated neurotoxicity, possibly by both decreasing nNOS protein expression and directly inhibiting nNOS enzyme activity.

SU5416 was originally designed as a potent VEGFR-2 inhibitor with an IC$_{50}$ value of 0.39 μM against the cellular VEGFR-2 tyrosine kinase activity (Sun et al., 1998). To clarify whether its neuroprotection was due to the inhibition of VEGFR-2-dependent angiogenesis, another potent and selective VEGFR-2 inhibitor VRI was assessed in parallel. Interestingly, SU5416 at its neuroprotective concentration did not inhibit angiogenesis, whereas VRI did not prevent neuronal loss at the concentration in which it showed potent anti-angiogenic activity. These results suggest that the neuroprotection of SU5416 was not closely correlated with its anti-angiogenic property. Previous studies also showed that the activation of VEGFR-2 promoted neuronal survival by regulating phosphoinositide 3-kinase (PI3-K)/Akt and extracellular signal-regulated kinase (ERK) pathways (Zhu et al., 2003). The PI3-K/Akt signaling pathway is a pro-survival pathway, whereas the ERK pathway is a pro-apoptotic pathway in MPP$^+$-induced neuronal apoptosis in CGNs (Cui et al., 2011). To examine whether SU5416 acts on downstream pathways of VEGFR-2, such as the ERK and Akt pathways, to protect against MPP$^+$-induced neurotoxicity, the activities of phospho-Akt (pAkt) and phospho-ERK (pERK) in Western blot assay were tested (data not shown). These results show that SU5416 could neither inhibit the activation of pro-apoptotic ERK pathway, nor reverse the decrease of pro-survival Akt pathway, suggesting that the neuroprotective effect of SU5416 is independent from the regulation of the PI3-K/Akt and ERK pathways.

It is well-known that NO is a central pro-apoptotic factor mediating the neurotoxicity of MPP$^+$/MPTP both in vitro and in vivo (Przedborski et al., 1996; Gonalez-Polo et al., 2004). Intracellular NO could form peroxynitrite by reacting with superoxide, a kind of reactive oxygen species overproduced in MPP$^+$-treated neurons. The resulted peroxynitrite could directly cause neuronal loss by nitrating cellular protein, damaging DNA and disrupting mitochondria (Beckman et al., 1990). It was found that SU5416 decreased the elevated level of intracellular NO induced by MPP$^+$, which suggested that SU5416 might exert its neuroprotective effects by regulating NO formation. Endogenous NO is mainly produced by a family of NOS enzymes. Three isoforms of NOS, namely nNOS(NOS-1), iNOS(NOS-2) and endothelial NOS (eNOS, NOS-3), have been identified so far. It is noteworthy that ablation of eNOS has no bearing on MPP$^+$-induced neurotoxicity (Gonalez-Polo et al., 2004). In the present study, it was demonstrated that MPP$^+$ increased the expression of nNOS, but not iNOS in CGNs. nNOS inhibitor 7-nitroindazole, but not iNOS inhibitor 1400W, reduced MPP$^+$-induced neuronal loss. These results suggested that MPP$^+$-induced neurotoxicity was mainly mediated by the over-activation of nNOS, and SU5416 prevented neurotoxicity possibly by targeting nNOS.

According to Western blotting analysis, SU5416 reduced MPP$^+$-elevated protein expression of nNOS. By assaying in vitro NOS activity, it was further demonstrated that SU5416 directly inhibited the activity of nNOS with IC$_{50}$ value of 22.7 μM. Most importantly, nNOS depletion abolished the neuroprotective effects of SU5416 against MPP$^+$-induced neuronal death. These results strongly suggested that SU5416 most likely prevented NO-mediated neurotoxicity via both inhibiting the activity and decreasing the expression of nNOS. Although the precise mechanisms underlying the decrease of nNOS expression induced by SU5416 is still unclear, a recent study demonstrated that SU5416 could down-regulate the PI3K/Akt signaling pathway, a critical mediator in the activation of nNOS gene transcription induced by retinoic acid (Nagl et al., 2009), suggesting that SU5416 might reduce the protein expression of nNOS via down-regulating the Akt pathway.

The production of neurotoxic NO by nNOS is implicated in many neurodegenerative disorders. Selective nNOS inhibitors may thus have therapeutic potential in treating neurodegenerative disorders by preventing neuronal death (Thomas et al., 2008). In this study, it was shown for the first time that SU5416 possesses neuroprotective potential against MPP$^+$/MPTP-induced neurotoxicity both in vitro and in vivo. It was also demonstrated that SU5416 prevents neurotoxicity by reducing nNOS protein expression and directly inhibiting the enzyme activity of nNOS. In view of the capability of SU5416 to cross the blood-brain barrier and the safety for human use, these findings further indicate that SU5416 might be a novel drug candidate for neurodegenerative disorders and CNS cancers, particularly those associated with NO-mediated neurotoxicity.

Example 3

Neuroprotection by Sunitinib

This example demonstrates sunitinib exerts unexpected neuroprotective effects via inhibiting NO overproduction at clinically relevant concentrations, possibly from directly inhibiting the enzyme activity of nNOS.

3.1) Results 3.1.1) Sunitinib, but not PTK787, Unexpectedly Prevents Low Potassium-Induced Apoptosis in CGNs It was previously reported that low potassium could induce typical apoptosis in cerebellar granule neurons (CGNs) (Fu et al., 2008). At 8 day in vitro, CGNs were switched to the 5 mM KCl BME medium (low potassium challenge) containing gradually increasing concentrations of sunitinib (0.1-2 μM). Cell viability was measured with an MTT assay 24 hours after the low potassium treatment. It was found that sunitinib unexpectedly prevented low potassium-induced cell death in CGNs in a concentration-dependent manner (FIG. 21A). The treatments with 2 µM sunitinib alone for 26 hours did not show cell proliferative or cytotoxic effects in CGNs (data not shown). PTK787 (another RTKs inhibitor) and L-NMMA (a NOS inhibitor, $IC_{50}$ values of 0.65 µM for nNOS, 3.9 µM for iNOS, and 0.7 µM for eNOS) were also tested in the same model. Interestingly, PTK787 at 3 and 10 µM both failed to block neuronal loss in vitro (FIG. 21A). L-NMMA at 10-20 µM prevented low potassium-induced neuronal death in CGNs (FIG. 21A).

To further characterize the neuroprotective effects of sunitinib on the neurotoxicity of low potassium, CGNs were switched to the 5 mM KCl BME medium containing 1.5 µM sunitinib for 24 hours. The neurons were examined by FDA/PI double staining. It was found that sunitinib significantly blocked the loss of neurons and reversed the morphological alteration, including unhealthy bodies and broken extensive neuritic network, induced by low potassium (FIGS. 21B and 21C). According to the counts of apoptotic bodies stained by Hoechst 33342, sunitinib also significantly reversed neuronal apoptosis induced by low potassium in CGNs (FIG. 21C).

3.1.2) Sunitinib Prevents Low Potassium-Induced Increase of Intracellular NO Release in CGNs To investigate whether sunitinib protected against low potassium-induced neurotoxicity from acting on NO release, an intracellular NO measurement was used in our study. When CGNs were treated with sunitinib and low potassium simultaneously, sunitinib antagonized the stimulatory effect of low potassium on the NO production (FIG. 21D). These results suggest that the neuroprotection of sunitinib on low potassium-induced neuronal loss might be mediated by decreasing NO over-production.

Figure 22:
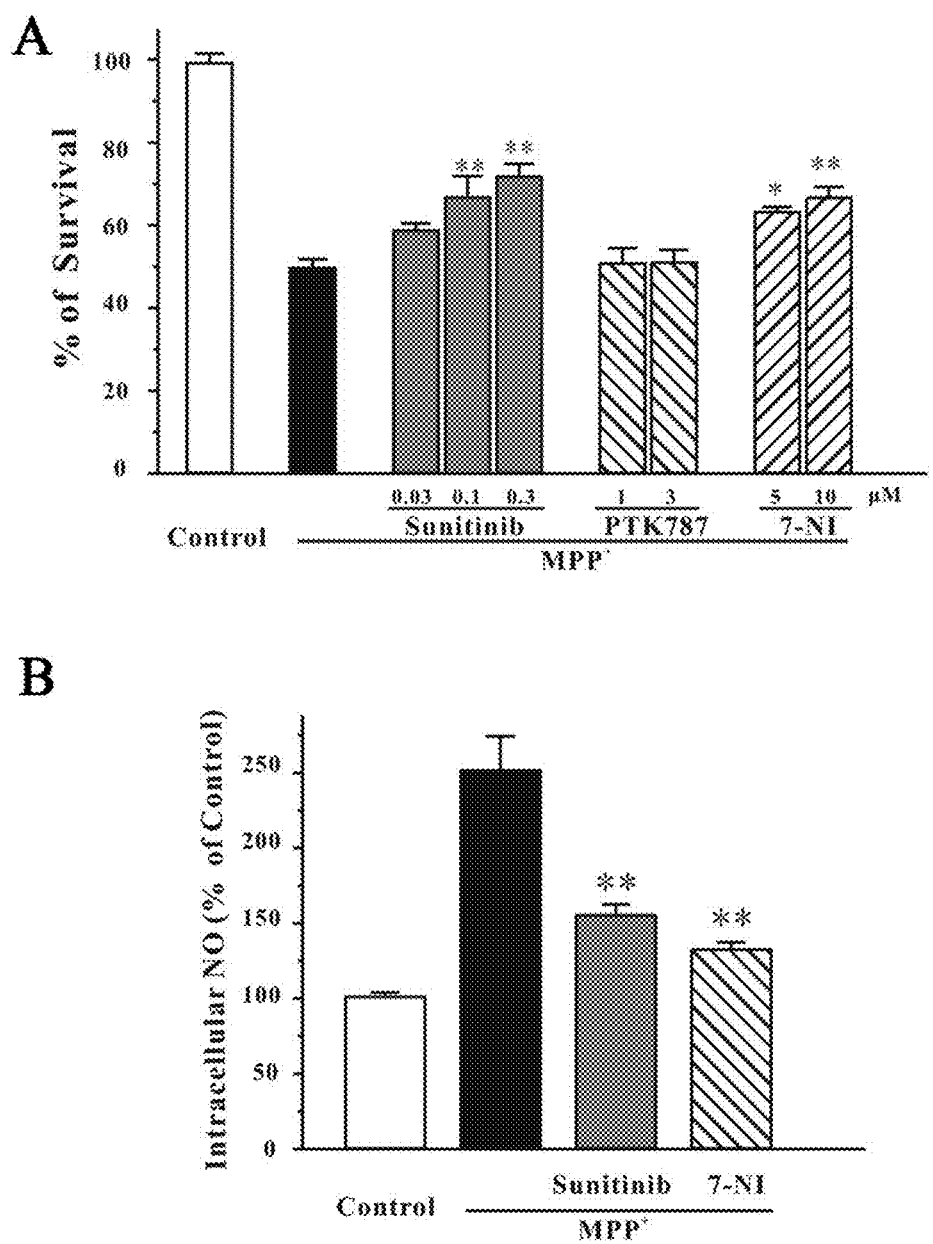
FIG. 22 shows Sunitinib reverses MPP$^+$-induced neurotoxicity and NO over-production in SH-SY5Y cells. (A) Sunitinib, but not PTK787, prevented MPP$^+$-induced cell death in a concentration-dependent manner. SH-SY5Y cells were treated with sunitinib, PTK787, 7-NI or DMSO (vehicle control) at the indicated concentrations for 2 hours and then exposed to 1 mM MPP$^+$. Cell viability was measured by the MTT assay at 24 hours after MPP$^+$ challenge. (B) Sunitinib reverses the elevated intracellular NO induced by MPP$^+$ in SH-SY5Y cells. SH-SY5Y cells were pre-incubated with 0.3 μM sunitinib, 5 μM 7-NI or DMSO (vehicle control) at the indicated concentrations for 2 hours and exposed to 1 mM MPP$^+$. Intracellular NO level was measured using DAF-FM diacetate as a probe at 24 hour after MPP$^+$ challenge. Data, expressed as percentage of control, were the mean±SEM of three separate experiments; *$p<0.05$ and **$p<0.01$ versus MPP$^+$ group (ANOVA and Dunnett's test).

3.1.3) Sunitinib at Clinically Relevant Concentrations Reverses $MPP^+$-Induced Neurotoxicity and NO Over-Production in SH-SY5Y Cells It was further determined if sunitinib could exhibit neuroprotective effects against NO-related neurotoxicity induced by other neurotoxins. Previous studies have shown that NO is implicated in the neurotoxicity of $MPP^+$ (Przedborski et al., 1996; Hantraye et al., 1996). SH-SY5Y cells were pre-treated with gradually increasing concentrations of sunitinib for 2 hours and then treated with 1 mM $MPP^+$ for another 24 hours. Cell viability was measured using the MTT assay. Sunitinib prevented $MPP^+$-induced neuronal death at 0.1-0.3 µM (50-160 ng/ml), which is comparable to its clinically relevant human plasma steady-state level (50-100 ng/ml) (Zhang et al., 2009). The treatment with 0.3 µM sunitinib alone for 26 hours did not show cell proliferative or cytotoxic effects. However, sunitinib at higher concentration (1 µM) showed toxicity to SH-SY5Y cells (data not shown). PTK787 and 7-NI (a NOS inhibitor, $IC_{50}$ values of 0.7 µM for nNOS, 0.78 µM for eNOS, and 20 µM, for iNOS) were also tested in this model. PTK787 at 1 and 3 µM failed to block neuronal loss induced by $MPP^+$ in SH-SY5Y cells (FIG. 22A). 7-NI at 5-10 µM prevented $MPP^+$-induced neuronal death in SH-SY5Y cells (FIG. 22A).

DAF-FM diacetate was also used to evaluate the intracellular NO level in this model. SH-SY5Y cells were pre-treated with 0.3 µM sunitinib for 2 hours and then exposed to 1 mM $MPP^+$ for another 24 hours. It was found that sunitinib attenuated $MPP^+$-triggered elevation of intracellular NO level, suggesting that sunitinib prevented $MPP^+$-induced neuronal loss possibly through inhibiting NO over-production (FIG. 22B).

Figure 23:
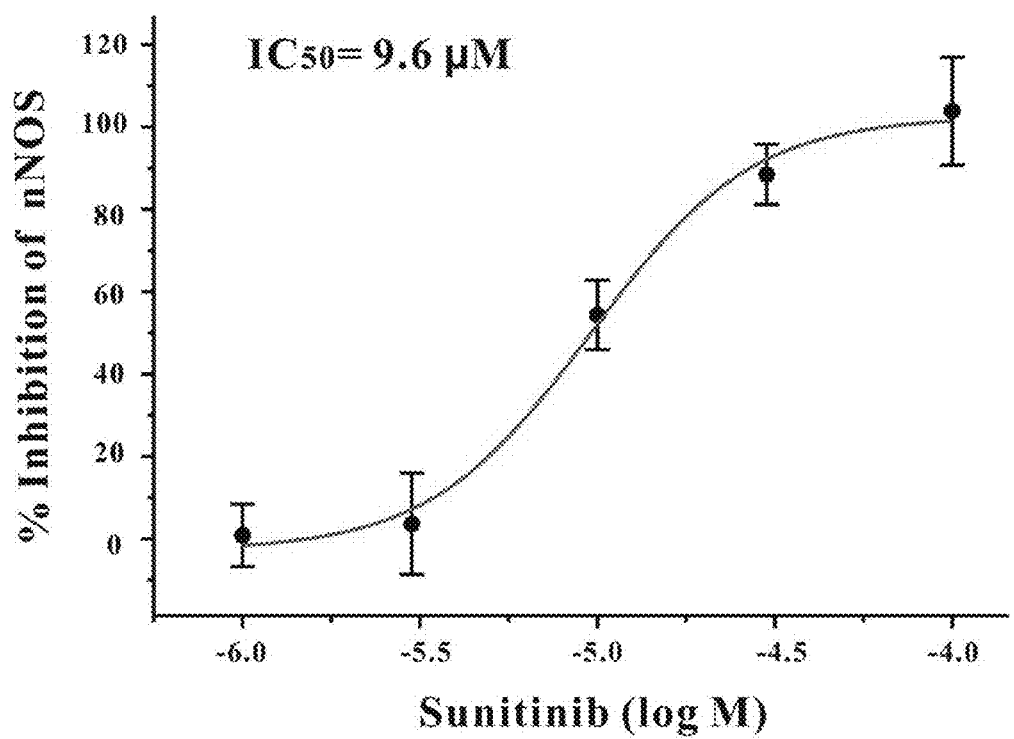
FIG. 23 shows Sunitinib directly inhibits nNOS enzyme activity in a concentration-dependent manner. The inhibitory effects of sunitinib on rat cerebellum nNOS were shown in the graph. The IC$_{50}$ value was also indicated in the graph. Each individual point was an average from three independent experiments.

3.1.4) Sunitinib Directly Inhibits nNOS Enzyme Activity in a Concentration-Dependent Manner Furthermore, to investigate whether sunitinib directly affected the enzyme activity of NOS, an in vitro NOS activity assay was used in this study. It was found that sunitinib directly inhibited rat cerebellum nNOS in a concentration-dependent manner with an $IC_{50}$ value of 9.6 µM (FIG. 23). However, sunitinib at 100 µM showed no inhibitory activity against iNOS or eNOS (data now shown).

3.1.5) nNOS Reduction Abolished the Neuroprotective Effects of Sunitinib

Figure 24:
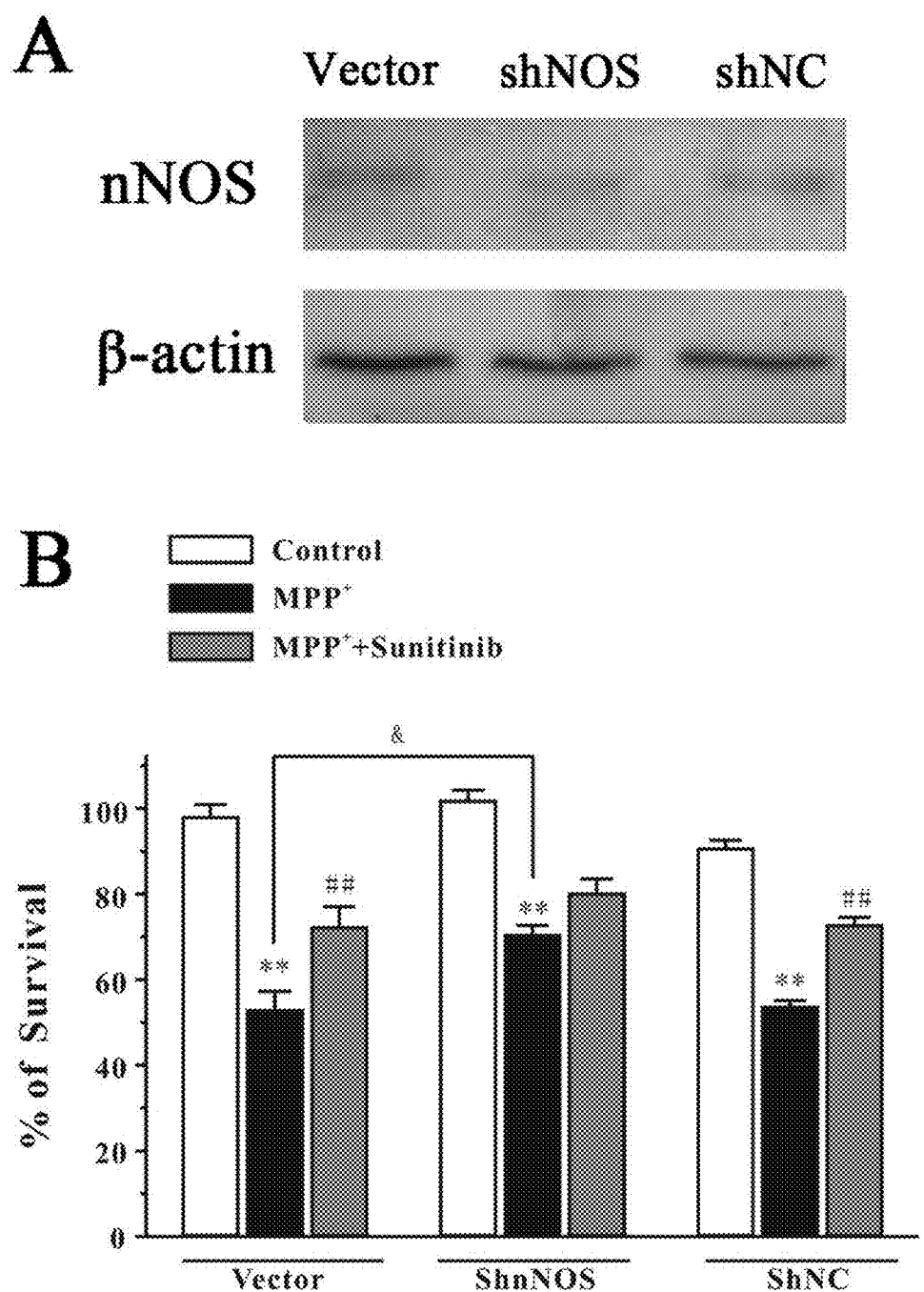
FIG. 24 shows nNOS reduction abolished neuroprotective effects of sunitinib against MPP$^+$-induced neuronal death in SH-SY5Y cells. (A) SH-SY5Y cells were transfected with pG418-GFP plasmid (vector), pG418-GFP plasmid encoding nNOS ShRNA (ShnNOS) and pG418-GFP plasmid encoding negative control ShRNA (ShNC). The level of nNOS and β-actin in the cell lysates were analyzed by Western blotting assay by using specific antibodies. (B) nNOS reduction abolished neuroprotective effects of sunitinib against MPP$^+$-induced neuronal loss in SH-SY5Y cells. SH-SY5Y cells transfected with vector, ShnNOS, or ShNC were treated with or without 0.3 μM sunitinib for 2 hours and then exposed to 1 mM MPP$^+$. Cell viability was measured at 24 hours after MPP$^+$ challenge by MTT assays. Data were the mean±SEM of three separate experiments; **$p<0.01$ versus control; $^{\#\#}p<0.01$ versus MPP$^+$ group; $^{\&}p<0.05$ versus MPP$^+$ vector group (Turkey's test).

To further determine whether neuroprotective effects of sunitinib are acting through nNOS, neuroprotection of sunitinib against $MPP^+$-induced neurotoxicity was investigated in ShRNA-mediated nNOS knockdown SH-SY5Y cells. Western blot analysis showed that nNOS ShRNA (ShnNOS) caused a reduction in nNOS protein level (FIG. 24A). Analyses of cell viability revealed that nNOS reduction resulted in a significant decrease in $MPP^+$-induced cell death (FIG. 24B). It was also found that, in contrast to the neuroprotection of sunitinib observed in the vector or in the ShNC treated SH-SY5Y cells, sunitinib in nNOS knockdown SH-SY5Y cells did not significantly inhibit $MPP^+$-induced cell death (FIG. 24B). These results provided direct evidence supporting that neuroprotective effects of sunitinib are acting through the inhibition of nNOS enzyme activity.

3.2) Discussion

Sunitinib is a multiple receptor tyrosine kinases (RTKs) inhibitor approved for the treatment of cancer (Rock et al., 2007; Adams et al., 2007). In this study, it was shown for the first time that sunitinib has unexpected neuroprotective effects against low potassium-induced neuronal apoptosis in CGNs and $MPP^+$-induced neuronal loss in SH-SY5Y cells. It was further revealed that these neuroprotections of sunitinib are independent of its anti-RTKs property, but via inhibiting NO over-production, possibly from directly inhibiting nNOS enzyme activity. These results, together with those of previous studies that showed that sunitinib is able to penetrate blood-brain barrier and safe to treat brain diseases, suggest that sunitinib may be used to treat neurodegenerative disorders, particularly those associated with NO-medicated neurotoxicity.

Clinical studies have shown that after oral administration, sunitinib could rapidly reach brain tissue with concentrations 7-fold greater than the plasma level (Patyna et al., 2006; van der Veldt et al., 2007). Although this high partitioning brain level decreased in a time-dependent manner, 25% of sunitinib was still accumulated in the brain 60 min following administration. And 60 ng/ml sunitinib was retained in the brain even at 6 hour after oral administration. The above results that show sunitinib produced neuroprotective effects even at 0.1 µM (50 ng/ml), a concentration which is comparable to its clinically relevant human plasma steady-state level (50-100 ng/ml) and brain accumulation level (60 ng/ml), indicate that sunitinib might also be useful for neurodegenerative disorders.

Sunitinib is a multiple RTKs inhibitor with IC50 values of 0.01 and 0.01 µM for VEGFR-2 and PDGFR, respectively. To clarify whether neuroprotections of sunitinib were due to the inhibition of RTKs, another potent RTKs inhibitor PTK787 ($IC_{50}$ values of 0.037 and 0.58 µM for VEGFR-2 and PDGFR, respectively) was assessed in parallel. Interestingly, PTK787 at 1-10 µM could not prevent neuronal loss, suggesting that neuroprotections of sunitinib were not closely correlated with its anti-RTKs property. Previous studies also showed that sustained (3 days) treatment of high level sunitinib (>1 µM) could reduce the proliferation of SH-SY5Y cells via inhibiting RTKs. In the present study, it was found that short-time (1 day) exposure of low level (<0.3 µM) sunitinib prevented, without exacerbating, MPP$^+$-induced neurotoxicity, provides further evidence that the neuroprotective effects of sunitinib were independent from the proliferation inhibition effect of RTKs.

NO serves as a central pro-apoptotic factor mediating the neurotoxicity of low potassium in CGNs and MPP$^+$ in SH-SY5Y cells. It was found that: 1) NOS inhibitors reduced the neuronal loss induced by low potassium and MPP$^+$; and 2) sunitinib decreased the elevated level of intracellular NO induced by low potassium and MPP$^+$, all of these are suggesting that sunitinib might exert its neuroprotective effects by regulating NO formation. By assaying in vitro NOS activity, it was found that sunitinib directly inhibited the activity of nNOS, but not iNOS or eNOS. Furthermore, nNOS reduction abolished the neuroprotective effects of sunitinib. These results suggest that sunitinib prevented neuronal loss via reducing NO-mediated neurotoxicity, possibly from directly inhibiting the activity of nNOS.

In conclusion, the present findings demonstrate that sunitinib at its clinically relevant antitumor concentrations exhibits neuroprotections against low potassium and MPP$^+$-induced neuronal loss via decreasing NO-mediated neurotoxicity. In view of the capability of sunitinib to penetrate blood-brain barrier, the present results offer support for further development of sunitinib in the treatment of neurodegenerative disorders, particularly those associated with NO-mediated neurotoxicity with and without tumor formations.

REFERENCES

Adams V. R., M. Leggas, Sunitinib malate for the treatment of metastatic renal cell carcinoma and gastrointestinal stromal tumors, Clin Ther 29 (2007) 1338-1353.

Addeo R., Caraglia M., (2011) The oral tyrosine kinase inhibitors lapatinib and sunitinib: new opportunities for the treatment of brain metastases from breast cancer?, Expert Rev Anticancer Ther 11 139-142.

Alderton W K, Cooper C E, Knowles R G (2001). Nitric oxide synthases: structure, function and inhibition. Biochem J 357(Pt 3): 593-615.

Beckman J S, Beckman T W, Chen J, Marshall P A, Freeman B A (1990). Apparent hydroxyl radical production by peroxynitrite: implications for endothelial injury from nitric oxide and superoxide. Proc Natl Acad Sci USA 87(4): 1620-1624.

Blay J. Y., (2010) Pharmacological management of gastrointestinal stromal tumours: an update on the role of sunitinib, Ann Oncol 21 208-215.

Choi D Y, Liu M, Hunter R L, Cass W A, Pandya J D, et al. (2009) Striatal neuroinflammation promotes Parkinsonism in rats. PLoS One 4: e5482.

Cui W, Li W, Han R, Mak S, Zhang H, Hu S, et al. (2011). PI3-K/Akt and ERK pathways activated by VEGF play opposite roles in MPP$^+$-induced neuronal apoptosis. Neurochem Int 59(6): 945-953.

I. M. Desar, D. M. Burger, Q. G. Van Hoesel, J. H. Beijnen, C. M. Van Herpen, W. T. Van der Graaf, (2009) Pharmacokinetics of sunitinib in an obese patient with a GIST, Ann Oncol 20 599-600.

Estevez A G, Spear N, Thompson J A, Cornwell T L, Radi R, Barbeito L, et al. (1998). Nitric oxide-dependent production of cGMP supports the survival of rat embryonic motor neurons cultured with brain-derived neurotrophic factor. J Neurosci 18(10): 3708-3714.

Fedorov R, Vasan R, Ghosh D K, Schlichting I (2004). Structures of nitric oxide synthase isoforms complexed with the inhibitor AR-R17477 suggest a rational basis for specificity and inhibitor design. Proc Natl Acad Sci USA 101(16): 5892-5897.

Fong T A, Shawver L K, Sun L, Tang C, App H, et al. (1999) SU5416 is a potent and selective inhibitor of the vascular endothelial growth factor receptor (Flk-1/KDR) that inhibits tyrosine kinase catalysis, tumor vascularization, and growth of multiple tumor types. Cancer Res 59: 99-106.

Fu H., J. Dou, W. Li, J. Luo, K. C. Li, C. S. Lam, N. T. Lee, M. Li, Y. Han, Mecamylamine prevents neuronal apoptosis induced by glutamate and low potassium via differential anticholinergic-independent mechanisms, Neuropharmacology 54 (2008) 755-765.

Gal S, Zheng H, Fridkin M, Youdim M B (2010) Restoration of nigrostriatal dopamine neurons in post-MPTP treatment by the novel multifunctional brain-permeable iron chelator-monoamine oxidase inhibitor drug, M30. Neurotox Res 17: 15-27.

Gonzalez-Polo R A, Soler G, Alvarez A, Fabregat I, Fuentes J M (2003). Vitamin E blocks early events induced by 1-methyl-4-phenylpyridinium (MPP$^+$) in cerebellar granule cells. J Neurochem 84(2): 305-315.

Gonzalez-Polo R A, Soler G, Fuentes J M (2004a). MPP$^+$: mechanism for its toxicity in cerebellar granule cells. Mol Neurobiol 30(3): 253-264.

Gonzalez-Polo R A, Soler G, Rodriguezmartin A, Moran J M, Fuentes J M (2004b). Protection against MPP$^+$ neurotoxicity in cerebellar granule cells by antioxidants. Cell Biol Int 28(5): 373-380.

Grayson M (2010) Parkinson's disease. Nature 466: S1.

Hantraye P, Brouillet E, Ferrante R, Palfi S, Dolan R, Matthews R T, et al. (1996). Inhibition of neuronal nitric oxide synthase prevents MPTP-induced parkinsonism in baboons. Nat Med 2(9): 1017-1021.

Herraiz T, Aran V J, Guillen H (2009). Nitroindazole compounds inhibit the oxidative activation of 1-methyl-4-phenyl-1,2,3,6-tetrahydropyridine (MPTP) neurotoxin to neurotoxic pyridinium cations by human monoamine oxidase (MAO). Free Radic Res 43(10): 975-984.

Kieran M W, Supko J G, Wallace D, Fruscio R, Poussaint T Y, et al. (2009) Phase I study of SU5416, a small molecule inhibitor of the vascular endothelial growth factor receptor (VEGFR) in refractory pediatric central nervous system tumors. Pediatr Blood Cancer 52: 169-176.

Langston J W, Irwin I (1986). MPTP: current concepts and controversies. Clin Neuropharmacol 9(6): 485-507.

Lee B D, Shin J H, VanKampen J, Petrucelli L, West A B, Ko H S, et al. (2010). Inhibitors of leucine-rich repeat kinase-2 protect against models of Parkinson's disease. Nat Med 16(9): 998-1000.

Lees A J, Hardy J, Revesz T (2009) Parkinson's disease. Lancet 373: 2055-2066.

McKinley E T, Baranowski T C, Blavo D O, Cato C, Doan T N, Rubinstein A L (2005). Neuroprotection of MPTP-induced toxicity in zebrafish dopaminergic neurons. Brain Res Mol Brain Res 141(2): 128-137.

McMillin D W, Delmore J, Weisberg E, Negri J M, Geer D C, Klippel S, et al. (2010). Tumor cell-specific bioluminescence platform to identify stroma-induced changes to anticancer drug activity. Nat Med 16(4): 483-489.

Medioni J., Cojocarasu O., Belcaceres J. L., Halimi P., Oudard S., (2007) Complete cerebral response with sunitinib for metastatic renal cell carcinoma, Ann Oncol 18 1282-1283.

Miki A, Miki K, Ueno S, Wersinger D M, Berlinicke C, Shaw G C, et al. (2010). Prolonged blockade of VEGF receptors does not damage retinal photoreceptors or ganglion cells. J Cell Physiol 224(1): 262-272.

Muramatsu Y, Kurosaki R, Watanabe H, Michimata M, Matsubara M, et al. (2003) Cerebral alterations in a MPTP-mouse model of Parkinson's disease—an immunocytochemical study. J Neural Transm 110: 1129-1144.

Nagl F, Schonhofer K, Seidler B, Mages J, Allescher H D, et al. (2009) Retinoic acid-induced nNOS expression depends on a novel PI3K/Akt/DAX1 pathway in human TGW-nu-I neuroblastoma cells. Am J Physiol Cell Physiol 297: C1146-1156.

Patyna S., G. Peng, (2006) Distribution of sunitinib and its active metabolite in brain and spinal cord tissue following oral or intravenous administration in rodents and monkeys, Eur J Cancer Suppl 12: 21.

Przedborski S, Jackson-Lewis V, Yokoyama R, Shibata T, Dawson V L, Dawson T M (1996). Role of neuronal nitric oxide in 1-methyl-4-phenyl-1,2,3,6-tetrahydropyridine (MPTP)-induced dopaminergic neurotoxicity. Proc Natl Acad Sci USA 93(10): 4565-4571.

Rock E. P., V. Goodman, J. X. Jiang, K. Mahjoob, S. L. Verbois, D. Morse, R. Dagher, R. Justice, R. Pazdur, (2007) Food and Drug Administration drug approval summary: Sunitinib malate for the treatment of gastrointestinal stromal tumor and advanced renal cell carcinoma, Oncologist 12 107-113.

Rodamer M, Elsinghorst P W, Kinzig M, Gütschow M (2011) Development and validation of a liquid chromatography/tandem mass spectrometry procedure for the quantification of sunitinib (SU11248) and its active metabolite, N-desethyl sunitinib (SU12662), in human plasma: application to an explorative study. J Chromatogr B Analyt Technol Biomed Life Sci. 879(11-12):695-706.

Roman L J, Masters B S (2006). Electron transfer by neuronal nitric-oxide synthase is regulated by concerted interaction of calmodulin and two intrinsic regulatory elements. J Biol Chem 281(32): 23111-23118.

Sabaliauskas N A, Foutz C A, Mest J R, Budgeon L R, Sidor A T, et al. (2006) High-throughput zebrafish histology. Methods 39: 246-254.

Schultheiss C, Blechert B, Gaertner F C, Drecoll E, Mueller J, Weber G F, et al. (2006). In vivo characterization of endothelial cell activation in a transgenic mouse model of Alzheimer's disease. Angiogenesis 9(2): 59-65.

Scott G S, Kean R B, Mikheeva T, Fabis M J, Mabley J G, Szabo C, et al. (2004). The therapeutic effects of PJ34 [N-(6-oxo-5,6-dihydrophenanthridin-2-yl)-N,N-dimethylacetamide.HCl], a selective inhibitor of poly(ADP-ribose) polymerase, in experimental allergic encephalomyelitis are associated with immunomodulation. J Pharmacol Exp Ther 310(3): 1053-1061.

Shawver L K, Slamon D, Ullrich A (2002) Smart drugs: tyrosine kinase inhibitors in cancer therapy. Cancer Cell 1: 117-123.

Shin J H, Dawson V L, Dawson T M (2009) SnapShot: pathogenesis of Parkinson's disease. Cell 139: 440 e441-442.

Spitsin S, Portocarrero C, Phares T W, Kean R B, Brimer C M, Koprowski H, et al. (2008). Early blood-brain barrier permeability in cerebella of PLSJL mice immunized with myelin basic protein. J Neuroimmunol 196(1-2): 8-15.

Stopeck A, Sheldon M, Vahedian M, Cropp G, Gosalia R, et al. (2002) Results of a Phase I dose-escalating study of the antiangiogenic agent, SU5416, in patients with advanced malignancies. Clin Cancer Res 8: 2798-2805.

Sun L, Tran N, Tang F, App H, Hirth P, McMahon G, et al. (1998). Synthesis and biological evaluations of 3-substituted indolin-2-ones: a novel class of tyrosine kinase inhibitors that exhibit selectivity toward particular receptor tyrosine kinases. Journal of medicinal chemistry 41(14): 2588-2603.

Thomas B, Saravanan K S, Mohanakumar K P (2008) In vitro and in vivo evidences that antioxidant action contributes to the neuroprotective effects of the neuronal nitric oxide synthase and monoamine oxidase-B inhibitor, 7-nitroindazole. Neurochem Int 52: 990-1001.

Tipton K F, Singer T P (1993). Advances in our understanding of the mechanisms of the neurotoxicity of MPTP and related compounds. J Neurochem 61(4): 1191-1206.

Totrov M, Abagyan R (1997). Flexible protein-ligand docking by global energy optimization in internal coordinates. Proteins Suppl 1: 215-220.

Tran T C, Sneed B, Haider J, Blavo D, White A, Aiyejorun T, et al. (2007). Automated, quantitative screening assay for antiangiogenic compounds using transgenic zebrafish. Cancer Res 67(23): 11386-11392.

van der Veldt A. A., A. J. van den Eertwegh, K. Hoekman, F. Barkhof, E. Boven, Reversible cognitive disorders after sunitinib for advanced renal cell cancer in patients with preexisting arteriosclerotic leukoencephalopathy, Ann Oncol 18 (2007) 1747-1750.

Wen L, Wei W, Gu W, Huang P, Ren X, Zhang Z, et al. (2008). Visualization of monoaminergic neurons and neurotoxicity of MPTP in live transgenic zebrafish. Dev Biol 314(1): 84-92.

Westerfield M (1993). The Zebrafish book: a guide for the laboratory use of zebrafish (Brachydanio rerio). edn. University of Oregon Press: Eugene. Or.

Xue F, Li H, Delker S L, Fang J, Martasek P, Roman L J, et al. (2010). Potent, highly selective, and orally bioavailable gem-difluorinated monocationic inhibitors of neuronal nitric oxide synthase. J Am Chem Soc 132(40): 14229-14238.

Ye C, Sweeny D, Sukbuntherng J, Zhang Q, Tan W, et al. (2006) Distribution, metabolism, and excretion of the anti-angiogenic compound SU5416. Toxicol In Vitro 20: 154-162.

Zhang L., K. M. Smith, A. L. Chong, D. Stempak, H. Yeger, P. Marrano, P. S. Thorner, M. S. Irwin, D. R. Kaplan, S. Baruchel, In vivo antitumor and antimetastatic activity of sunitinib in preclinical neuroblastoma mouse model, Neoplasia 11 (2009) 426-435.

Zhang Z J, Cheang L C, Wang M W, Lee S M (2011). Quercetin exerts a neuroprotective effect through inhibition of the iNOS/NO system and pro-inflammation gene expression in PC12 cells and in zebrafish. Int J Mol Med 27(2): 195-203.

Zhou L, Zhu D Y (2009). Neuronal nitric oxide synthase: structure, subcellular localization, regulation, and clinical implications. Nitric Oxide 20(4): 223-230.

Zhu Y, Jin K, Mao X O, Greenberg D A (2003) Vascular endothelial growth factor promotes proliferation of cortical neuron precursors by regulating E2F expression. FASEB J 17: 186-193.

What is claimed is:

1. A method for treating Parkinson's or Alzheimer's disease in a subject, comprising the step of administering to the subject in need thereof a composition comprising SU4312, or optical isomers and salts thereof, at an amount that is effective in inhibiting the activity of neuronal Nitric Oxide Synthase (nNOS), wherein said Parkinson's or Alzheimer's disease is associated with excessive nNOS activities.

2. The method of claim 1, wherein the Parkinson's or Alzheimer's disease is characterized by one or more symptoms selected from the group consisting of cognitive function degeneration, movement function degeneration, neuronal loss, neuronal synaptic dysfunction, excessive monoamine oxidase-B activity, lack of tyrosine hydroxylase activity, excessive deposition of proteins as fibers or plaques extra- or intra-cellularly, mitochondrial dysfunction, and neural inflammation.

3. The method of claim 1, wherein the concentration of SU4312 is about 0.3-30 µM.

4. The method of claim 1, wherein the composition is administered in combination with other compound(s) that treats the Parkinson's or Alzheimer's disease.

5. The method of claim 1, wherein the subject is a vertebrate, a mammal or human.

6. The method of claim 1, wherein the composition is delivered to target cells using stem cells, induced pluripotent cells (iPSC), mesenchymal stem cells (MSC), bacterial ghosts or mini-cells, nano-encapsulated particles, or liposomes.

7. The method of claim 1, wherein the composition is administered via a route selected from the group consisting of oral, nasal, otic, ocular, sublingual, buccal, systemic, cerebral spinal fluid injection, transdermal, and mucosal.

8. The method of claim 1, wherein the composition is formulated in the form of tablets, granules, injection, powder, solution, suspension, sprays, patches or capsules.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
caagattcca tacccaggaa gga          23

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
caacggaaac gctcattgc          19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
gcacuggugg agaucaaca          19